United States Patent
Li et al.

(10) Patent No.: US 10,442,793 B2
(45) Date of Patent: Oct. 15, 2019

(54) OXA SPIRO DERIVATIVE, PREPARATION METHOD THEREFOR, AND APPLICATIONS THEREOF IN MEDICINES

(71) Applicants: Jiangsu Hengrui Medicine Co., Ltd., Lianyungang, Jiangsu (CN); Shanghai Hengrui Pharmaceutical Co., Ltd., Shanghai (CN)

(72) Inventors: Xin Li, Shanghai (CN); Binqiang Feng, Shanghai (CN); Yang Chen, Shanghai (CN); Tao Liu, Shanghai (CN); Feng He, Shanghai (CN); Mingxun He, Shanghai (CN); Weikang Tao, Shanghai (CN); Piaoyang Sun, Jiangsu (CN)

(73) Assignees: Jiangsu Hengrui Medicine Co., Ltd, Lianyungang, Jiangsu (CN); Shanghai Hengrui Pharmaceutical Co., Ltd., Shanghai (CN)

( * ) Notice: Subject to any disclaimer, the term of this patent is extended or adjusted under 35 U.S.C. 154(b) by 0 days.

(21) Appl. No.: 15/766,985

(22) PCT Filed: Sep. 30, 2016

(86) PCT No.: PCT/CN2016/101064
§ 371 (c)(1),
(2) Date: Apr. 9, 2018

(87) PCT Pub. No.: WO2017/063509
PCT Pub. Date: Apr. 20, 2017

(65) Prior Publication Data
US 2018/0297988 A1 Oct. 18, 2018

(30) Foreign Application Priority Data
Oct. 15, 2015 (CN) .......................... 2015 1 0665328

(51) Int. Cl.
| A61K 31/352 | (2006.01) |
| A61P 25/00 | (2006.01) |
| C07D 405/04 | (2006.01) |
| C07D 405/14 | (2006.01) |
| C07D 409/00 | (2006.01) |
| C07D 409/02 | (2006.01) |
| C07D 409/14 | (2006.01) |
| A61K 31/4436 | (2006.01) |

(52) U.S. Cl.
CPC ........ *C07D 405/04* (2013.01); *A61K 31/4436* (2013.01); *A61P 25/00* (2018.01); *C07D 405/14* (2013.01); *C07D 409/14* (2013.01)

(58) Field of Classification Search
CPC .. C07D 405/04; C07D 405/14; C07D 409/00; C07D 409/02; C07D 409/14; A61K 31/352; A61P 25/00
See application file for complete search history.

(56) References Cited

U.S. PATENT DOCUMENTS

| 2003/0100598 A1 | 5/2003 | Mourelle Mancini et al. |
| 2003/0225116 A1 | 12/2003 | Chizh et al. |
| 2010/0009986 A1 | 1/2010 | Zemolka et al. |

FOREIGN PATENT DOCUMENTS

| CN | 103702561 A | 4/2014 |
| WO | 2001049650 A1 | 7/2001 |
| WO | 2002020481 A2 | 3/2002 |
| WO | 2008009415 A2 | 1/2008 |
| WO | 2009018169 A1 | 2/2009 |
| WO | 2010051476 A1 | 5/2010 |
| WO | 2010148191 A2 | 12/2010 |
| WO | 2012129495 A1 | 9/2012 |
| WO | 2013087589 A1 | 6/2013 |
| WO | 2014022733 A1 | 2/2014 |
| WO | 2014078454 A1 | 5/2014 |

OTHER PUBLICATIONS

Lutz et al. "Opioids receptors: distinct roles in mood disorders" Trends Neurosci., 2013, 36(3), pp. 195-206. (Year: 2013).*
Anselmi et al. "Activation of mu Opioid Receptors Modulates Inflammation in Acute Experimental Colitis" Neurogastroenterol Motil, 2015, 27(4), pp. 509-523. (Year: 2015).*
Acosta-Marinez et al. "Activation of mu-Opioid Receptors Inhibits Lordosis Behavior in Estrogen and Progesterone-Primed Female Rats" Hormones and Behavior, 2002, 41, pp. 88-100. (Year: 2002).*
Fichna et al., "The Endomorphin System and Its Evolving Neurophysiological Role," Pharmacol Rev, vol. 59, No. 1, pp. 88-123 (2007).
Zubieta et al."Regional Mu Opioid Receptor Regulation of Sensory and Affective Dimensions of Pain," Science, vol. 293, pp. 311-315 (2001).

(Continued)

*Primary Examiner* — Kendra D Carter
(74) *Attorney, Agent, or Firm* — Panitch Schwarze Belisario & Nadel LLP

(57) ABSTRACT

The present invention relates to an oxa spiro derivative, a preparation method therefor, and applications thereof in medicines. Particularly, the present invention relates to an oxa spiro derivative represented by formula (I), a preparation method therefor, and a pharmaceutical composition comprising the derivative, applications thereof as an MOR receptor agonist, and applications in the preparation of drugs for treating and/or preventing pains and pains-related diseases. Substituent groups in the formula (I) are same as definitions in the specification.

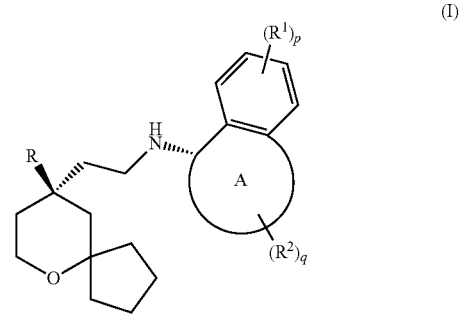

(I)

24 Claims, No Drawings

(56) References Cited

OTHER PUBLICATIONS

Champion et al.,"The Endogenous Mu-Opioid Receptor Agonists Endomorphins 1 and 2 Have Novel Hypotensive Activity in the Rabbit," Biochemical and Biophysical Research Communications, vol. 235, No. 3, pp. 567-570 (1997).
Champion et al.,"The Endogenous μ-Opioid Agonists, Endomorphin 1 and 2, Have Vasodilator Activity in the Hindquarters Vascular Bed of the Rat," Life Sci, vol. 61, No. 26, pp. PL409-PL415 (1997).
Zang et al.,"Role for G protein-coupled receptor kinase in agonist-specific regulation of μ-opioid receptor responsiveness," Proc. Natl. Acad. Sci. USA, vol. 95, pp. 7157-7162 (Jun. 1998).
Bohn et al., "Enhanced Morphine Analgesia in Mice Lacking ?-Arrestin 2," Science, vol. 286, pp. 2495-2498 (1999).
Chen et al.,"Structure-Activity Relationships and Discovery of a G Protein Biased ? Opioid Receptor Ligand, [(3-Methoxythiophen-2—yl)methyl]({2-[(9R)?9-(pyridin-2-yl)-6-oxaspiro-[4.5]decan-9-yl]ethyl})amine (TRV130), for the Treatment of Acute Severe Pain," J. Med. Chem, vol. 56, pp. 8019-8031 (2013).
Schmidt et al.,"Chroman and tetrahydroquinoline ureas as potent TRPV1 antagonists," Bioorganic & Medicinal Chemistry Letters, vol. 21, No. 5, pp. 1338-1341 (2011).
Pressnitz et al., "Asymmetric Amination of Tetralone and Chromanone Derivatives Employing ??Transaminases," ACS Catalysis, vol. 3, No. 4, pp. 555-559 (2013).
Pablo et al."Microwave-Enhanced Asymmetric Transfer Hydrogenation of N-(tert-Butylsulfinyl)imines," European Journal of Organic Chemistry, vol. 2014, No. 31, pp. 7034-7038 (2014).
Liang et al.,"Efficient Diastereoselective Intermolecular Rhodium-Catalyzed C_H Amination," Angewandte Chemie-International Edition, vol. 45. No. 28, pp. 4641-4644 (2006).
Ditrich, "Optically Active Amines by Enzyme-Catalyzed Kinetic Resolution," Synthesis, No. 14, pp. 2283-2287 (2008).
Uiterweerd et al., "(S)-1-Aminoindane: synthesis by chirality transfer using (R)-phenylglycine amide as chiral auxiliary," Tetrahedron Asymmetry, vol. 14, No. 22, pp. 3479-3485 (2003).
Rodriguez-Escrich et al.,"Exploring Structural Diversity in Ligand Design: The Aminoindanol Case," Advanced Synthesis & Catalysis, vol. 2008, No. 350, pp. 2250-2260 (2008).
Dewire et al., "G Protein-Biased Ligand at the μ-Opioid Receptor Is Potently Analgesic with Reduced Gastrointestinal and Respiratory Dysfunction Compared with Morphine," Journal of Pharmacology and Experimental Therapeutics, vol. 344, No. 3, pp. 708-717 (2013).
International Search Report dated Jan. 3, 2017 in Int'l Application No. PCT/CN2016/101064.

\* cited by examiner

OXA SPIRO DERIVATIVE, PREPARATION METHOD THEREFOR, AND APPLICATIONS THEREOF IN MEDICINES

CROSS-REFERENCE TO RELATED APPLICATION

This application is a Section 371 of International Application No. PCT/CN2016/101064, filed Sep. 30, 2016, which was published in the Chinese language on Apr. 20, 2017, under International Publication No. WO 2017/063509 A1, which claims priority under 35 U.S.C. § 119(b) to Chinese Application No. 201510665328.X, filed Oct. 15, 2015, and Chinese Application No. 201511032876.5, filed Dec. 31, 2015, the disclosures of which are incorporated herein by reference in their entirety.

FIELD OF THE INVENTION

The present invention belongs to the field of medicine, and relates to an oxa spiro derivative, a preparation method therefor, and uses thereof in medicine. In particular, the present invention relates to an oxa spiro derivative represented by formula (I), a preparation method therefor, and a pharmaceutical composition comprising the derivative, use thereof as an MOR receptor agonist, and use thereof in the preparation of a medicament for treating and/or preventing pain and pain-related diseases.

BACKGROUND OF THE INVENTION

Opioid receptors are an important G protein-coupled receptor (GPCR), and are the target of a combination of endogenous opioid peptides and opioid drugs. The activated opioid receptors play a regulatory role in immunity of the nervous system and endocrine system. Opioid drugs are the strongest and most commonly used central analgesics. Endogenous opioid peptides are naturally occurring opioid-like active substances in mammals. Currently, the known endogenous opioid peptides can be roughly divided into enkephalin, endorphin, dynorphin and nociceptin (*Pharmacol. Rev.* 2007; 59: 88-123). There are corresponding opioid receptors in the central nervous system, i.e., μ (MOR), δ (DOR), κ (KOR) receptors and the like. It was found that the strength of the analgesic effect of endogenous opioid peptides mainly depends on the expression level of opioid receptors. Opioid receptors are the targets of the analgesic effects of opioid drugs and endogenous opioid peptides. Zadina et al. found that the binding ability of the MOR receptor to morphine peptide 1 is strongest (360 pM). It's 4000 times that of the binding of the DOR receptor to morphine peptide 1, and 15000 times that of the binding of the KOR receptor to morphine peptide 1. The MOR receptor is the most important opioid receptor for mediating analgesic effects (*Science*, 2001, 293: 311-315; *Biochem. Biophys. Res. Commun.* 235:567-570; *Life Sci.* 61:PL409-PL415).

The current studies suggest that GPCR mediates and regulates physiological functions mainly through two pathways: the G protein signaling pathway and the β-arrestin pathway. The G protein signaling pathway can be activated by the binding of the traditional GPCR agonist to the receptor, and includes the second messenger system such as calcium ion, adenyl cyclase (AC), mitogen-activated protein kinases (MAPK) and the like. In contrast, the β-arrestin pathway is mainly activated by a β-arrestin-biased ligand. The β-arrestin mediated GPCR response mainly includes three aspects: 1) β-arrestin as a negative regulator reacts with the G protein-coupled receptor kinase (GRK), thereby causing receptor desensitization in GPCRs, and blocking of the transduction of G protein signaling; 2) β-arrestin as a scaffold protein recruits the endocytic protein and induces the endocytosis of GPCR; and 3) β-arrestin as an adapter protein forms a complex with GPCR downstream signaling molecules, and activates the signal transduction molecules, such as MAPK, Src protein tyrosine kinase and Akt, etc., in a G protein independent manner. The differences of ligand stimulation on G protein signaling and/or β-arrestin signaling ultimately determine the ligand-specific cellular biological effects of GPCR.

MOR is the target of opioid analgesic drugs such as endogenous enkephalin and morphine. Early studies have shown that endogenous enkephalin and the opioid drug etorphine can agonize G protein and cause receptor endocytosis, but morphine cannot cause receptor endocytosis at all. This is because the agonistic activity of morphine on MOR phosphorylation is too weak, and only trace β-arrestin is recruited yo the membrane (Zhang et al., *Proc. Natl. Acad. Sci. USA*, 1998, 95 (12): 7157-7162). These ligands exert their physiological functions completely through the G protein signaling pathway rather than the β-arrestin pathway. The study found that after morphine is injected into β-arrestin2 knockout mice, the analgesic effect mediated by G protein signaling is stronger and the duration is longer (Bohn et al., *Science*, 1999). It is foreseeable that if the negative β-arrestin bias of such ligands is stronger, even they can escape the β-arrestin mediated receptor desensitization, thereby leading to longer G protein signaling durations and more potent analgesic effects.

Patent applications disclosing MOR agonists include International Patent Application Publication Nos. WO2014022733, WO2008009415, WO2009018169, WO2012129495, WO2001049650, WO2002020481, WO2010051476 and WO2013087589 and the like.

Long-term use of opioid drugs produces side effects such as tolerance, respiratory depression and constipation. Additionally, it has been demonstrated that these side effects are closely related to the function of β-arrestin. In order to reduce the side effects of opioid drugs, the drugs can be designed based on the MOR negative β-arrestin-biased ligand, thereby reducing the β-arrestin mediated side effects and enhancing the therapeutic effect. In a study of the oxo spiro derivatives of the present invention used as selective MOR drugs, Trevena Inc. has found that the activity is lower when the substituent is on the benzylic position of the aryl (*J. Med. Chem.* 2013, 56, 8019-8031). However, after a series of studies, the present inventor has found that the oxo spiro derivatives have high activity after the benzylic position is cyclized, the Emax was significantly improved, hERG was significantly improved, and further studies found that the compound with a single configuration has a higher selectivity for the MOR.

SUMMARY OF THE INVENTION

The present invention is directed to a compound of formula (I-A), or a tautomer, mesomer, racemate, enantiomer, diastereomer thereof, or mixture thereof, or a pharmaceutically acceptable salt thereof:

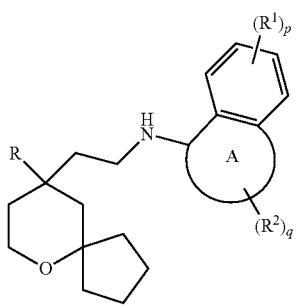

(I-A)

wherein:
ring A is selected from the group consisting of cycloalkyl and heterocyclyl;
R is selected from the group consisting of aryl and heteroaryl, wherein the aryl and heteroaryl are each optionally substituted by one or more groups selected from the group consisting of alkyl, haloalkyl, halogen, amino, nitro, cyano, alkoxy, haloalkoxy, hydroxyalkyl, cycloalkyl, heterocyclyl, aryl, heteroaryl, —$OR^3$, —$C(O)R^3$, —$C(O)OR^3$, —$S(O)_mR^3$ and —$NR^4R^5$;
each $R^1$ is identical or different and each is independently selected from the group consisting of hydrogen, alkyl, alkoxy, haloalkyl, halogen, amino, nitro, hydroxy, cyano, cycloalkyl, heterocyclyl, aryl, heteroaryl, —$OR^3$, —$C(O)R^3$, —$C(O)OR^3$, —$S(O)_mR^3$ and —$NR^4R^5$, wherein the alkyl, haloalkyl, cycloalkyl, heterocyclyl, aryl and heteroaryl are each optionally substituted by one or more groups selected from the group consisting of alkyl, haloalkyl, halogen, amino, nitro, cyano, hydroxy, alkoxy, haloalkoxy, hydroxyalkyl, cycloalkyl, heterocyclyl, aryl and heteroaryl;
each $R^2$ is identical or different and each is independently selected from the group consisting of hydrogen, alkyl, alkoxy, haloalkyl, halogen, amino, nitro, hydroxy, cyano, oxo, alkenyl, cycloalkyl, heterocyclyl, aryl, heteroaryl, —$OR^3$, —$C(O)R^3$, —$C(O)OR^3$, —$S(O)_mR^3$ and —$NR^4R^5$, wherein the alkyl, alkoxy, alkenyl, haloalkyl, cycloalkyl, heterocyclyl, aryl and heteroaryl are each optionally substituted by one or more groups selected from the group consisting of deuterium, alkyl, haloalkyl, halogen, amino, nitro, cyano, hydroxy, alkoxy, haloalkoxy, hydroxyalkyl, cycloalkyl, heterocyclyl, aryl and heteroaryl;
or two $R^2$ are taken together to form a cycloalkyl or heterocyclyl, wherein the cycloalkyl or heterocyclyl is each optionally substituted by one or more groups selected from the group consisting of alkyl, haloalkyl, halogen, amino, nitro, cyano, hydroxy, alkoxy, haloalkoxy, hydroxyalkyl, cycloalkyl, heterocyclyl, aryl and heteroaryl;
$R^3$ is selected from the group consisting of hydrogen, alkyl, deuterated alkyl, amino, alkoxy, hydroxyalkyl, cycloalkyl, heterocyclyl, aryl and heteroaryl, wherein the alkyl, cycloalkyl, heterocyclyl, aryl and heteroaryl are each optionally substituted by one or more groups selected from the group consisting of alkyl, halogen, hydroxy, amino, nitro, cyano, alkoxy, hydroxyalkyl, cycloalkyl, heterocyclyl, aryl and heteroaryl;
$R^4$ and $R^5$ are each independently selected from the group consisting of hydrogen, alkyl, alkoxy, hydroxyalkyl, hydroxy, amino, alkoxycarbonyl, cycloalkyl, heterocyclyl, aryl and heteroaryl, wherein the alkyl, cycloalkyl, heterocyclyl, aryl and heteroaryl are each optionally substituted by one or more groups selected from the group consisting of alkyl, halogen, hydroxy, amino, alkoxycarbonyl, nitro, cyano, alkoxy, hydroxyalkyl, cycloalkyl, heterocyclyl, aryl and heteroaryl;
p and q are each independently 0, 1, 2, 3 or 4; and
m is 0, 1 or 2.

In a preferred embodiment of the present invention, a compound of formula (I-A), or a tautomer, mesomer, racemate, enantiomer, diastereomer thereof, or mixture thereof, or a pharmaceutically acceptable salt thereof, is a compound of formula (I):

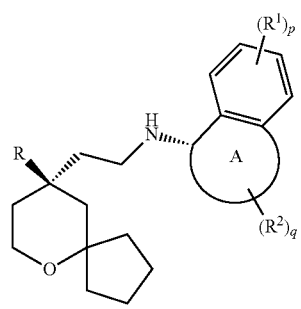

(I)

or a tautomer, mesomer, racemate, enantiomer, diastereomer thereof, or mixture thereof, or a pharmaceutically acceptable salt thereof,
wherein:
ring A, R, $R^1$, $R^2$, p and q are as defined in formula (I-A).

In a preferred embodiment of the present invention, in a compound of formula (I) or formula (I-A), or a tautomer, mesomer, racemate, enantiomer, diastereomer thereof, or mixture thereof, or a pharmaceutically acceptable salt thereof, ring A is selected from the group consisting of 5 to 6 membered heterocyclyl and 5 to 6 membered cycloalkyl.

In a preferred embodiment of the present invention, in a compound of formula (I) or formula (I-A), or a tautomer, mesomer, racemate, enantiomer, diastereomer thereof, or mixture thereof, or a pharmaceutically acceptable salt thereof, R is pyridyl.

In a preferred embodiment of the present invention, in a compound of formula (I) or formula (I-A), or a tautomer, mesomer, racemate, enantiomer, diastereomer thereof, or mixture thereof, or a pharmaceutically acceptable salt thereof, each $R^1$ is identical or different and each is independently selected from the group consisting of hydrogen and halogen.

In a preferred embodiment of the present invention, in a compound of formula (I) or formula (I-A), or a tautomer, mesomer, racemate, enantiomer, diastereomer thereof, or mixture thereof, or a pharmaceutically acceptable salt thereof, each $R^2$ is identical or different and each is independently selected from the group consisting of hydrogen, alkyl, oxo, alkoxy, hydroxy, halogen and —$OR^3$, wherein the alkyl and alkoxy are each optionally substituted by one or more groups selected from the group consisting of deuterium, alkyl, halogen, hydroxy, amino, alkoxycarbonyl, nitro, cyano, alkoxy, hydroxyalkyl, cycloalkyl, heterocyclyl, aryl and heteroaryl; and $R^3$ is selected from the group consisting of hydrogen, alkyl and cycloalkyl, wherein the alkyl is optionally substituted by halogen or cycloalkyl.

In a preferred embodiment of the present invention, a compound of formula (I-A), or a tautomer, mesomer, racemate, enantiomer, diastereomer thereof, or mixture thereof, or a pharmaceutically acceptable salt thereof, is a compound of formula (II-A),

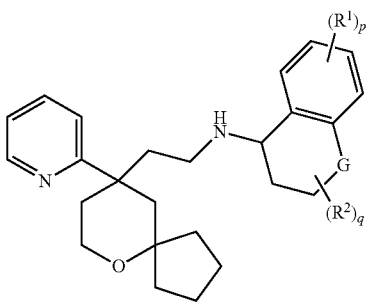

(II-A)

or a tautomer, mesomer, racemate, enantiomer, diastereomer thereof, or mixture thereof, or a pharmaceutically acceptable salt thereof,
wherein:
G is selected from the group consisting of a bond, $CR^aR^b$, C=O, $NR^4$ and oxygen;
$R^a$ and $R^b$ are each independently selected from the group consisting of hydrogen, alkyl, alkoxy, haloalkyl, halogen, amino, nitro, hydroxy, cyano, cycloalkyl, heterocyclyl, aryl, heteroaryl, —$OR^3$, —$C(O)R^3$, —$C(O)OR^3$, —$S(O)_mR^3$ and —$NR^4R^5$, wherein the alkyl, haloalkyl, cycloalkyl, heterocyclyl, aryl and heteroaryl are each optionally substituted by one or more groups selected from the group consisting of alkyl, haloalkyl, halogen, amino, nitro, cyano, hydroxy, alkoxy, haloalkoxy, hydroxyalkyl, cycloalkyl, heterocyclyl, aryl and heteroaryl, preferably hydroxy or —$OR^3$;
or $R^a$ and $R^b$ are taken together to form a cycloalkyl or heterocyclyl, wherein the cycloalkyl or heterocyclyl is each optionally substituted by one or more groups selected from the group consisting of alkyl, haloalkyl, halogen, amino, nitro, cyano, hydroxy, alkoxy, haloalkoxy, hydroxyalkyl, cycloalkyl, heterocyclyl, aryl and heteroaryl; and
$R^1$ to $R^5$, p, m and q are as defined in formula (I-A).

In a preferred embodiment of the present invention, a compound of formula (II-A), or a tautomer, mesomer, racemate, enantiomer, diastereomer thereof, or mixture thereof, or a pharmaceutically acceptable salt thereof, is a compound of formula (II-B):

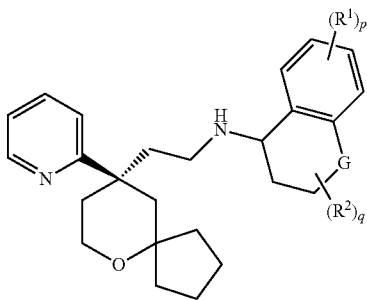

(II-B)

or a tautomer, mesomer, racemate, enantiomer, diastereomer thereof, or mixture thereof, or a pharmaceutically acceptable salt thereof,
wherein:
G is selected from the group consisting of a bond, $CR^aR^b$, C=O, $NR^4$ and oxygen; and
$R^1$, $R^2$, $R^4$, $R^a$, $R^b$, p and q are as defined in formula (II-A).

In a preferred embodiment of the present invention, a compound of formula (II-A), or a tautomer, mesomer, race-mate, enantiomer, diastereomer thereof, or mixture thereof, or a pharmaceutically acceptable salt thereof, is a compound of formula (II):

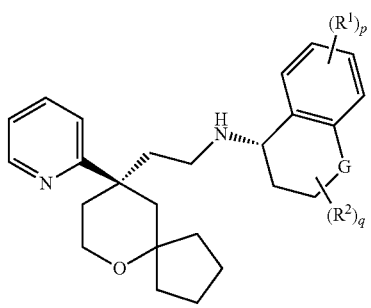

(II)

or a tautomer, mesomer, racemate, enantiomer, diastereomer thereof, or mixture thereof, or a pharmaceutically acceptable salt thereof,
wherein:
G is selected from the group consisting of a bond, $CR^aR^b$, C=O, $NR^4$ and oxygen; and
$R^a$, $R^b$, $R^1$, $R^2$, $R^4$, p and q are as defined in formula (II-A).

In a preferred embodiment of the present invention, a compound of formula (II-A), or a tautomer, mesomer, racemate, enantiomer, diastereomer thereof, or mixture thereof, or a pharmaceutically acceptable salt thereof, is a compound of formula (IV-A):

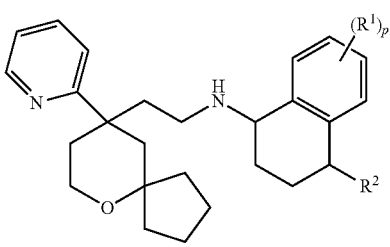

(IV-A)

or a tautomer, mesomer, racemate, enantiomer, diastereomer thereof, or mixture thereof, or a pharmaceutically acceptable salt thereof,
wherein:
$R^1$, $R^2$ and p are as defined in formula (II-A).

In a preferred embodiment of the present invention, a compound of formula (II), or a tautomer, mesomer, racemate, enantiomer, diastereomer thereof, or mixture thereof, or a pharmaceutically acceptable salt thereof, is a compound of formula (IV):

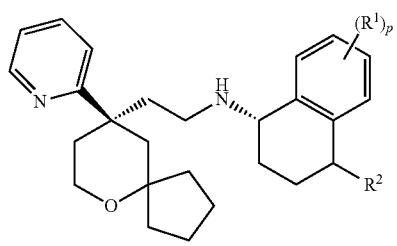

(IV)

or a tautomer, mesomer, racemate, enantiomer, diastereomer thereof, or mixture thereof, or a pharmaceutically acceptable salt thereof.

wherein:

R¹, R² and p are as defined in formula (II).

Exemplary compounds of formula (I-A) include, but are not limited to:

| Example No. | Structure and Name |
|---|---|
| 1 | 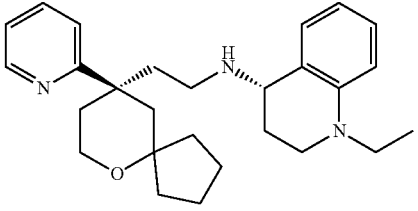<br>(S)-1-ethyl-N-(2-((R)-9-(pyridin-2-yl)-6-oxaspiro[4.5]decan-9-yl)ethyl)-1,2,3,4-tetrahydroquinolin-4-amine<br>1 |
| 2 | 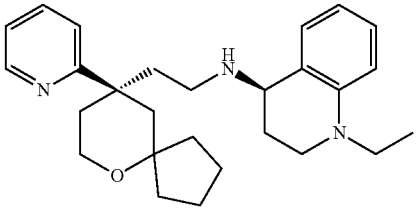<br>(R)-1-ethyl-N-(2-((R)-9-(pyridin-2-yl)-6-oxaspiro[4.5]decan-9-yl)ethyl)-1,2,3,4-tetrahydroquinolin-4-amine<br>2 |
| 3 | 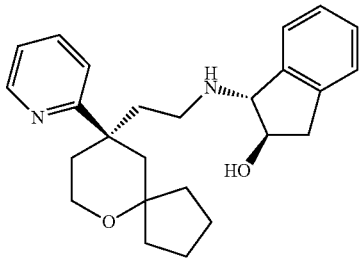<br>(1R,2R)-1-((2-((R)-9-(pyridin-2-yl)-6-oxaspiro[4.5]decan-9-yl)ethyl)amino)-2,3-dihydro-1H-inden-2-ol<br>3 |
| 4 | 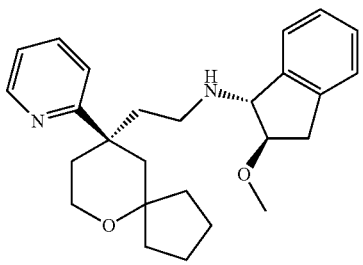<br>(1R,2R)-2-methoxy-N-(2-((R)-9-(pyridin-2-yl)-6-oxaspiro[4.5]decan-9-yl)ethyl)-2,3-dihydro-1H-inden-1-amine<br>4 |

-continued

| Example No. | Structure and Name |
|---|---|
| 5 | 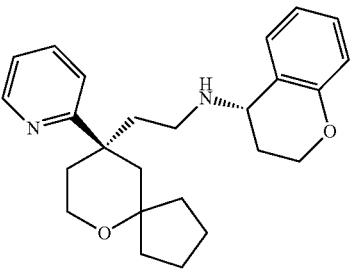<br>5<br>N-(2-((R)-9-(pyridin-2-yl)-6-oxaspiro[4.5]decan-9-yl)ethyl)chroman-4-amine |
| 6 | 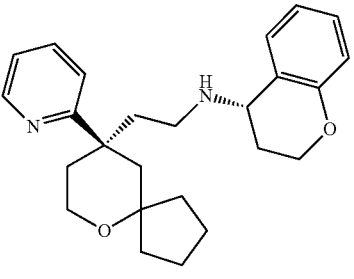<br>6<br>(S)-N-(2-((R)-9-(pyridin-2-yl)-6-oxaspiro[4.5]decan-9-yl)ethyl)chroman-4-amine |
| 7 | 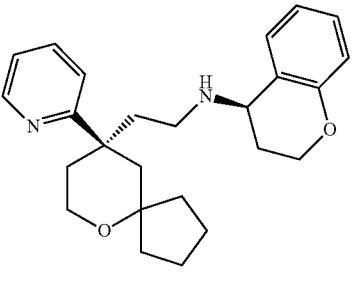<br>7<br>(R)-N-(2-((R)-9-(pyridin-2-yl)-6-oxaspiro[4.5]decan-9-yl)ethyl)chroman-4-amine |
| 8 | 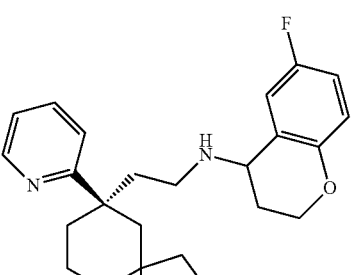<br>8<br>6-fluoro-N-(2-((R)-9-(pyridin-2-yl)-6-oxaspiro[4.5]decan-9-yl)ethyl)chroman-4-amine |

| Example No. | Structure and Name |
|---|---|
| 9 | 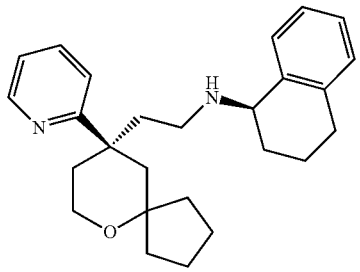

9

(R)-N-(2-((R)-9-(pyridin-2-yl)-6-oxaspiro[4.5]decan-9-yl)ethyl)-1,2,3,4-tetrahydronaphthalen-1-amine |
| 10 | 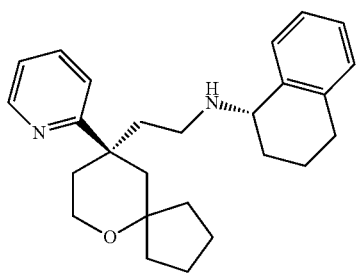

10

(S)-N-(2-((R)-9-(pyridin-2-yl)-6-oxaspiro[4.5]decan-9-yl)ethyl)-1,2,3,4-tetrahydronaphthalen-1-amine |
| 11 | 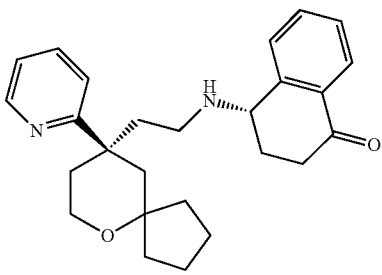

11

(S)-4-((2-((R)-9-(pyridin-2-yl)-6-oxaspiro[4.5]decan-9-yl)ethyl)amino)-3,4-dihydronaphthalen-1(2H)-one |
| 12 | 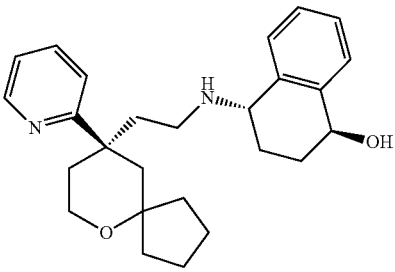

12

(1S,4S)-4-((2-((R)-9-(pyridin-2-yl)-6-oxaspiro[4.5]decan-9-yl)ethyl)amino)-1,2,3,4-tetrahydronaphthalen-1-ol |
| 13 | 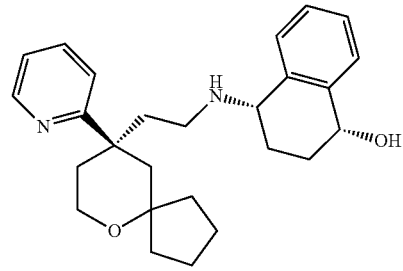

13

(1R,4S)-4-((2-((R)-9-(pyridin-2-yl)-6-oxaspiro[4.5]decan-9-yl)ethyl)amino)-1,2,3,4-tetrahydronaphthalen-1-ol |
| 14 | 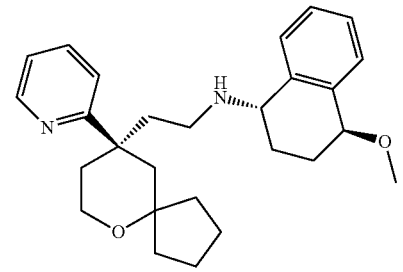

14

(1S,4S)-4-methoxy-N-(2-((R)-9-(pyridin-2-yl)-6-oxaspiro[4.5]decan-9-yl)ethyl)-1,2,3,4-tetrahydronaphthalen-1-amine |
| 15 | 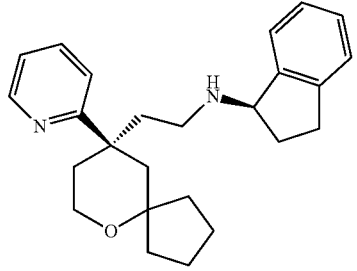

15

(R)-N-(2-((R)-9-(pyridin-2-yl)-6-oxaspiro[4.5]decan-9-yl)ethyl)-2,3-dihydro-1H-inden-1-amine |
| 16 | 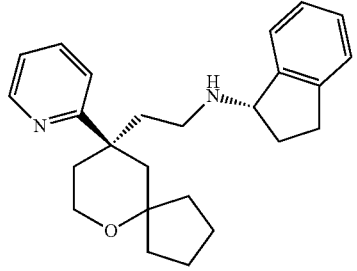

16

(S)-N-(2-((R)-9-(pyridin-2-yl)-6-oxaspiro[4.5]decan-9-yl)ethyl)-2,3-dihydro-1H-inden-1-amine |

-continued

| Example No. | Structure and Name |
|---|---|
| 17 | 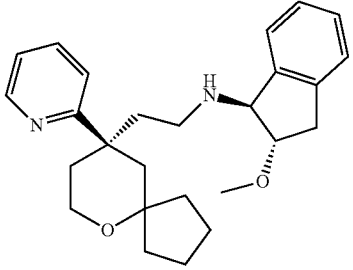<br><br>17<br><br>(1S,2S)-2-methoxy-N-(2-((R)-9-(pyridin-2-yl)-6-oxaspiro[4.5]decan-9-yl)ethyl)-2,3-dihydro-1H-inden-1-amine |
| 18 | 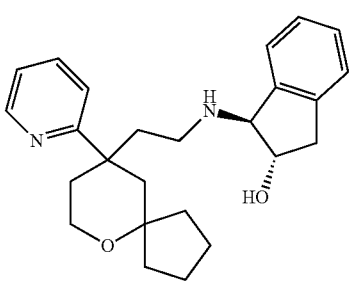<br><br>18<br><br>(1S,2S)-1-((2-(9-(pyridin-2-yl)-6-oxaspiro[4.5]decan-9-yl)ethyl)amino)-2,3-dihydro-1H-inden-2-ol |
| 19 | 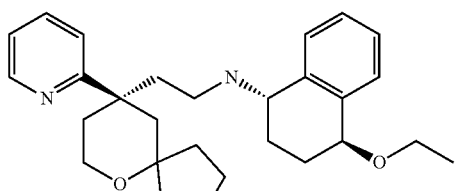<br><br>19<br><br>(1S,4S)-4-ethoxy-N-(2-((R)-9-(pyridin-2-yl)-6-oxaspiro[4.5]decan-9-yl)ethyl)-1,2,3,4-tetrahydronaphthalen-1-amine |
| 20 | 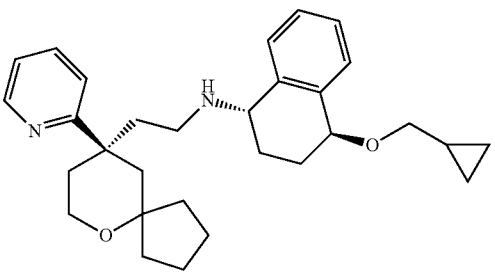<br><br>20<br><br>(1S,4S)-4-(cyclopropylmethoxy)-N-(2-((R)-9-(pyridin-2-yl)-6-oxaspiro[4.5]decan-9-yl)ethyl)-1,2,3,4-tetrahydronaphthalen-1-amine |

-continued

| Example No. | Structure and Name |
|---|---|
| 21 | 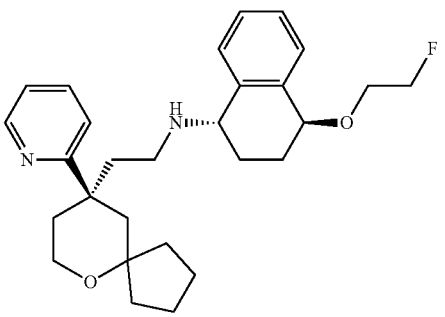<br><br>21<br><br>(1S,4S)-4-(2-fluoroethoxy)-N-(2-((R)-9-(pyridin-2-yl)-6-oxaspiro[4.5]decan-9-yl)ethyl)-1,2,3,4-tetrahydronaphthalen-1-amine |
| 22 | 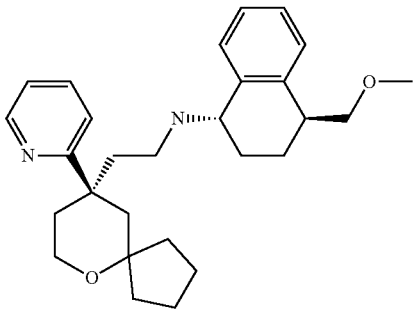<br><br>22<br><br>(1S,4S)-4-(methoxymethyl)-N-(2-((R)-9-(pyridin-2-yl)-6-oxaspiro[4.5]decan-9-yl)ethyl)-1,2,3,4-tetrahydronaphthalen-1-amine |
| 23 | 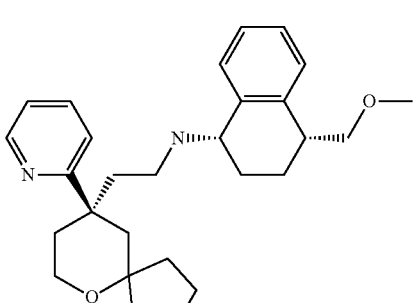<br><br>23<br><br>(1S,4R)-4-(methoxymethyl)-N-(2-((R)-9-(pyridin-2-yl)-6-oxaspiro[4.5]decan-9-yl)ethyl)-1,2,3,4-tetrahydronaphthalen-1-amine |

| Example No. | Structure and Name |
|---|---|
| 24 | 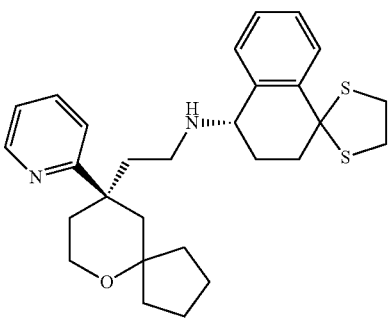<br>(S)-N-(2-((R)-9-(pyridin-2-yl)-6-oxaspiro[4.5]decan-9-yl)ethyl)-3',4'-dihydro-2'H-spiro[[1,3]dithiolane-2,1'-naphthalen]-4'-amine<br>24 |
| 25 | 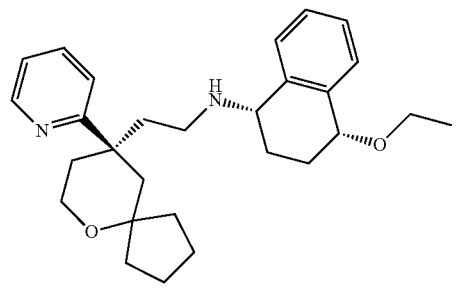<br>(1S,4R)-4-ethoxy-N-(2-((R)-9-(pyridin-2-yl)-6-oxaspiro[4.5]decan-9-yl)ethyl)-1,2,3,4-tetrahydronaphthalen-1-amine<br>25 |
| 26 | 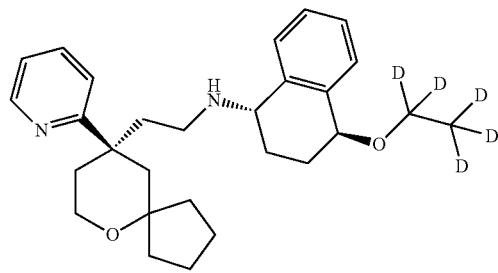<br>(1S,4S)-4-(ethoxy-d₅)-N-(2-((R)-9-(pyridin-2-yl)-6-oxaspiro[4.5]decan-9-yl)ethyl)-1,2,3,4-tetrahydronaphthalen-1-amine<br>26 |
| 27 | 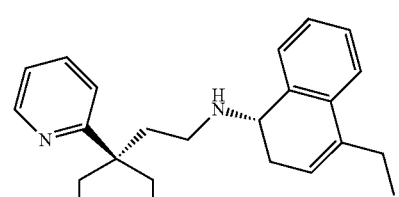<br>(S)-4-ethyl-N-(2-((R)-9-(pyridin-2-yl)-6-oxaspiro[4.5]decan-9-yl)ethyl)-1,2-dihydronaphthalen-1-amine<br>27 |
| 28 | 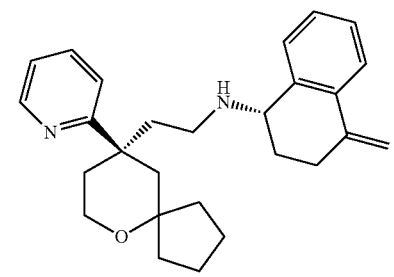<br>(S)-4-methylene-N-(2-((R)-9-(pyridin-2-yl)-6-oxaspiro[4.5]decan-9-yl)ethyl)-1,2,3,4-tetrahydronaphthalen-1-amine<br>28 |
| 29 | 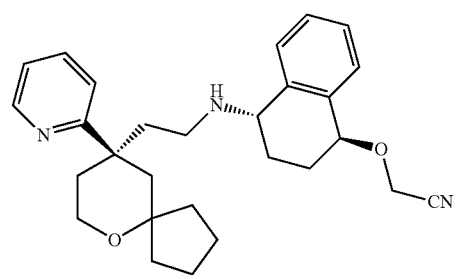<br>2-(((1S,4S)-4-((2-((R)-9-(pyridin-2-yl)-6-oxaspiro[4.5]decan-9-yl)ethyl)amino)-1,2,3,4-tetrahydronaphthalen-1-yl)oxy)acetonitrile<br>29 |

| Example No. | Structure and Name |
|---|---|
| 30 | 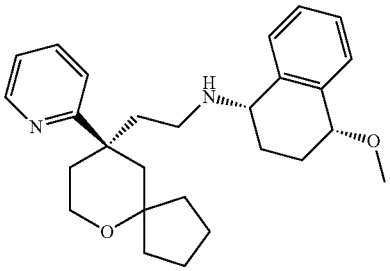

30

(1S,4R)-4-methoxy-N-(2-((R)-9-(pyridin-2-yl)-6-oxaspiro[4.5]
decan-9-yl)ethyl)-1,2,3,4-tetrahydronaphthalen-1-amine
30 |
| 31 | 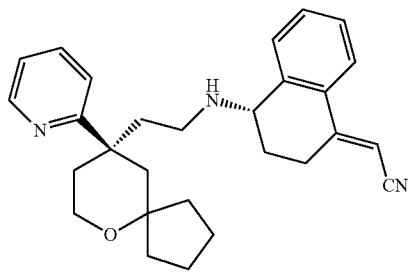

31

2-((S,E)-4-((2-((R)-9-(pyridin-2-yl)-6-oxaspiro[4.5]decan-9-
yl)ethyl)amino)-3,4-dihydro-naphthalen-1(2H)-ylidene)
acetonitrile
31 |
| 32 | 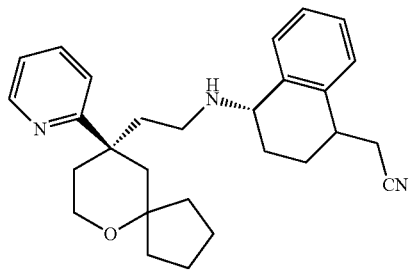

32

2-((4S)-4-((2-((R)-9-(pyridin-2-yl)-6-oxaspiro[4.5]decan-9-yl)
ethyl)amino)-1,2,3,4-tetrahydro-naphthalen-1-yl)acetonitrile
32 |
| 33 | 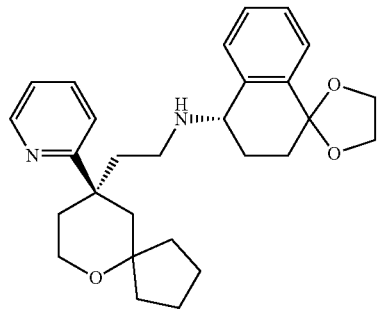

33

(S)-N-(2-((R)-9-(pyridin-2-yl)-6-oxaspiro[4.5]decan-9-yl)ethyl)-
3,4-dihydro-2H-spiro[naphthalen-1,2'-[1,3]dioxolane]-4-amine
33 |
| 34 | 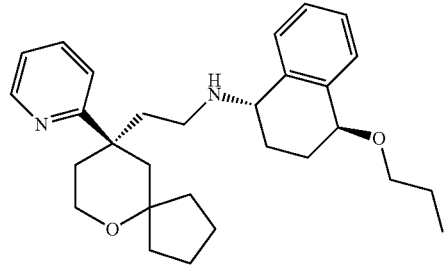

34

(1S,4S)-4-propoxy-N-(2-((R)-9-(pyridin-2-yl)-6-oxaspiro[4.5]
decan-9-yl)ethyl)-1,2,3,4-tetrahydronaphthalen-1-amine
34 | or a tautomer, mesomer, racemate, enantiomer, diastereomer thereof, or mixture thereof, or a pharmaceutically acceptable salt thereof.

In another aspect, the present invention is also directed to a process for preparing a compound of formula (I-A), or a tautomer, mesomer, racemate, enantiomer, diastereomer thereof, or mixture thereof, or a pharmaceutically acceptable salt thereof, comprising a step of:

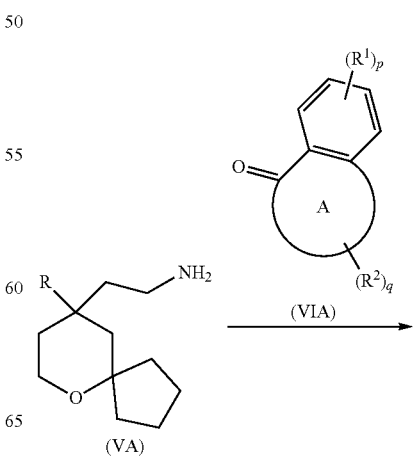

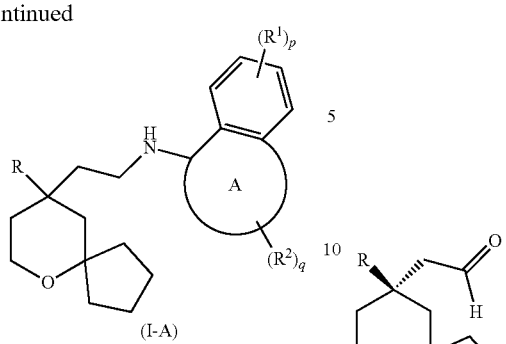

(I-A)

reacting a compound of formula (VA) or a hydrochloride thereof with a compound of formula (VIA) via a reductive amination to obtain the compound of formula (I-A);

wherein:

ring A, R, $R^1$, $R^2$, p and q are as defined in formula (I-A).

In another aspect, the present invention is also directed to a process for preparing the compound of formula (I-A), or a tautomer, mesomer, racemate, enantiomer, diastereomer thereof, or mixture thereof, or a pharmaceutically acceptable salt thereof, comprising a step of:

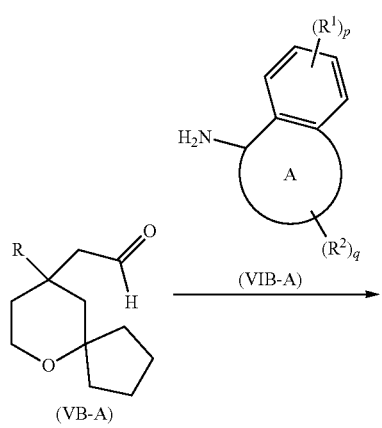

(VB-A)

reacting a compound of formula (VB-A) with a compound of formula (VIB-A) or a hydrochloride thereof via a reductive amination to obtain the compound of formula (I-A);

wherein:

ring A, R, $R^1$, $R^2$, p and q are as defined in formula (I-A).

In another aspect, the present invention is also directed to a process for preparing the compound of formula (I), or a tautomer, mesomer, racemate, enantiomer, diastereomer thereof, or mixture thereof, or a pharmaceutically acceptable salt thereof, comprising a step of:

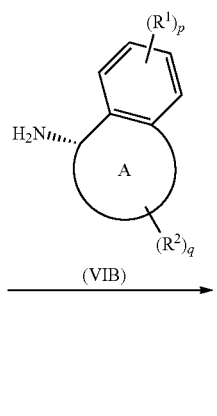

(VB)

(I)

reacting a compound of formula (VB) with a compound of formula (VIB) or a hydrochloride thereof via a reductive amination to obtain the compound of formula (I);

wherein:

ring A, R, $R^1$, $R^2$, p and q are as defined in formula (I).

In another aspect, the present invention is also directed to a pharmaceutical composition comprising a therapeutically effective amount of the compound of each of the aforementioned formulas, or a tautomer, mesomer, racemate, enantiomer, diastereomer thereof, or mixture thereof, or a pharmaceutically acceptable salt thereof, and one or more pharmaceutically acceptable carriers, diluents or excipients. The present invention is also directed to a process for the preparation of the aforementioned composition comprising a step of mixing a compound represented by each formula or a tautomer, mesomer, racemate, enantiomer, diastereomer thereof, or mixture thereof, or a pharmaceutically acceptable salt thereof, with one or more pharmaceutically acceptable carriers, diluents or excipients.

The present invention is further directed to use of a compound of each formula, particularly formula (I), or a tautomer, mesomer, racemate, enantiomer, diastereomer thereof, or mixture thereof, or a pharmaceutically acceptable salt thereof, or a pharmaceutical composition comprising the same, in the preparation of a medicament for agonizing or antagonizing MOR receptor.

The present invention is further directed to use of a compound of each formula, particularly formula (I), or a tautomer, mesomer, racemate, enantiomer, diastereomer thereof, or mixture thereof, or a pharmaceutically acceptable salt thereof, or a pharmaceutical composition comprising the same, in the preparation of a medicament for preventing and/or treating an MOR agonist receptor mediated and related disease, wherein the disease is selected from the group consisting of pain, immune dysfunction, inflammation, esophageal reflux, neurological and psychiatric disorders, urinary and reproductive diseases, cardiovascular diseases and respiratory diseases.

The present invention is further directed to use of a compound of each formula, particularly formula (I), or a tautomer, mesomer, racemate, enantiomer, diastereomer thereof, or mixture thereof, or a pharmaceutically acceptable salt thereof, or a pharmaceutical composition comprising the same, in the preparation of a medicament for preventing and/or treating pain and pain-related diseases in mammals, wherein the pain can be postoperative pain, cancer-induced pain, neuropathic pain, traumatic pain and inflammatory pain, etc., wherein the cancer can be selected from the group consisting of breast cancer, endometrial cancer, cervical cancer, skin cancer, prostate cancer, ovarian cancer, fallopian tube tumor, ovarian tumor, hemophilia and leukemia.

The present invention is also directed to a method for preventing and/or treating an MOR agonist receptor mediated and related disease, comprising a step of administering to a patient in need thereof a therapeutically effective amount of a compound of each formula, particularly formula (I), or a tautomer, mesomer, racemate, enantiomer, diastereomer, or mixture thereof, or a pharmaceutically acceptable salt thereof. This method shows prominent efficacy and fewer side effects. The disease is selected from the group consisting of pain, immune dysfunction, inflammation, esophageal reflux, neurological and psychiatric disorders, urinary and reproductive diseases, cardiovascular diseases and respiratory diseases; preferably pain.

In another aspect, the present invention is directed to a method for preventing and/or treating pain and pain-related diseases in mammals, comprising a step of administering to a patient in need thereof a therapeutically effective amount of a compound of each formula, particularly formula (I), or a tautomer, mesomer, racemate, enantiomer, diastereomer, or mixture thereof, or a pharmaceutically acceptable salt thereof. This method shows prominent efficacy and fewer side effects. The pain can be postoperative pain, cancer-induced pain, neuropathic pain, traumatic pain and inflammatory pain; and the cancer can be selected from the group consisting of breast cancer, endometrial cancer, cervical cancer, skin cancer, prostate cancer, ovarian cancer, fallopian tube tumor, ovarian tumor, hemophilia and leukemia.

The present invention is directed to a compound of each formula, particularly formula (I) or a tautomer, mesomer, racemate, enantiomer, diastereomer, or mixture thereof, or a pharmaceutically acceptable salt thereof, or a pharmaceutical composition comprising the same for use as a medicament for the treatment of immune dysfunction, inflammation, esophageal reflux, neurological and psychiatric disorders, urinary and reproductive disorders, drug and alcohol abuse, gastritis and diarrhea, cardiovascular diseases, respiratory diseases and cough.

Pharmaceutical compositions containing the active ingredient can be in a form suitable for oral administration, for example, a tablet, troche, lozenge, aqueous or oily suspension, dispersible powder or granule, emulsion, hard or soft capsule, or syrup or elixir. Oral compositions can be prepared according to any method known in the art for the preparation of pharmaceutical compositions. Such compositions can contain one or more agents selected from the group consisting of sweetening agents, flavoring agents, colorants and preservatives, in order to provide a pleasing and palatable pharmaceutical formulation. The tablet contains the active ingredient in admixture with non-toxic pharmaceutically acceptable excipients suitable for the manufacture of a tablet.

Oral formulations can be provided as hard gelatin capsules in which the active ingredient is mixed with an inert solid diluent, such as calcium carbonate, calcium phosphate or kaolin, or as soft gelatin capsules in which the active ingredient is mixed with an a water-soluble carrier, such as polyethyleneglycol, or an oil medium, such as peanut oil, liquid paraffin or olive oil.

An aqueous suspension contains the active ingredient in admixture with excipients suitable for the manufacture of an aqueous suspension.

The active ingredient in admixture with the dispersing or wetting agents, suspending agent or one or more preservatives can be prepared as a dispersible powder or granule suitable for the preparation of an aqueous suspension by adding water.

Suitable dispersant or wetting agents and suspending agents are exemplified by those already mentioned above. Additional excipients, such as sweetening, flavoring, and coloring agents, can also be added. These compositions can be preserved by adding an antioxidant, such as ascorbic acid.

The present pharmaceutical composition can also be in the form of an oil-in-water emulsion.

The pharmaceutical composition of the present invention can be in the form of a sterile aqueous solution. Acceptable vehicles or solvents that can be used are water, Ringer's solution and isotonic sodium chloride solution.

The pharmaceutical composition can be in the form of a sterile injectable aqueous or oily suspension for intramuscular and subcutaneous administration.

It is well known to those skilled in the art that the dosage of a drug depends on a variety of factors including, but not limited to, the following factors: activity of a specific compound, age of the patient, weight of the patient, general health of the patient, behavior of the patient, diet of the patient, administration time, administration route, excretion rate, drug combination and the like. In addition, the best treatment, such as treatment mode, daily dose of the compound of formula (I) or the type of pharmaceutically acceptable salt thereof can be verified by traditional therapeutic regimens.

DETAILED DESCRIPTION OF THE INVENTION

Unless otherwise stated, the terms used in the specification and claims have the meanings described below.

"Alkyl" refers to a saturated aliphatic hydrocarbon group including $C_1$ to $C_{20}$ straight chain and branched chain groups, preferably an alkyl having 1 to 12 carbon atoms, and more preferably an alkyl having 1 to 6 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and branched isomers thereof. More preferably, an alkyl group is a lower alkyl having 1 to 6 carbon atoms, and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, and the like. The alkyl group can be substituted or unsubstituted. When substituted, the substituent group(s) can be substituted at any available connection point. The substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclic alkylthio, oxo, carboxy, and alkoxycarbonyl.

"Alkenyl" refers to an alkyl as defined above that has at least two carbon atoms and at least one carbon-carbon double bond, for example, ethenyl, 1-propenyl, 2-propenyl, 1-, 2- or 3-butenyl and the like. The alkenyl group can be substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio and heterocyclic alkylthio.

"Cycloalkyl" refers to a saturated or partially unsaturated monocyclic or polycyclic hydrocarbon group having 3 to 20 carbon atoms, preferably 3 to 12 carbon atoms, more preferably 3 to 6 carbon atoms, and most preferably 5 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl, and the like. Polycyclic cycloalkyl includes a cycloalkyl having a spiro ring, fused ring or bridged ring.

"Spiro cycloalkyl" refers to a 5 to 20 membered polycyclic group with rings connected through one common carbon atom (called a spiro atom), wherein one or more rings can contain one or more double bonds, but none of the rings has a completely conjugated pi-electron system, preferably 6 to 14 membered spiro cycloalkyl, and more preferably 7 to 10 membered spiro cycloalkyl. According to the number of the spiro atoms shared between the rings, spiro cycloalkyl can be divided into mono-spiro cycloalkyl, di-spiro cycloalkyl, or poly-spiro cycloalkyl, and preferably a mono-spiro cycloalkyl or di-spiro cycloalkyl, and more preferably 4-membered/4-membered, 4-membered/5-membered, 4-membered/6-membered, 5-membered/5-membered, or 5-membered/6-membered mono-spiro cycloalkyl. Non-limiting examples of spiro cycloalkyls include:

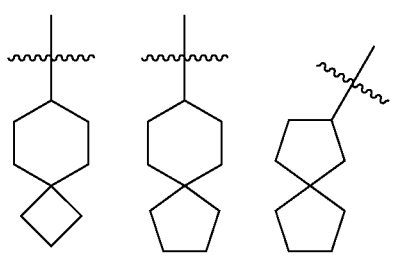

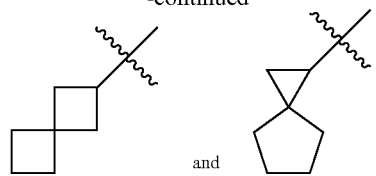

and

"Fused cycloalkyl" refers to a 5 to 20 membered all-carbon polycyclic group, wherein each ring in the system shares an adjacent pair of carbon atoms with another ring, wherein one or more rings can contain one or more double bonds, but none of the rings has a completely conjugated pi-electron system, preferably 6 to 14 membered fused cycloalkyl, and more preferably 7 to 10 membered fused cycloalkyl. According to the number of membered rings, fused cycloalkyl can be divided into bicyclic, tricyclic, tetracyclic or polycyclic fused cycloalkyl, preferably bicyclic, or tricyclic fused cycloalkyl, and more preferably 5-membered/5-membered, or 5-membered/6-membered bicyclic fused cycloalkyl. Non-limiting examples of fused cycloalkyl include:

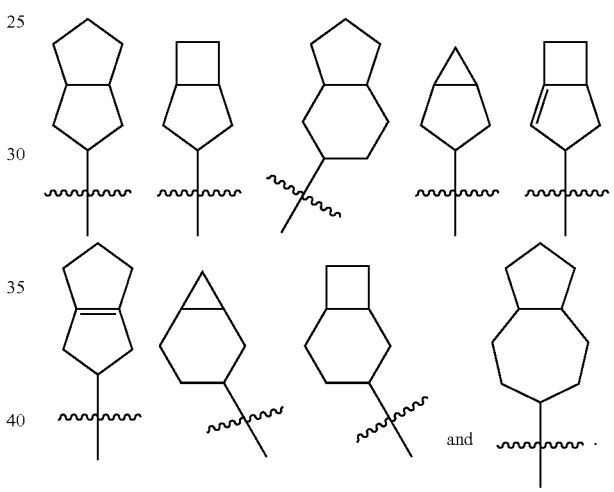

and

"Bridged cycloalkyl" refers to a 5 to 20 membered all-carbon polycyclic group, wherein every two rings in the system share two disconnected carbon atoms, wherein the rings can have one or more double bonds, but none of the rings has a completely conjugated pi-electron system, preferably 6 to 14 membered bridged cycloalkyl, and more preferably 7 to 10 membered bridged cycloalkyl. According to the number of membered rings, bridged cycloalkyl can be divided into bicyclic, tricyclic, tetracyclic or polycyclic bridged cycloalkyl, preferably bicyclic, tricyclic or tetracyclic bridged cycloalkyl, and more preferably bicyclic or tricyclic bridged cycloalkyl. Non-limiting examples of bridged cycloalkyls include:

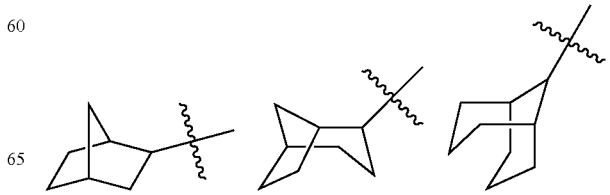

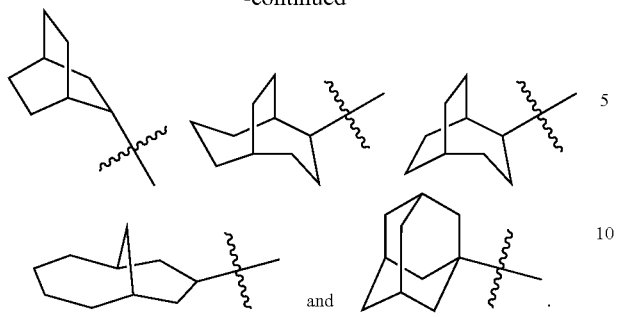

The ring of cycloalkyl can be fused to the ring of aryl, heteroaryl or heterocyclyl, wherein the ring bound to the parent structure is cycloalkyl. Non-limiting examples include indanyl, tetrahydronaphthyl, benzocycloheptyl and the like, preferably benzocyclopentyl, or tetrahydronaphthyl. The cycloalkyl can be optionally substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclic alkylthio, oxo, carboxy and alkoxycarbonyl.

"Heterocyclyl" refers to a 3 to 20 membered saturated or partially unsaturated monocyclic or polycyclic hydrocarbon group having one or more heteroatoms selected from the group consisting of N, O, and $S(O)_m$ (wherein m is an integer of 0 to 2) as ring atoms, but excluding —O—O—, —O—S— and —S—S— in the ring, with the remaining ring atoms being carbon atoms. Preferably, heterocyclyl has 3 to 12 atoms, wherein 1 to 4 atoms are heteroatoms, more preferably 3 to 8 atoms, wherein 1 to 3 atoms are heteroatoms, and most preferably 5 to 6 atoms, wherein 1 to 2 or 1 to 3 atoms are heteroatoms. Non-limiting examples of monocyclic heterocyclyl include pyrrolidinyl, imidazolidinyl, tetrahydrofuranyl, tetrahydropyranyl, tetrahydrothienyl, dihydroimidazolyl, dihydrofuranyl, dihydropyrazolyl, dihydropyrrolyl, piperidyl, piperazinyl, morpholinyl, thiomorpholinyl, homopiperazinyl and the like, preferably tetrahydropyranyl, piperidyl or pyrrolidinyl. Polycyclic heterocyclyl includes a heterocyclyl having a spiro ring, fused ring or bridged ring.

"Spiro heterocyclyl" refers to a 5 to 20 membered polycyclic heterocyclyl with rings connected through one common atom (called a spiro atom), wherein the rings have one or more heteroatoms selected from the group consisting of N, O, and $S(O)_m$ (wherein m is an integer of 0 to 2) as ring atoms, with the remaining ring atoms being carbon atoms, wherein one or more rings can contain one or more double bonds, but none of the rings has a completely conjugated pi-electron system, preferably 6 to 14 membered spiro heterocyclyl, and more preferably 7 to 10 membered spiro heterocyclyl. According to the number of the spiro atoms shared between the rings, spiro heterocyclyl can be divided into mono-spiro heterocyclyl, di-spiro heterocyclyl, or polyspiro heterocyclyl, preferably mono-spiro heterocyclyl or di-spiro heterocyclyl, and more preferably 4-membered/4-membered, 4-membered/5-membered, 4-membered/6-membered, 5-membered/5-membered, or 5-membered/6-membered mono-spiro heterocyclyl. Non-limiting examples of spiro heterocyclyls include:

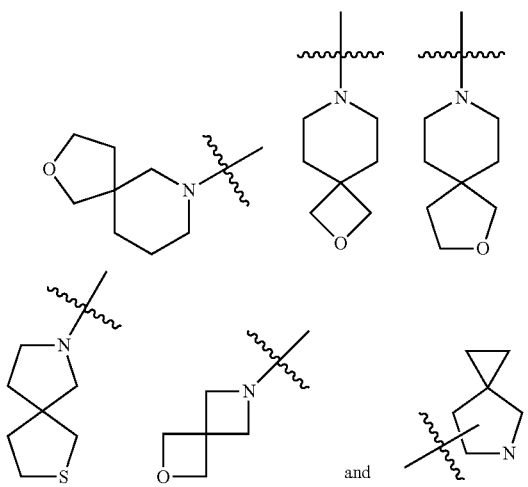

"Fused heterocyclyl" refers to a 5 to 20 membered polycyclic heterocyclyl group, wherein each ring in the system shares an adjacent pair of atoms with another ring, wherein one or more rings can contain one or more double bonds, but none of the rings has a completely conjugated pi-electron system, and wherein the rings have one or more heteroatoms selected from the group consisting of N, O, and $S(O)_m$ (wherein m is an integer of 0 to 2) as ring atoms, with the remaining ring atoms being carbon atoms; preferably 6 to 14 membered fused heterocyclyl, and more preferably 7 to 10 membered fused heterocyclyl. According to the number of membered rings, fused heterocyclyl can be divided into bicyclic, tricyclic, tetracyclic or polycyclic fused heterocyclyl, preferably bicyclic or tricyclic fused heterocyclyl, and more preferably 5-membered/5-membered, or 5-membered/6-membered bicyclic fused heterocyclyl. Non-limiting examples of fused heterocyclyl include:

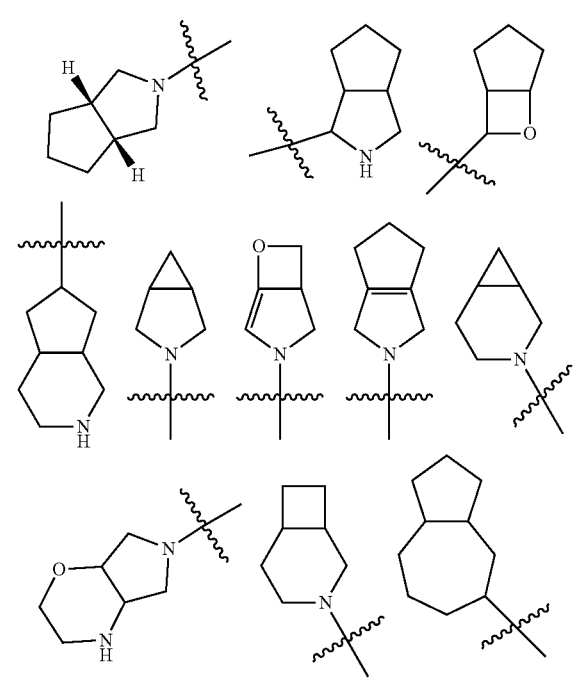

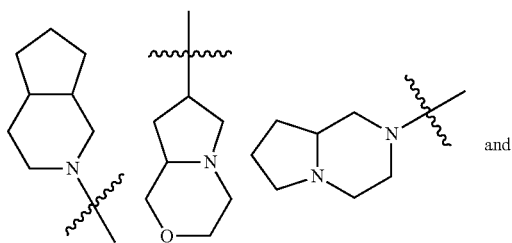

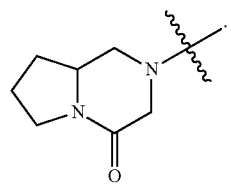

"Bridged heterocyclyl" refers to a 5 to 14 membered polycyclic heterocyclyl group, wherein every two rings in the system share two disconnected atoms, wherein the rings can have one or more double bonds, but none of the rings has a completely conjugated pi-electron system, and the rings have one or more heteroatoms selected from the group consisting of N, O, and $S(O)_m$ (wherein m is an integer of 0 to 2) as ring atoms, with the remaining ring atoms being carbon atoms, preferably 6 to 14 membered bridged heterocyclyl, and more preferably 7 to 10 membered bridged heterocyclyl. According to the number of membered rings, bridged heterocyclyl can be divided into bicyclic, tricyclic, tetracyclic or polycyclic bridged heterocyclyl, preferably bicyclic, tricyclic or tetracyclic bridged heterocyclyl, and more preferably bicyclic or tricyclic bridged heterocyclyl. Non-limiting examples of bridged heterocylyls include:

The heterocyclyl ring can be fused to the ring of an aryl, heteroaryl or cycloalkyl, wherein the ring bound to the parent structure is heterocyclyl. Non-limiting examples include:

etc.

The heterocyclyl can be optionally substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclic alkylthio, oxo, carboxy, and alkoxycarbonyl.

"Aryl" refers to a 6 to 14 membered all-carbon monocyclic ring or polycyclic fused ring (i.e. each ring in the system shares an adjacent pair of carbon atoms with another ring in the system) having a completely conjugated pi-electron system, preferably 6 to 10 membered aryl, and more preferably 5 to 6 membered aryl, for example, phenyl and naphthyl. The aryl ring can be fused to the ring of heteroaryl, heterocyclyl or cycloalkyl, wherein the ring bound to the parent structure is the aryl ring.

The aryl can be optionally substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclic alkylthio, carboxy, and alkoxycarbonyl.

"Heteroaryl" refers to a 5 to 14 membered heteroaromatic system having 1 to 4 heteroatoms selected from the group consisting of O, S and N as ring atoms, preferably 5 to 10 membered heteroaryl having 1 to 3 heteroatoms, and more preferably 5 or 6 membered heteroaryl having 1 to 2 heteroatoms, for example, imidazolyl, furyl, thienyl, thiazolyl, pyrazolyl, oxazolyl, pyrrolyl, tetrazolyl, pyridyl, pyrimidinyl, thiadiazolyl, pyrazinyl and the like, preferably imidazolyl, pyrazolyl, pyimidinyl or thiazolyl, and more preferably pyrazolyl. The heteroaryl ring can be fused to the ring of an aryl, heterocyclyl or cycloalkyl, wherein the ring bound to the parent structure is heteroaryl ring. Non-limiting examples include:

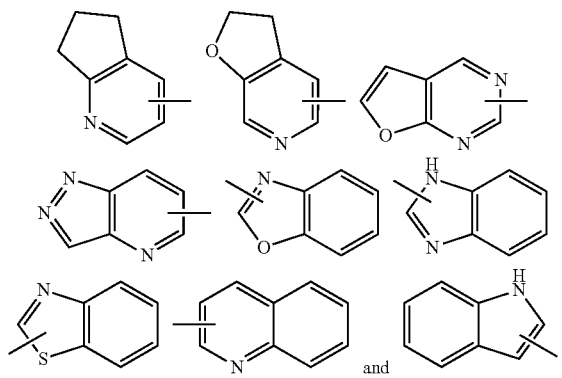

The heteroaryl can be optionally substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclic alkylthio, carboxy and alkoxycarbonyl.

"Alkoxy" refers to an —O-(alkyl) or an —O-(unsubstituted cycloalkyl) group, wherein the alkyl is as defined above. Non-limiting examples include methoxy, ethoxy, propoxy, butoxy, cyclopropyloxy, cyclobutyloxy, cyclopentyloxy, cyclohexyloxy, and the like. The alkoxy can be optionally substituted or unsubstituted. When substituted, the substituent is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclic alkylthio, carboxy, and alkoxycarbonyl.

"Deuterated alkyl" refers to an alkyl substituted by deuterium atom(s), wherein the alkyl is as defined above.

"Hydroxyalkyl" refers to an alkyl substituted by hydroxy(s), wherein the alkyl is as defined above.

"Hydroxy" refers to an —OH group.

"Halogen" refers to fluorine, chlorine, bromine or iodine.

"Amino" refers to an —NH$_2$ group.

"Cyano" refers to a —CN group.

"Nitro" refers to an —NO$_2$ group.

"Carboxy" refers to a —C(O)OH group.

"Alkoxycarbonyl" refers to a —C(O)O(alkyl) or —C(O)O(cycloalkyl) group, wherein the alkyl and cycloalkyl are as defined above.

"Acyl halide" refers to a compound comprising a —C(O)-halogen group.

All of "X is selected from the group consisting of A, B, or C", "X is selected from the group consisting of A, B and C", "X is A, B or C", "X is A, B and C" and the like, are the same meaning. It means that X can be any one or more of A, B, and C. "Optional" or "optionally" means that the event or circumstance described subsequently can, but need not occur, and this description includes the situation in which the event or circumstance does or does not occur. For example, "the heterocyclic group optionally substituted by an alkyl" means that an alkyl group can be, but need not be, present, and this description includes the situation of the heterocyclic group being substituted by an alkyl and the heterocyclic group being not substituted by an alkyl.

"Substituted" refers to one or more hydrogen atoms in a group, preferably up to 5, more preferably 1 to 3 hydrogen atoms, independently substituted by a corresponding number of substituents. It goes without saying that the substituents only exist in their possible chemical positions. The person skilled in the art is able to determine whether the substitution is possible or impossible by experiments or theory without paying excessive efforts. For example, the combination of amino or hydroxy having free hydrogen and carbon atoms having unsaturated bonds (such as olefinic) can be unstable.

A "pharmaceutical composition" refers to a mixture of one or more of the compounds according to the present invention or physiologically/pharmaceutically acceptable salts or prodrugs thereof with other chemical ingredients, and other components such as physiologically/pharmaceutically acceptable carriers and excipients. The purpose of a pharmaceutical composition is to facilitate administration of a compound to an organism, which is conducive to the absorption of the active ingredient, thus displaying biological activity.

A "pharmaceutically acceptable salt" refers to a salt of the compound of the present invention, which is safe and effective in mammals and has the desired biological activity.

Synthesis Method of the Compound of the Present Invention

In order to achieve the object of the present invention, the present invention applies the following technical solutions.

A process for preparing a compound of formula (I-A) of the present invention, or a tautomer, mesomer, racemate, enantiomer, diastereomer thereof, or mixture thereof, or a pharmaceutically acceptable salt thereof, comprises the following step:

Scheme 1

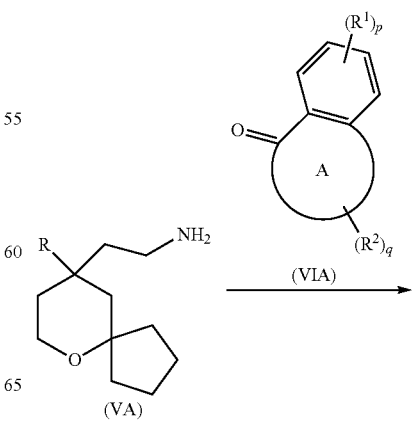

-continued

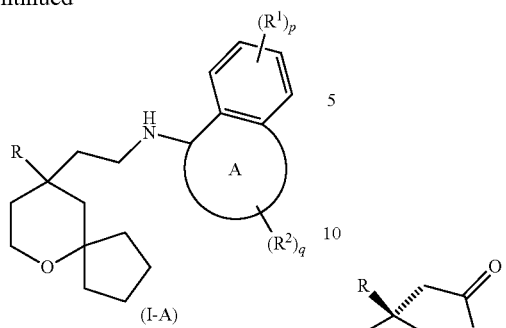

reacting a compound of formula (VA) or a hydrochloride thereof with a compound of formula (VIA) via a reductive amination to obtain the compound of formula (I-A);

wherein:

ring A, R, $R^1$, $R^2$, p and q are as defined in formula (I-A).

The compound of formula (I-A) of the present invention can also be prepared as follows:

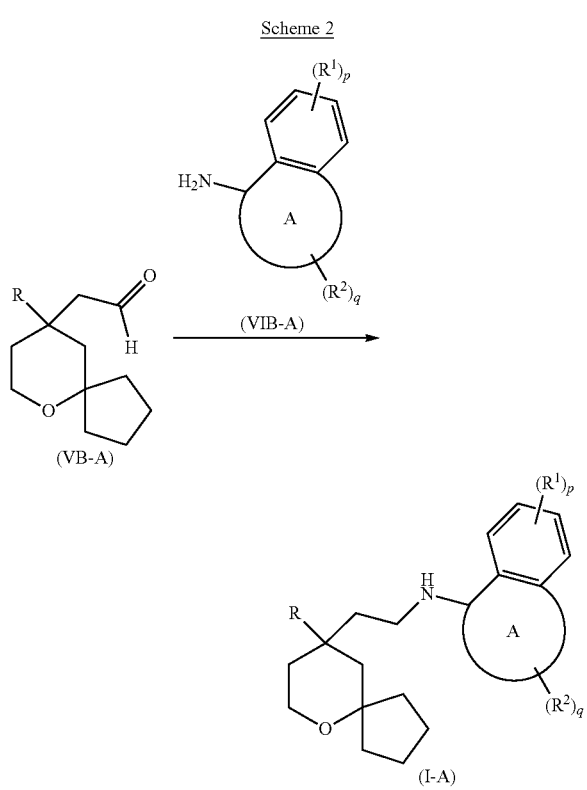

reacting a compound of formula (VB-A) with formula (VIB-A) or a hydrochloride thereof via a reductive amination to obtain the compound of formula (I-A);

wherein:

ring A, R, $R^1$, $R^2$, p and q are as defined in formula (I-A).

In another aspect, the present invention is also directed to a process for preparing the compound of formula (I), or a tautomer, mesomer, racemate, enantiomer, diastereomer thereof, or mixture thereof, or a pharmaceutically acceptable salt thereof, comprising a step of:

Scheme 1

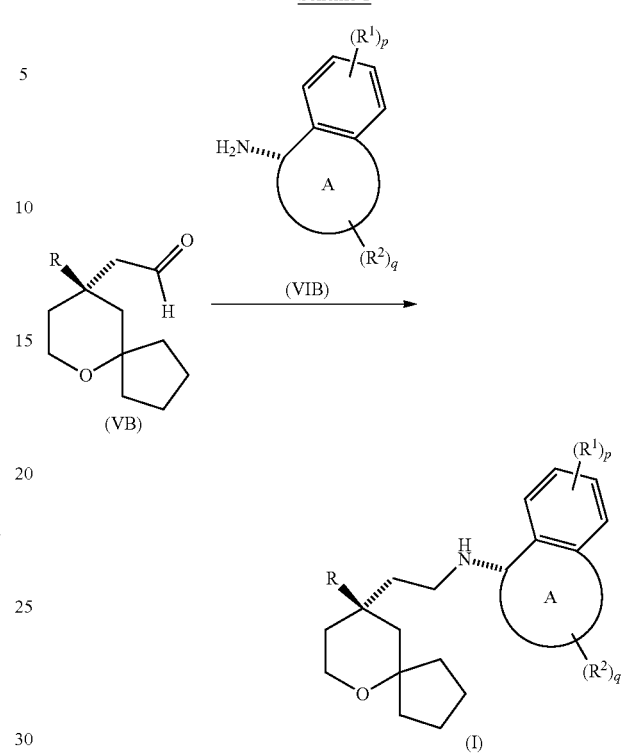

reacting a compound of formula (VB) with a compound of formula (VIB) or a hydrochloride thereof via a reductive amination to obtain the compound of formula (I);

wherein:

ring A, R, $R^1$, $R^2$, p and q are as defined in formula (I).

PREFERRED EMBODIMENTS

The present invention will be further described with reference to the following examples, but the examples should not be considered as limiting the scope of the invention.

EXAMPLES

The structures of the compounds are identified by nuclear magnetic resonance (NMR) and/or mass spectrometry (MS). NMR chemical shifts (δ) are given in $10^{-6}$ (ppm). NMR is determined by a Bruker AVANCE-400 machine. The solvents for determination are deuterated-dimethyl sulfoxide (DMSO-$d_6$), deuterated-chloroform (CDCl$_3$) and deuterated-methanol (CD$_3$OD), and the internal standard is tetramethylsilane (TMS).

MS is determined by a FINNIGAN LCQAd (ESI) mass spectrometer (manufacturer: Thermo, type: Finnigan LCQ advantage MAX).

High performance liquid chromatography (HPLC) is determined on an Agilent 1200DAD high pressure liquid chromatography spectrometer (Sunfire C18 150×4.6 mm chromatographic column) and a Waters 2695-2996 high pressure liquid chromatography spectrometer (Gimini C18 150×4.6 mm chromatographic column).

The average kinase inhibition rates and IC$_{50}$ values are determined by a NovoStar ELISA (BMG Co., Germany).

Yantai Huanghai HSGF254 or Qingdao GF254 silica gel plate is used for thin-layer silica gel chromatography (TLC). The dimension of the silica gel plate used in TLC is 0.15 mm to 0.2 mm, and the dimension of the silica gel plate used in product purification is 0.4 mm to 0.5 mm.

Yantai Huanghai 200 to 300 mesh silica gel is used as a carrier for column chromatography.

The known raw materials of the present invention can be prepared by conventional synthesis methods known in the art, or can be purchased from ABCR GmbH & Co. KG, Acros Organnics, Aldrich Chemical Company, Accela ChemBio Inc., or Dari chemical Company, etc.

Unless otherwise stated, the reactions are carried out under nitrogen atmosphere or argon atmosphere.

The term "nitrogen atmosphere" or "argon atmosphere" means that a reaction flask is equipped with a 1 L nitrogen or argon balloon.

The term "hydrogen atmosphere" means that a reaction flask is equipped with a 1 L hydrogen balloon.

Pressurized hydrogenation reactions are carried out with a Parr 3916EKX hydrogenation instrument and a QL-500 hydrogen generator or HC2-SS hydrogenation instrument.

In hydrogenation reactions, the reaction system is generally vacuumed and filled with hydrogen, and the above operation is repeated three times.

CEM Discover-S 908860 type microwave reactor is used in microwave reactions.

Unless otherwise stated, the solution used in the reactions refers to an aqueous solution.

Unless otherwise stated, the reaction temperature in the reactions refers to room temperature, ranging from 20° C. to 30° C.

The reaction process is monitored by thin layer chromatography (TLC), and the system of developing solvent includes: A: dichloromethane and methanol system, B: n-hexane and ethyl acetate system, C: dichloromethane and acetone system. The ratio of the volume of the solvent can be adjusted according to the polarity of the compounds.

The elution system for purification of the compounds by column chromatography and thin layer chromatography includes: A: dichloromethane and methanol system, B: n-hexane and ethyl acetate system, C: dichloromethane and acetone system. The ratio of the volume of the solvent can be adjusted according to the polarity of the compounds, and sometimes a little alkaline reagent such as triethylamine or acidic reagent such as acetic acid can be added.

Examples 1, 2

(S)-1-ethyl-N-(2-((R)-9-(pyridin-2-yl)-6-oxaspiro [4.5]decan-9-yl)ethyl)-1,2,3,4-tetrahydroquinolin-4-amine 1

(R)-1-ethyl-N-(2-((R)-9-(pyridin-2-yl)-6-oxaspiro [4.5]decan-9-yl)ethyl)-1,2,3,4-tetrahydroquinolin-4-amine 2

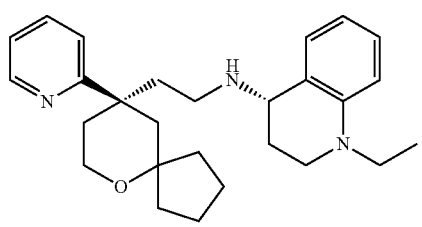

-continued

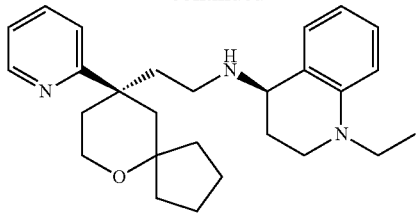

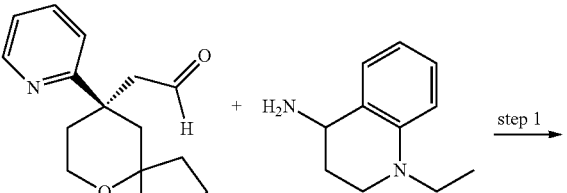

1a    1b

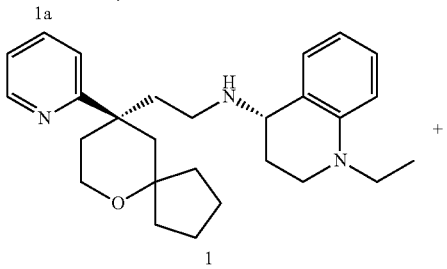

1

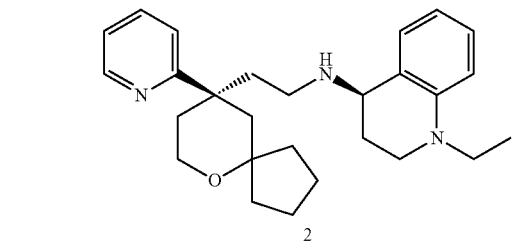

2

(R)-2-(9-(pyridin-2-yl)-6-oxaspiro[4.5]decan-9-yl)acetaldehyde 1a (294 mg, 1.135 mmol, prepared by a method disclosed in International Patent Application Publication "WO2012129495") and 1-ethyl-1,2,3,4-tetrahydroquinolin-4-amine 1b (200 mg, 1.135 mmol, prepared by a method disclosed in International Patent Application Publication "WO2014078454") were dissolved in 15 mL of dichloromethane, and the mixture was stirred for 1 hour. Then, sodium triacetoxyborohydride (1.203 g, 5.675 mmol) was added, and the resulting mixture was stirred for 16 hours. Then, 20 mL of water were added, and the reaction solution was extracted with dichloromethane (20 mL×3). The organic phases were combined, dried over anhydrous sodium sulfate and filtered. The filtrate was concentrated under reduced pressure, and the resulting residue was purified by high performance liquid chromatography to obtain the title compound 1-ethyl-N-(2-((R)-9-(pyridin-2-yl)-6-oxaspiro[4.5] decan-9-yl)ethyl)-1,2,3,4-tetrahydroquinolin-4-amine, which was then separated chirally (separation conditions: chiral preparative column Superchiral S-AD (Chiralway), 2 cm I.D.*25 cm, 5 am; mobile phase:CO$_2$:methanol:diethanolamine=75:25:0.05, flow rate: 50 g/min). The corresponding fractions were collected and concentrated under reduced pressure to give the title compounds 1 (98 mg, a brown oil) and 2 (95 mg, a yellow solid).

Example 1

MS m/z (ESI): 420.3 [M+1];

Chiral HPLC analysis: retention time 4.028 min, chiral purity: 99.7% (chromatographic column: Superchiral S-AD (Chiralway), 0.46 cm I.D.*15 cm, 5 m; mobile phase:$CO_2$: methanol:diethanolamine=75:25:0.05 (v/v/v)); and $^1$H NMR (400 MHz, DMSO-$d_6$) δ 8.54 (s, 1H), 7.72 (s, 1H), 7.45 (d, 1H), 7.20 (s, 1H), 6.95 (s, 1H), 6.78 (d, 1H), 6.52 (d, 1H), 6.37 (s, 1H), 3.60 (br, 2H), 3.18-3.43 (m, 3H), 2.99 (m, 1H), 2.33-2.45 (m, 3H), 1.77-1.99 (m, 3H), 1.19-1.60 (m, 12H), 1.00-1.06 (m, 4H), 0.63 (m, 1H).

Example 2

MS m/z (ESI): 420.3 [M+1];

Chiral HPLC analysis: retention time 3.725 mins, chiral purity: 99.8% (chromatographic column: Superchiral S-AD (Chiralway), 0.46 cm I.D.*15 cm, 5 m; mobile phase:$CO_2$: methanol:diethanolamine=75:25:0.05 (v/v/v)); and $^1$H NMR (400 MHz, DMSO-$d_6$) δ 8.53 (s, 1H), 7.72 (s, 1H), 7.46 (d, 1H), 7.20 (s, 1H), 6.97 (s, 1H), 6.85 (d, 1H), 6.54 (d, 1H), 6.40 (s, 1H), 3.61 (br, 2H), 3.17-3.25 (m, 3H), 3.00-3.01 (m, 1H), 2.33-2.46 (m, 3H), 1.78-1.97 (m, 3H), 1.24-1.65 (m, 12H), 1.01-1.06 (m, 4H), 0.61 (m, 1H).

Example 3

(1R,2R)-1-((2-((R)-9-(pyridin-2-yl)-6-oxaspiro[4.5]decan-9-yl)ethyl)amino)-2,3-dihydro-1H-inden-2-ol 3

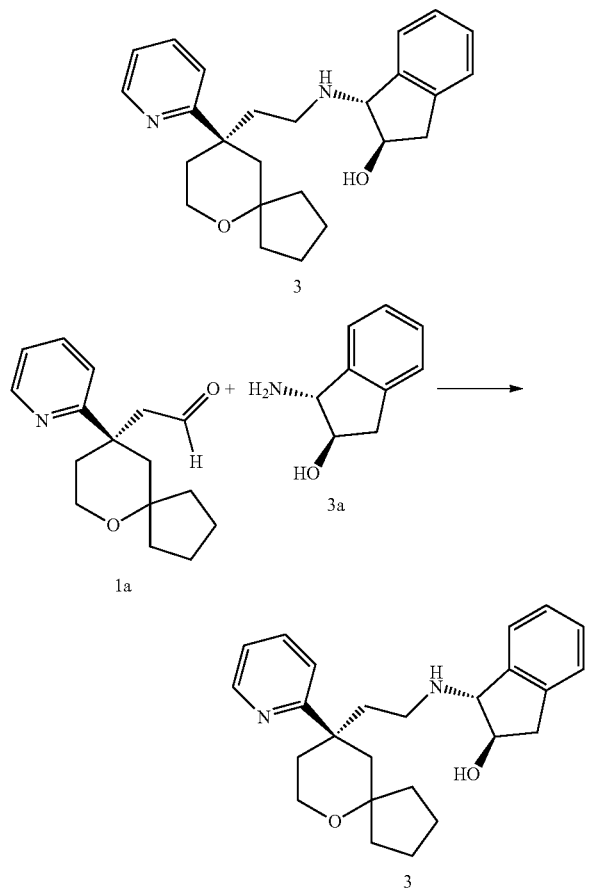

1a (50 mg, 0.193 mmol) and (1R,2R)-1-amino-2,3-dihydro-1H-inden-2-ol 3a (31.6 mg, 0.212 mmol, prepared by a method disclosed in International Patent Application Publication "WO2010148191") were dissolved in 15 mL of dichloromethane, and an appropriate amount of methanol was added to enhance solubility. The resulting mixture was stirred for 1 hour at room temperature, then sodium triacetoxyborohydride (200 mg, 0.965 mmol) was added. After stirring for 16 hours, the reaction solution was concentrated under reduced pressure, and the resulting residue was purified by thin layer chromtography with elution system A to obtain the title compound 3 (50 mg, yield 66%) as a white solid.

MS m/z (ESI): 393.5 [M+1]; and $^1$H NMR (400 MHz, DMSO-$d_6$) δ 8.51 (d, 1H), 7.73-7.66 (m, 1H), 7.37 (d, 1H), 7.28-7.20 (m, 3H), 7.19-7.12 (m, 2H), 4.75 (d, 1H), 4.61 (d, 1H), 3.82-3.71 (m, 4H), 3.41-3.31 (m, 2H), 2.30-2.89 (m, 2H), 2.41-2.25 (m, 2H), 1.96-1.90 (m, 2H), 1.85-1.61 (m, 4H), 1.61-1.25 (m, 6H).

Example 4

(1R,2R)-2-methoxy-N-(2-((R)-9-(pyridin-2-yl)-6-oxaspiro[4.5]decan-9-yl)ethyl)-2,3-dihydro-1H-inden-1-amine 4

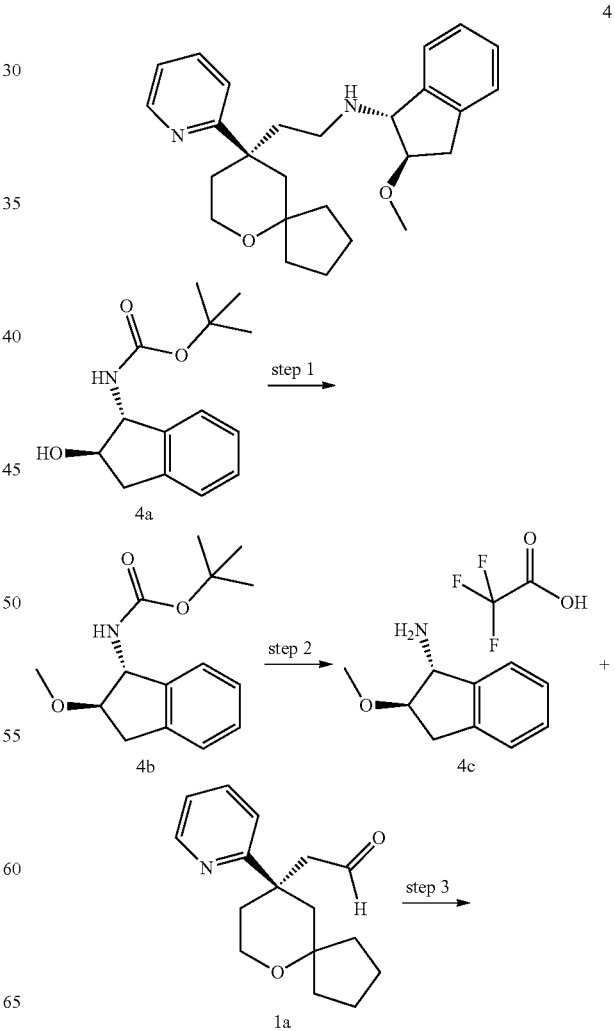

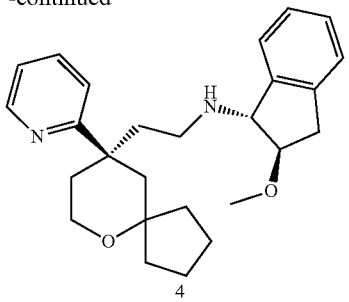

Step 1 tert-butyl ((1R,2R)-2-methoxy-2,3-dihydro-1H-inden-1-yl)carbamate 4b tert-butyl ((1R,2R)-2-hydroxy-2,3-dihydro-1H-inden-1-yl)carbamate 4a (350 mg, 1.34 mmol, prepared by a well known method disclosed in "*Angewandte Chemie-International Edition,* 2012, 51(34), 8495-8499") was dissolved in 15 mL of dichloromethane, then silver oxide (930 mg, 4.02 mmol), iodomethane (0.25 mL, 4.02 mmol) and a small amount of activated 4 Å molecular sieves were added. The resulting mixture was stirred for 16 hours at room temperature, filtered and the filtrate was concentrated under reduced pressure. The resulting residue was purified by thin layer chromtography with elution system B to obtain the title compound 4b (200 mg, yield 57%) as a white solid.

MS m/z (ESI): 208.2 [M−56+1]

Step 2

(1R,2R)-2-methoxy-2,3-dihydro-1H-inden-1-amine 2,2,2-trifluoroacetate 4c 4b (60 mg, 0.228 mmol) was dissolved in 5 mL of dichloromethane, then 0.5 mL of trifluoroacetic acid was added. After stirring for 2 hours, the reaction solution was concentrated under reduced pressure to obtain the crude title compound 4c (66 mg) as a yellow oil, which was used directly in the next step without further purification.

MS m/z (ESI): 164.2 [M+1]

Step 3

(1R,2R)-2-methoxy-N-(2-((R)-9-(pyridin-2-yl)-6-oxaspiro[4.5]decan-9-yl)ethyl)-2,3-dihydro-1H-inden-1-amine 4

1a (50 mg, 0.193 mmol) and the crude 4c (66 mg, 0.228 mmol) were dissolved in 15 mL of dichloromethane. The resulting mixture was stirred for 30 minutes at room temperature, then sodium triacetoxyborohydride (200 mg, 0.965 mmol) was added. After stirring for 16 hours, the reaction mixture was concentrated under reduced pressure, and the resulting residue was purified by thin layer chromtography with elution system A to obtain the title compound 4 (25 mg, yield 32%) as a light yellow oil.

MS m/z (ESI): 407.3 [M+1]; and $^1$H NMR (400 MHz, DMSO-$d_6$) δ 8.55 (d, 1H), 7.71 (d, 1H), 7.58 (d, 1H), 7.40 (d, 1H), 7.28 (d, 1H), 7.25-7.10 (m, 3H), 4.39 (d, 1H), 4.26 (d, 1H), 3.82-3.70 (m, 5H), 3.30 (s, 3H), 2.88-2.30 (m, 2H), 2.40-2.26 (m, 2H), 1.96-1.91 (m, 2H), 1.85-1.62 (m, 4H), 1.61-1.24 (m, 6H).

Example 5

N-(2-((R)-9-(pyridin-2-yl)-6-oxaspiro[4.5]decan-9-yl)ethyl)chroman-4-amine

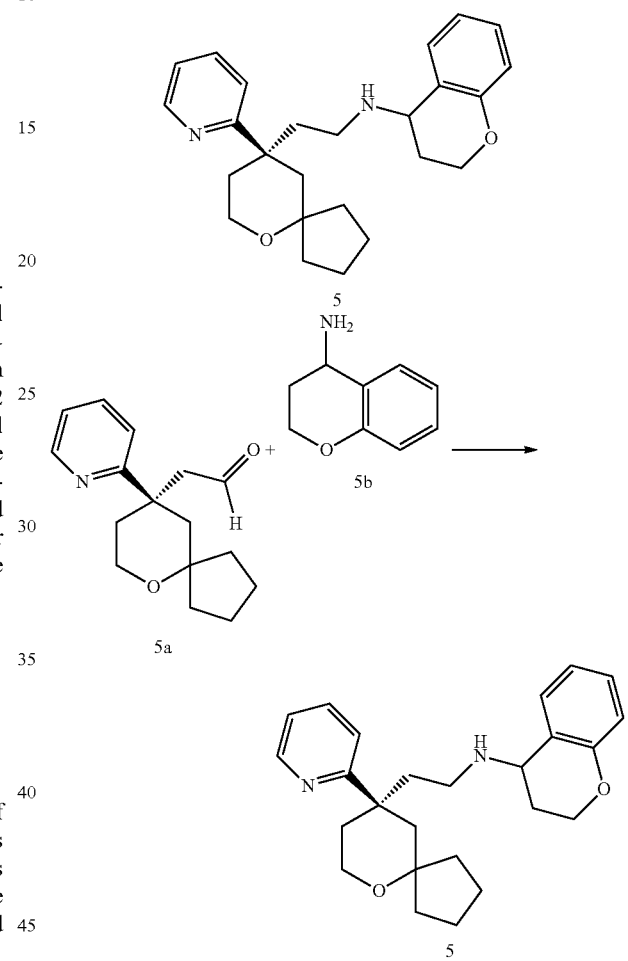

(R)-2-(9-(pyridin-2-yl)-6-oxaspiro[4.5]decan-9-yl)acetaldehyde 5a (20 mg, 0.08 mmol, prepared by a method disclosed in International Patent Application Publication "WO2012129495") and chroman-4-amine 5b (23 mg, 0.15 mmol, prepared by a method disclosed in "*Bioorganic & Medicinal Chemistry Letters,* 2011, 21(5), 1338-1341") were dissolved in 10 mL of dichloromethane, and the mixture was stirred for 2 hours. Then, sodium triacetoxyborohydride (65 mg, 0.31 mmol) was added, and the resulting mixture was stirred for 12 hours. The reaction solution was concentrated under reduced pressure, and the resulting residue was purified by thin layer chromtography with elution system A to obtain the title compound 5 (6 mg, yield 20%) as a yellow oil.

MS m/z (ESI): 393.5 [M+1]; and $^1$H NMR (400 MHz, Methanol-$d_4$) δ 8.55 (s, 1H), 7.78 (t, 1H), 7.52 (d, 1H), 7.27 (d, 1H), 7.01-7.12 (m, 2H), 6.66-6.85 (m, 2H), 4.05-4.23 (m, 2H), 3.71-3.86 (m, 2H), 3.59-3.69 (m, 1H), 2.51-2.65 (m, 2H), 2.37-2.47 (m, 1H), 1.98-2.17

(m, 2H), 1.84-1.96 (m, 2H), 1.37-1.83 (m, 9H), 1.24-1.35 (m, 1H), 1.05-1.17 (m, 1H), 0.65-0.71 (m, 1H).

Example 6

(S)—N-(2-((R)-9-(pyridin-2-yl)-6-oxaspiro[4.5]decan-9-yl)ethyl)chroman-4-amine

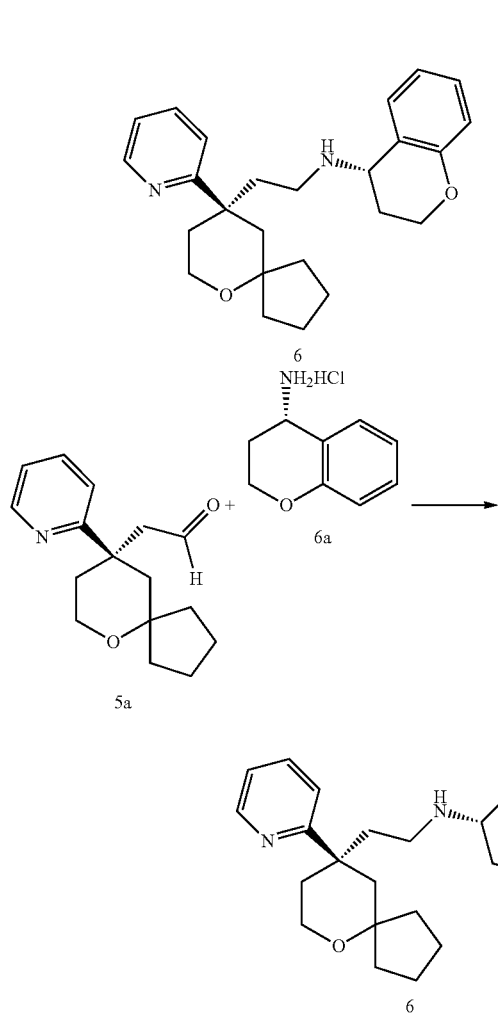

(R)-2-(9-(pyridin-2-yl)-6-oxaspiro[4.5]decan-9-yl)acetaldehyde 5a (80 mg, 0.31 mmol) and (S)-chroman-4-amine hydrochloride 6a (86 mg, 0.46 mmol, prepared by a method disclosed in "*ACS Catalysis,* 3(4), 555-559; 2013") were dissolved in 10 mL of a mixture of dichloromethane and methanol (V:V=5:1), and the mixture was stirred for 1 hour. Then, sodium triacetoxyborohydride (263 mg, 1.24 mmol) was added, and the resulting mixture was stirred for 12 hours. The reaction solution was concentrated under reduced pressure, and the resulting residue was purified by thin layer chromatography with elution system A to obtain the title compound 6 (36 mg, yield 32.1%) as a white viscous solid.

MS m/z (ESI): 393.5 [M+1]; and $^1$H NMR (400 MHz, Methanol-$d_4$) δ 8.55 (d, 1H), 7.80-7.76 (m, 1H), 7.53 (d, 1H), 7.26-7.25 (m, 1H), 7.05-7.01 (m, 2H), 6.78-6.70 (m, 2H), 4.17-4.10 (m, 2H), 3.79-3.63 (m, 3H), 2.56-2.42 (m, 3H), 2.19-2.10 (m, 2H), 1.92-1.82 (m, 2H), 1.80-1.44 (m, 12H).

Example 7

(R)—N-(2-((R)-9-(pyridin-2-yl)-6-oxaspiro[4.5]decan-9-yl)ethyl)chroman-4-amine

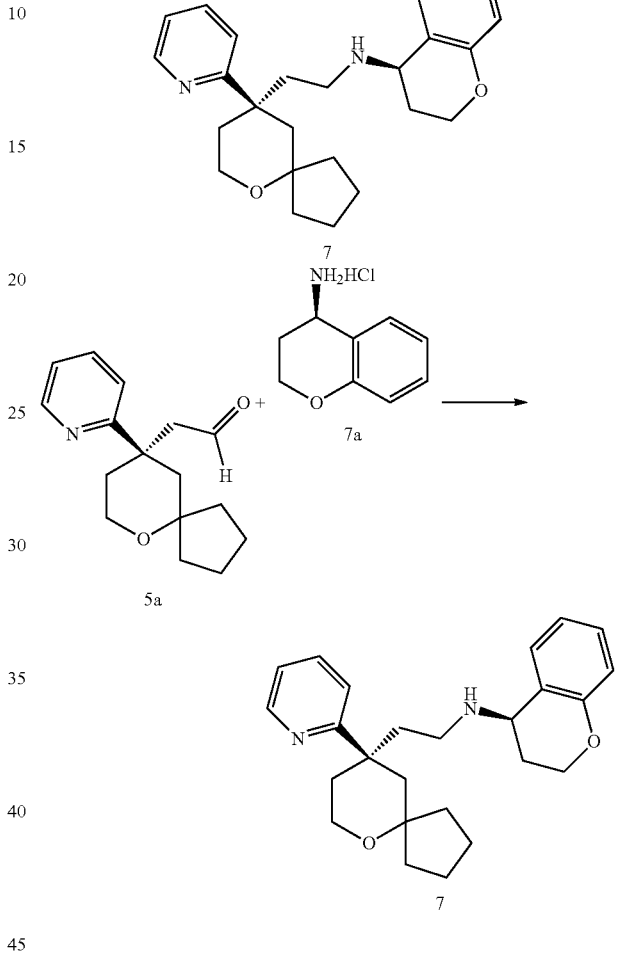

(R)-2-(9-(pyridin-2-yl)-6-oxaspiro[4.5]decan-9-yl)acetaldehyde 5a (80 mg, 0.31 mmol, prepared by a method disclosed in International Patent Application Publication "WO2012129495"), (R)-chroman-4-amine hydrochloride 7a (115 mg, 0.62 mmol, prepared by a method disclosed in "*European Journal of Organic Chemistry,* 2014(31), 7034-7038, 2014") and sodium triacetoxyborohydride (197 mg, 0.93 mmol) were dissolved in 10 mL of a mixture of dichloromethane and methanol (V:V=5:1), and the mixture was stirred for 12 hours. The reaction solution was concentrated under reduced pressure, and the resulting residue was purified by thin layer chromtography with elution system A to obtain the title compound 7 (30 mg, yield 24.8%) as a light yellow oil.

MS m/z (ESI): 393.5 [M+1]; and $^1$H NMR (400 MHz, Methanol-$d_4$) δ 8.63 (d, 1H), 7.93 (t, 1H), 7.64 (d, 1H), 7.39 (t, 1H), 7.29 (t, 1H), 7.19 (d, 1H), 6.81-6.97 (m, 2H), 4.25-4.35 (m, 1H), 4.14-4.24 (m, 1H), 3.79 (d, 2H), 2.47-2.65 (m, 3H), 2.13-2.32 (m, 3H), 1.87-2.03 (m, 2H), 1.72-1.85 (m, 2H), 1.40-1.71 (m, 5H), 1.25-1.35 (m, 2H), 1.06-1.15 (m, 1H), 0.66-0.75 (m, 1H).

Example 8

6-fluoro-N-(2-((R)-9-(pyridin-2-yl)-6-oxaspiro[4.5]decan-9-yl)ethyl)chroman-4-amine

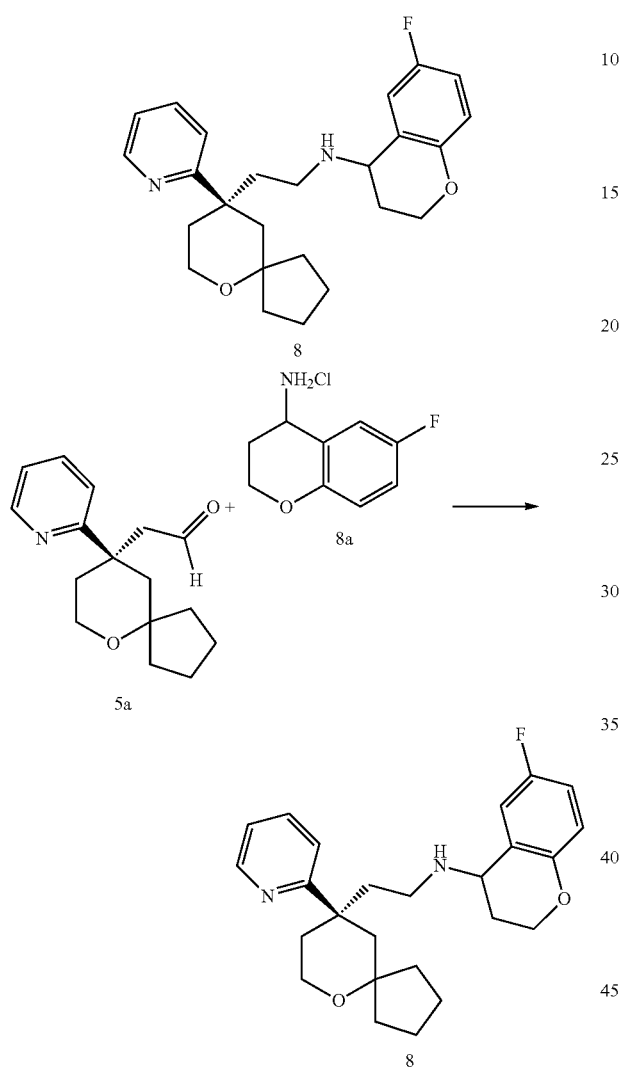

Example 9

(R)—N-(2-((R)-9-(pyridin-2-yl)-6-oxaspiro[4.5]decan-9-yl)ethyl)-1,2,3,4-tetrahydronaphthalen-1-amine (R)-2-(9-(pyridin-2-yl)-6-oxaspiro[4.5]decan-9-yl)acetaldehyde 5a (30 mg, 0.12 mmol, prepared by a method disclosed in International Patent Application Publication "WO2012129495") and 6-fluorochroman-4-amine 8a (39 mg, 0.23 mmol, prepared by a method disclosed in "Bioorganic & Medicinal Chemistry Letters, 2011, 21(5), 1338-1341") were dissolved in 20 mL of dichloromethane, then sodium triacetoxyborohydride (74 mg, 0.35 mmol) was added. After stirring for 12 hours, the reaction solution was concentrated under reduced pressure, and the resulting residue was purified by thin layer chromtography with elution system A to obtain the title compound 8 (10 mg, yield 20.4%) as a light yellow solid.

MS m/z (ESI): 411.2 [M+1]; and $^1$H NMR (400 MHz, CDCl$_3$) δ 8.56 (d, 1H), 7.67-7.64 (m, 1H), 7.34-7.31 (m, 1H), 7.16-7.14 (m, 1H), 6.84-6.74 (m, 2H), 6.73-6.7 (m, 1H), 4.02-4.08 (m, 2H), 3.78-3.75 (m, 3H), 2.66-2.12 (m, 6H), 2.1-1.59 (m, 9H), 1.35-1.18 (m, 4H).

(R)-2-(9-(pyridin-2-yl)-6-oxaspiro[4.5]decan-9-yl)acetaldehyde 5a (35 mg, 0.14 mmol, prepared by a method disclosed in International Patent Application Publication "WO2012129495") and (R)-1,2,3,4-tetrahydronaphthalen-1-amine 9a (40 mg, 0.27 mmol, prepared by a method disclosed in "Angewandte Chemie-International Edition, 45(28), 4641-4644, 2006") were dissolved in 5 mL of dichloromethane. The resulting mixture was stirred for 1 hour, then sodium triacetoxyborohydride (144 mg, 0.68 mmol) was added. After stirring for 1 hour, the reaction solution was concentrated under reduced pressure, and the resulting residue was purified by thin layer chromtography with elution system A to obtain the title compound 9 (15 mg, yield 27.5%) as a yellow solid.

MS m/z (ESI): 391.2 [M+1]; and $^1$H NMR (400 MHz, CDCl$_3$) δ 8.57 (d, 1H), 7.65 (t, 1H), 7.32 (d, 1H), 7.16 (d, 1H), 7.11-7.07 (m, 3H), 7.05 (d, 1H), 3.77 (d, 2H), 3.60-3.57 (br, 1H), 2.73-2.70 (m, 3H), 2.45 (d, 1H), 2.34 (d, 1H), 2.15-2.08 (m, 1H), 2.05-2.02 (m, 1H), 1.91 (d, 1H), 1.75-1.70 (m, 12H), 1.50-1.44 (m, 3H).

Example 10

(S)—N-(2-((R)-9-(pyridin-2-yl)-6-oxaspiro[4.5]decan-9-yl)ethyl)-1,2,3,4-tetrahydronaphthalen-1-amine

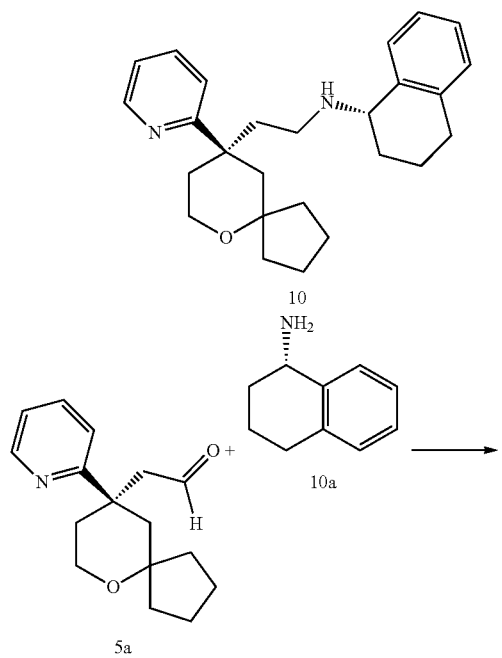

(R)-2-(9-(pyridin-2-yl)-6-oxaspiro[4.5]decan-9-yl)acetaldehyde 5a (20 mg, 0.14 mmol, prepared by a method disclosed in International Patent Application Publication "WO2012129495") and (S)-1,2,3,4-tetrahydronaphthalen-1-amine 10a (50 mg, 0.272 mmol, prepared by a method disclosed in "Angewandte Chemie-International Edition, 45(28), 4641-4644, 2006") were dissolved in 20 mL of dichloromethane. The resulting mixture was stirred for 1 hour, then sodium triacetoxyborohydride (144 mg, 0.68 mmol) was added. After stirring for 1 hour, the reaction solution was concentrated under reduced pressure, and the resulting residue was purified by thin layer chromtography with elution system A to obtain the title compound 10 (15 mg, yield 28.3%) as a yellow solid.

MS m/z (ESI): 391.2 [M+1]; and $^1$H NMR (400 MHz, Methanol-d$_4$) δ 8.77 (d, 1H), 8.28 (t, 1H), 7.92 (d, 1H), 7.71 (t, 1H), 7.33-7.19 (m, 4H), 4.38 (t, 1H), 3.80-3.74 (m, 2H), 3.23-3.11 (m, 1H), 3.08-2.98 (m, 1H), 2.87-2.82 (m, 2H), 2.56-2.48 (m, 3H), 2.26-2.04 (m, 5H), 1.85-1.81 (m, 3H), 1.56-1.32 (m, 5H), 1.34-1.31 (m, 1H), 0.82-0.79 (m, 1H).

Example 11

(S)-4-((2-((R)-9-(pyridin-2-yl)-6-oxaspiro[4.5]decan-9-yl)ethyl)amino)-3,4-dihydronaphthalen-1(2H)-one

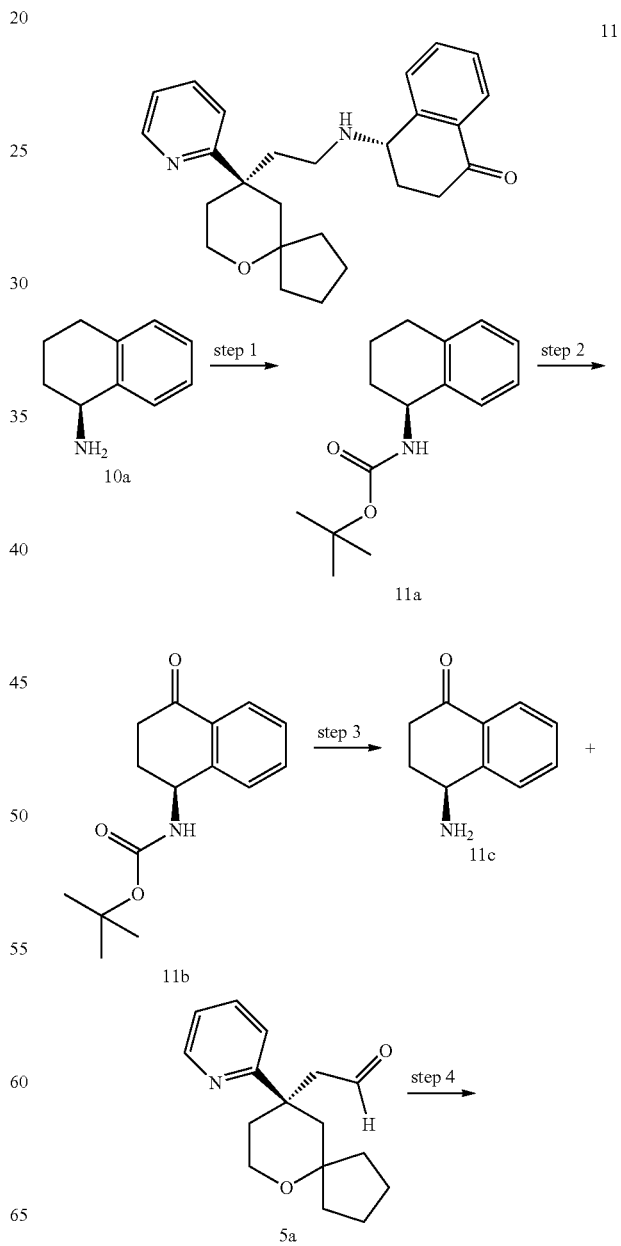

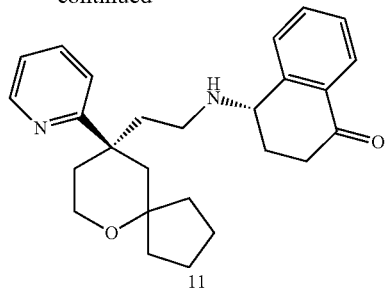

11

Step 1

(S)-tert-butyl (1,2,3,4-tetrahydronaphthalen-1-yl)carbamate 11a (S)-1,2,3,4-tetrahydronaphthalen-1-amine 10a (3 g, 20.41 mmol, prepared by a method disclosed in "*Angewandte Chemie-International Edition*, 45(28), 4641-4644, 2006") was dissolved in 100 mL of dichloromethane, then triethylamine (5.7 mL, 40.82 mmol) and di-tert-butyl dicarbonate (4.9 g, 22. 45 mmol) were added. After stirring for 12 hours, the reaction solution was washed with water (100 mL) and saturated sodium bicarbonate solution (100 mL), successively. The organic phase was dried over anhydrous sodium sulfate, filtered, and the filtrate was concentrated under reduced pressure to obtain the crude compound 11a (5.6 g) as a light yellow oil, which was used directly in the next step without further purification.

MS m/z (ESI): 248.3 [M+1]

Step 2

(S)-tert-butyl (4-oxo-1,2,3,4-tetrahydronaphthalen-1-yl)carbamate 11b

The crude (S)-tert-butyl (1,2,3,4-tetrahydronaphthalen-1-yl)carbamate 11a (5.6 g, 20.41 mmol) was dissolved in 90 mL of a mixture of acetone and water (V/V=2:1), then magnesium sulfate (5.5 g, 45.66 mmol) was added and potassium permanganate (7.22 g, 45.66 mmol) was slowly added with stirring. The reaction system was stirred for 12 hours. Then, the reaction solution was concentrated under reduced pressure, and the resulting residue was purified by silica gel column chromtography with elution system B to obtain the title compound 11b (3.1 g, yield 52%) as an off-white solid.

MS m/z (ESI): 262.3 [M+1]

Step 3

(S)-4-amino-3,4-dihydronaphthalen-1(2H)-one 11c (S)-tert-butyl (4-oxo-1,2,3,4-tetrahydronaphthalen-1-yl)carbamate 11b (1 g, 3.83 mmol) was dissolved in 20 mL of dichloromethane, then 8 mL of 4M hydrogen chloride in 1,4-dioxane solution was added. After stirring for 2 hours, the reaction solution was concentrated under reduced pressure. Then, 10 mL of ethanol were added to the resulting residue, and 30% aqueous ammonia was added dropwise to adjust the pH to 8. The mixture was concentrated under reduced pressure, and the resulting residue was purified by thin layer chromtography with elution system A to obtain the title compound 11c (400 mg, yield 64.8%) as a green viscous material.

MS m/z (ESI): 162.3 [M+1]

Step 4

(S)-4-((2-((R)-9-(pyridin-2-yl)-6-oxaspiro[4.5]decan-9-yl)ethyl)amino)-3,4-dihydronaphthalen-1(2H)-one 11

(S)-4-amino-3,4-dihydronaphthalen-1(2H)-one 11c (200 mg, 1.24 mmol) and (R)-2-(9-(pyridin-2-yl)-6-oxaspiro[4.5]decan-9-yl)acetaldehyde 5a (268 mg, 1.04 mmol, prepared by a method disclosed in International Patent Application Publication "WO2012129495") were dissolved in 20 mL of dichloromethane, and the mixture was stirred for 1 hour, then sodium triacetoxyborohydride (1.1 g, 5.18 mmol) was added. After stirring for 2 hours, the reaction solution was concentrated under reduced pressure, and the resulting residue was purified by thin layer chromtography with elution system A to obtain the title compound 11 (136 mg, yield 32.4%) as a white solid.

MS m/z (ESI): 405.6 [M+1]; and $^1$H NMR (400 MHz, Methanol-$d_4$) δ 8.73 (d, 1H), 8.15-8.09 (m, 2H), 7.83 (d, 1H), 7.81-7.69 (m, 3H), 7.47 (d, 1H), 4.45 (t, 1H), 3.77-3.74 (m, 2H), 3.03-2.98 (m, 1H), 2.75-2.68 (m, 3H), 2.51-2.44 (m, 5H), 2.05-2.01 (m, 2H), 1.57-1.48 (m, 7H), 1.20-1.05 (m, 1H), 0.80-0.77 (m, 1H).

Example 12 and Example 13

(1S,4S)-4-((2-((R)-9-(pyridin-2-yl)-6-oxaspiro[4.5]decan-9-yl)ethyl)amino)-1,2,3,4-tetrahydronaphthalen-1-ol 12

(1R,4S)-4-((2-((R)-9-(pyridin-2-yl)-6-oxaspiro[4.5]decan-9-yl)ethyl)amino)-1,2,3,4-tetrahydronaphthalen-1-ol 13

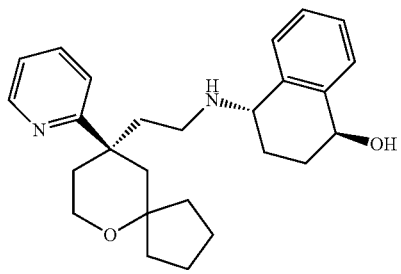

12

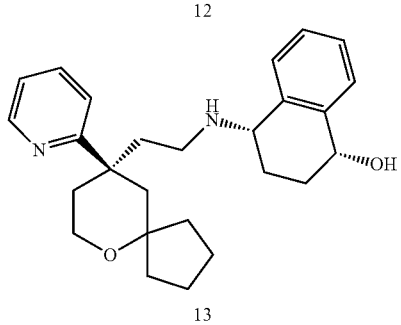

13

-continued

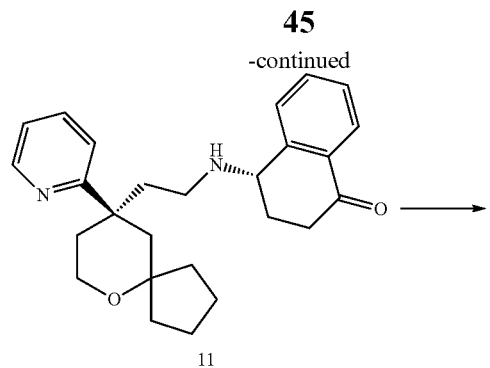
11

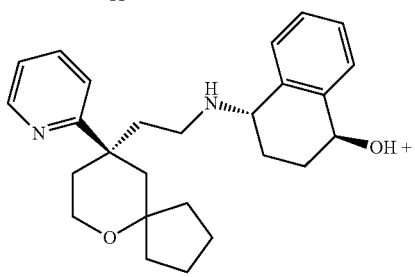
12

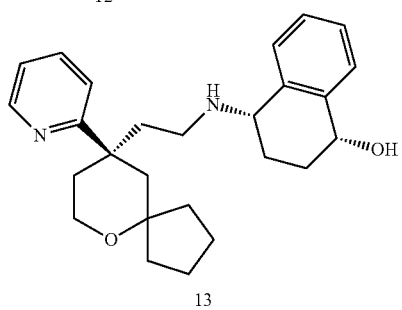
13

(S)-4-((2-((R)-9-(pyridin-2-yl)-6-oxaspiro[4.5]decan-9-yl)ethyl)amino)-3,4-dihydro naphthalen-1(2H)-one 11 (50 mg, 0.12 mmol) was dissolved in 10 mL of dichloromethane, 0.29 mL of 1M diisobutyl aluminium hydroxide solution was added dropwise at −78° C., and the mixture was stirred for 2 hour at −78° C. Then, 5 mL of methanol was added to quench the reaction. The reaction solution was warmed up to room temperature, and concentrated under reduced pressure. The resulting residue was purified by thin layer chromtography with elution system A to obtain the title compounds 12 (18 mg, yield 35.3%) as an off-white viscous solid and 13 (20 mg, yield 39.2%) as an off-white viscous solid.

12: MS m/z (ESI): 407.6 [M+1]; and $^1$H NMR (400 MHz, CDCl$_3$) δ 8.51 (d, 1H), 7.50 (t, 1H), 7.36 (d, 1H), 7.33-7.30 (m, 3H), 7.21-7.18 (m, 2H), 4.83 (t, 1H), 4.25 (t, 1H), 3.81-3.75 (m, 2H), 2.85-2.83 (m, 1H), 2.36-2.30 (m, 5H), 1.98-1.80 (m, 2H), 1.78-1.60 (m, 9H), 1.48-1.25 (m, 5H).

13: MS m/z (ESI): 407.6 [M+1]; and $^1$H NMR (400 MHz, CDCl$_3$) δ 8.51 (d, 1H), 7.50 (t, 1H), 7.36 (d, 1H), 7.33-7.30 (m, 3H), 7.21-7.18 (m, 2H), 4.83 (t, 1H), 4.25 (t, 1H), 3.81-3.75 (m, 2H), 2.85-2.83 (m, 1H), 2.36-2.30 (m, 5H), 1.98-1.80 (m, 2H), 1.78-1.60 (m, 9H), 1.48-1.25 (m, 5H).

Example 14

(1S,4S)-4-methoxy-N-(2-((R)-9-(pyridin-2-yl)-6-oxaspiro[4.5]decan-9-yl)ethyl)-1,2,3,4-tetrahydronaphthalen-1-amine

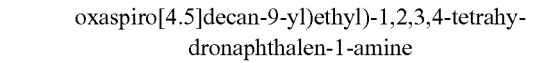

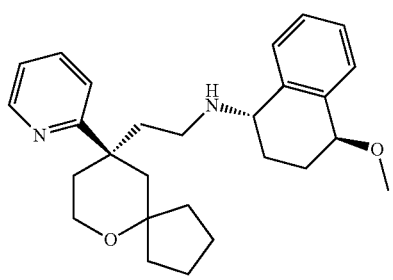
14

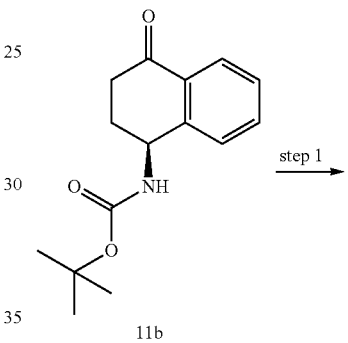
11b

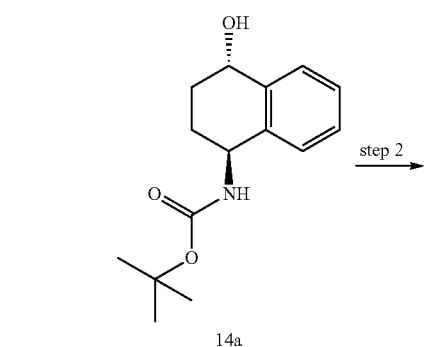
14a

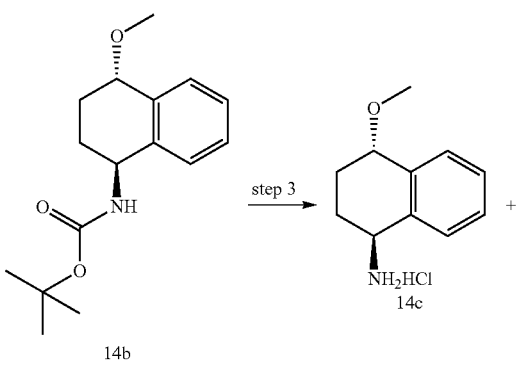
14b, 14c

-continued

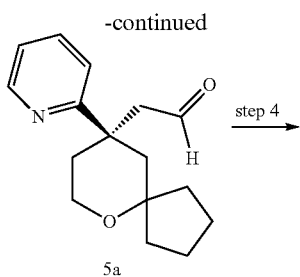

5a

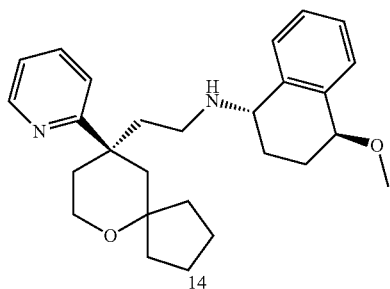

14

Step 1 tert-butyl ((1S,4S)-4-hydroxy-1,2,3,4-tetrahydronaphthalen-1-yl)carbamate 14a (S)-tert-butyl (4-oxo-1,2,3,4-tetrahydronaphthalen-1-yl) carbamate 11b (100 mg, 0.883 mmol) was dissolved in 5 mL of toluene, the reaction was cooled to 0° C., added with (R)-2-methyl-CBS-oxazaborolidine (0.1 ml, 0.076 mmol), and stirred for 5 minutes. Then, borane methylsulfide (0.88 ml, 0.76 mmol) was added, and the reaction was stirred for 2 hours. The reaction was quenched by adding 50 ml of saturated sodium chloride solution, and extracted with ethyl acetate (30 mL×3). The organic phases were combined, washed with saturated sodium chloride solution (30 mL×3), dried over anhydrous sodium sulfate and filtered. The filtrate was concentrated under reduced pressure, and the resulting residue was purified by thin layer chromtography with elution system A to obtain the title compound 14a (60 mg, yield 60%) as a white solid.

MS m/z (ESI): 208.3 [M−55]

Step 2 tert-butyl ((1S,4S)-4-methoxy-1,2,3,4-tetrahydronaphthalen-1-yl)carbamate 14b The crude compound 14a (30 mg, 0.11 mmol) was dissolved in 4 mL of dichloromethane, then silver oxide (76 mg, 0.33 mmol) and methyl iodide (62 mg, 0.44 mmol) were added. After stirring for 48 hours, the reaction solution was filtered. The filtrate was concentrated under reduced pressure to obtain the crude title compound 14b (30 mg) as a yellow oil, which was used directly in the next step without further purification.

MS m/z (ESI): 278.4 [M+1].

Step 3

(1S,4S)-4-methoxy-1,2,3,4-tetrahydronaphthalen-1-amine hydrochloride 14c

The crude compound 14b (30 mg, 0.11 mmol) was dissolved in 0.5 mL of dichloromethane, then 1 mL of a solution of 4M hydrogen chloride in 1,4-dioxane was added. The reaction was stirred for 2.5 hours. The reaction solution was concentrated under reduced pressure to obtain the crude title compound 14c (24 mg) as a white solid, which was used directly in next step without further purification.

MS m/z (ESI): 178.4 [M+1].

Step 4

(1S,4S)-4-methoxy-N-(2-((R)-9-(pyridin-2-yl)-6-oxaspiro[4.5]decan-9-yl)ethyl)-1,2,3,4-tetrahydronaphthalen-1-amine 14

Compound 5a (29 mg, 0.11 mmol), the crude compound 14c (24 mg, 0.11 mmol) and sodium sulfate were dissolved in 4 mL of methanol, and the mixture was stirred for 12 hours. Then, sodium borohydride (8 mg, 0.22 mmol) was added, and the mixture was stirred for 15 minutes. The reaction solution was concentrated under reduced pressure, and the resulting residue was purified by thin layer chromtography with elution system A to obtain the title compound 14 (4 mg, yield 8.7%) as a white solid.

MS m/z (ESI): 407.6 [M+1]; and $^1$H NMR (400 MHz, CDCl$_3$) δ 8.56 (d, 1H), 7.66 (t, 1H), 7.33 (d, 1H), 7.15 (d, 1H), 7.08-7.06 (m, 3H), 7.04 (d, 1H), 3.76 (d, 2H), 3.61-3.58 (br, 1H), 3.41 (s, 3H), 2.74-2.72 (m, 3H), 2.46 (d, 1H), 2.32 (d, 1H), 2.13-2.08 (m, 1H), 2.03-2.00 (m, 1H), 1.90 (d, 1H), 1.75-1.72 (m, 11H), 1.51-1.46 (m, 3H).

Example 15

(R)—N-(2-((R)-9-(pyridin-2-yl)-6-oxaspiro[4.5]decan-9-yl)ethyl)-2,3-dihydro-1H-inden-1-amine

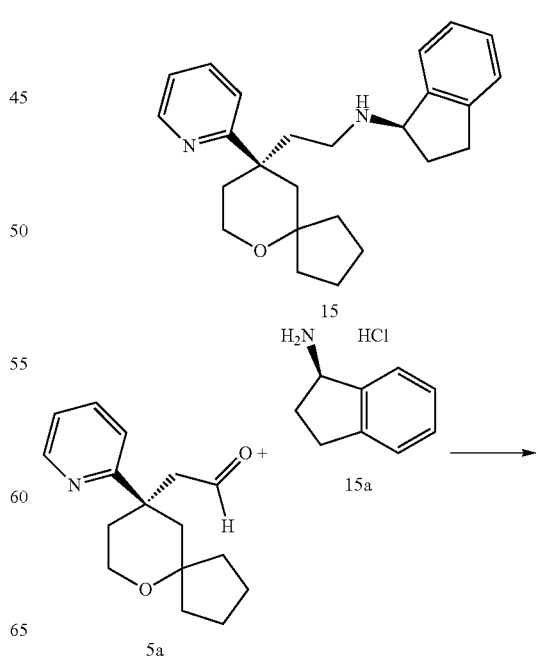

15

5a

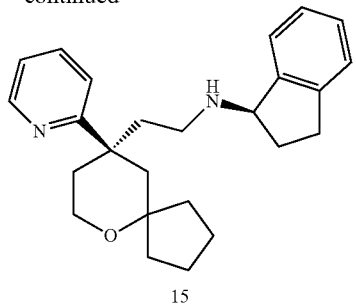

15

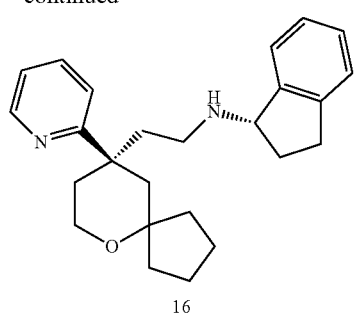

16

(R)-2-(9-(pyridin-2-yl)-6-oxaspiro[4.5]decan-9-yl)acetaldehyde 5a (20 mg, 0.08 mmol) and (R)-2,3-dihydro-1H-inden-1-amine hydrochloride 15a (27 mg, 0.16 mmol, prepared by a method disclosed in "*Synthesis*, (14), 2283-2287, 2008") were dissolved in 10 mL of dichloromethane, and the mixture was stirred for 2 hours, then sodium triacetoxyborohydride (51 mg, 0.24 mmol) was added. After stirring for 12 hours, the reaction solution was concentrated under reduced pressure, and the resulting residue was purified by thin layer chromtography with elution system A to obtain the title compound 15 (5 mg, yield 16.7%) as a yellow oil.

MS m/z (ESI): 377.5 [M+1]; and $^1$H NMR (400 MHz, Methanol-$d_4$) δ 8.62 (d, 1H), 7.91 (t, 1H), 7.60 (d, 1H), 7.37 (s, 4H), 7.35 (d, 1H), 4.64-4.70 (m, 1H), 3.76 (d, 2H), 2.91-3.15 (m, 2H), 2.41-2.60 (m, 4H), 1.85-2.11 (m, 4H), 1.70-1.81 (m, 2H), 1.41-1.69 (m, 5H), 1.31-1.39 (m, 1H), 1.10-1.20 (m, 1H), 0.71-0.80 (m, 1H).

(R)-2-(9-(pyridin-2-yl)-6-oxaspiro[4.5]decan-9-yl)acetaldehyde 5a (20 mg, 0.08 mmol) and (S)-2,3-dihydro-1H-inden-1-amine hydrochloride 16a (26 mg, 0.15 mmol, prepared by a method disclosed in "*Tetrahedron Asymmetry*, 14(22), 3479-3485; 2003") were dissolved in 10 mL of dichloromethane, and the mixture was stirred for 2 hours. Then, sodium triacetoxyborohydride (49 mg, 0.23 mmol) was added. After stirring for 12 hours, the reaction solution was concentrated under reduced pressure, and the resulting residue was purified by thin layer chromtography with elution system A to obtain the title compound 16 (5 mg, yield 17%) as a yellow oil.

MS m/z (ESI): 377.5 [M+1]; and $^1$H NMR (400 MHz, Methanol-$d_4$) δ 8.63 (d, 1H), 7.90 (t, 1H), 7.60 (d, 1H), 7.38 (s, 4H), 7.35 (d, 1H), 4.65-4.70 (m, 1H), 3.76 (d, 2H), 2.90-3.16 (m, 2H), 2.40-2.60 (m, 4H), 1.85-2.10 (m, 4H), 1.70-1.80 (m, 2H), 1.40-1.69 (m, 5H), 1.30-1.39 (m, 1H), 1.10-1.20 (m, 1H), 0.70-0.80 (m, 1H).

Example 16

(S)—N-(2-((R)-9-(pyridin-2-yl)-6-oxaspiro[4.5]decan-9-yl)ethyl)-2,3-dihydro-1H-inden-1-amine Example 17

(1S,2S)-2-methoxy-N-(2-((R)-9-(pyridin-2-yl)-6-oxaspiro[4.5]decan-9-yl)ethyl)-2,3-dihydro-1H-inden-1-amine

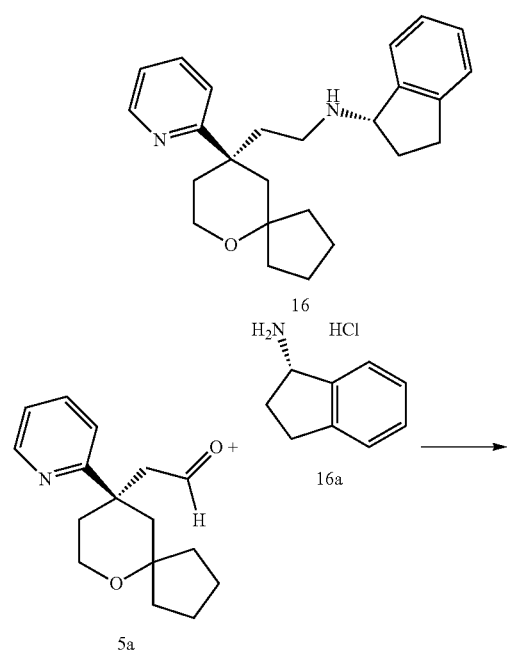

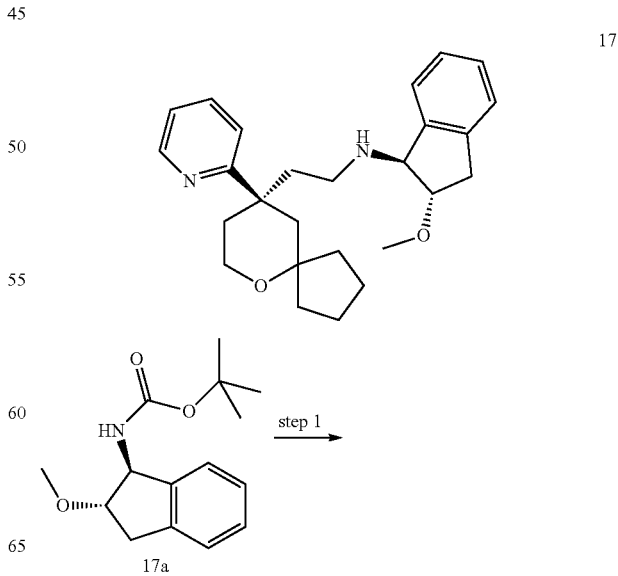

-continued

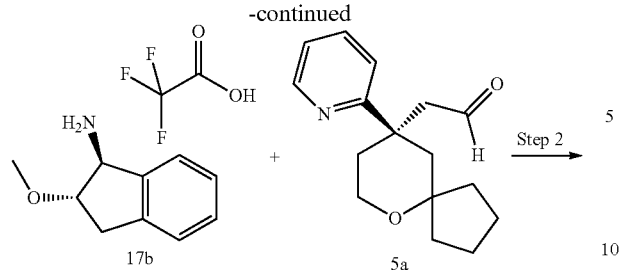

Step 1

(1S,2S)-2-methoxy-2,3-dihydro-1H-inden-1-amine trifluoroacetate 17b tert-butyl ((1S,2S)-2-methoxy-2,3-dihydro-1H-inden-1-yl)carbamate 17a (110 mg, 0.42 mmol, prepared by a method disclosed in International Patent Application Publication "WO2008080015") was dissolved in 5 mL of dichloromethane, then 1 mL of trifluoroacetic acid was added. After stirring for 2 hours, the reaction solution was concentrated under reduced pressure, and the resulting residue was purified by silica gel column chromatography with elution system A to obtain the crude title compound 17b (70 mg, yield 60.3%) as a yellow oil.

MS m/z (ESI): 164.1 [M+1].

Step 2

(1S,2S)-2-methoxy-N-(2-((R)-9-(pyridin-2-yl)-6-oxaspiro[4.5]decan-9-yl)ethyl)-2,3-dihydro-1H-inden-1-amine 17

(R)-2-(9-(pyridin-2-yl)-6-oxaspiro[4.5]decan-9-yl)acetaldehyde 5a (25 mg, 0.96 mmol) and (1S,2S)-2-methoxy-2,3-dihydro-1H-inden-1-amine trifluoroacetate 17b (54 mg, 0.19 mmol) were dissolved in 10 ml of dichloromethane, then sodium triacetoxyborohydribe (61 mg, 0.29 mmol) was added. After stirring for 12 hours, the reaction solution was concentrated under reduced pressure, and the resulting residue was purified by thin layer chromatography with elution system A to obtain the title compound 17 (10 mg, yield 25.5%) as a yellow oil.

MS m/z (ESI): 407.6 [M+1]; and $^1$H NMR (400 MHz, CDCl$_3$) δ 8.58 (d, 1H), 7.71 (t, 1H), 7.57 (d, 1H), 7.40 (d, 1H), 7.29 (d, 1H), 7.16-7.24 (m, 3H), 3.77 (d, 3H), 3.31 (s, 3H), 2.87-3.05 (m, 2H), 2.24-2.50 (m, 4H), 2.14-2.24 (m, 1H), 1.61-1.84 (m, 4H), 1.35-1.51 (m, 5H), 1.24-1.35 (m, 2H), 1.11-1.20 (m, 1H), 0.65-0.75 (m, 1H).

Example 18

(1S,2S)-1-((2-(9-(pyridin-2-yl)-6-oxaspiro[4.5]decan-9-yl)ethyl)amino)-2,3-dihydro-1H-inden-2-ol

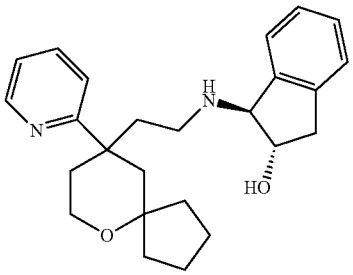

Step 1

2-(9-(pyridin-2-yl)-6-oxaspiro[4.5]decan-9-yl)acetaldehyde 18b 2-(9-(pyridin-2-yl)-6-oxaspiro[4.5]decan-9-yl)acetonitrile 18a (500 mg, 1.95 mmol, prepared by a method disclosed in International Patent Application Publication "WO2012129495") was dissolved in 20 mL of toluene, 4.2 mL of 1 M diisobutylaluminum hydride solution were slowly added dropwise at −78° C., and the reaction was stirred for 1.5 hours. Then, 18 mL of 2 M hydrochloric acid were added, and the mixture was stirred for 30 minutes. Sodium hydroxide solution (5 M) was added dropwise until the pH of the reaction solution was 9 to 10. The mixture was warmed up to room temperature and extracted with ethyl acetate (30 mL×3). The organic phases were combined, washed with saturated sodium chloride solution (30 mL×3), dried over anhydrous sodium sulfate and filtered. The filtrate was concentrated under reduced pressure, and the resulting residue was purified by silica gel column chromatography with elution system A to obtain the title compound 18b (270 mg, yield 53.4%) as a yellow oil.

MS m/z (ESI): 260.5 [M+1].

Step 2

(1S,2S)-1-((2-(9-(pyridin-2-yl)-6-oxaspiro[4.5]decan-9-yl)ethyl)amino)-2,3-dihydro-1H-inden-2-ol 18

Compound 18b (20 mg, 0.08 mmol) and (1S,2S)-1-amino-2,3-dihydro-1H-inden-2-ol 18c (23 mg, 0.15 mmol, prepared by a method disclosed in "*Advanced Synthesis & Catalysis,* 350(14+15), 2250-2260; 2008") were dissolved in 15 mL of a mixture of dichloromethane and methanol (V:V=5:1), the mixture was stirred for 2 hours, then sodium triacetoxyborohydribe (49 mg, 0.23 mmol) was added. After stirring for 12 hours, the reaction solution was concentrated under reduced pressure, and the resulting residue was purified by thin layer chromatography with elution system A to obtain the title compound 18 (10 mg, yield 33%) as a yellow oil.

MS m/z (ESI): 393.5 [M+1]; and $^1$H NMR (400 MHz, CDCl$_3$) δ 8.50 (d, 1H), 7.70 (t, 1H), 7.37 (d, 1H), 7.20-7.26 (m, 3H), 7.11-7.19 (m, 2H), 3.76 (d, 3H), 3.36 (d, 1H), 2.88-3.05 (m, 2H), 2.25-2.50 (m, 4H), 2.15-2.24 (m, 1H), 1.60-1.84 (m, 4H), 1.36-1.51 (m, 5H), 1.25-1.35 (m, 2H), 1.10-1.20 (m, 1H), 0.65-0.75 (m, 1H).

Example 19

(1S,4S)-4-ethoxy-N-(2-((R)-9-(pyridin-2-yl)-6-oxaspiro[4.5]decan-9-yl)ethyl)-1,2,3,4-tetrahydronaphthalen-1-amine

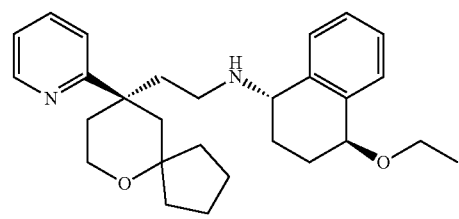

19

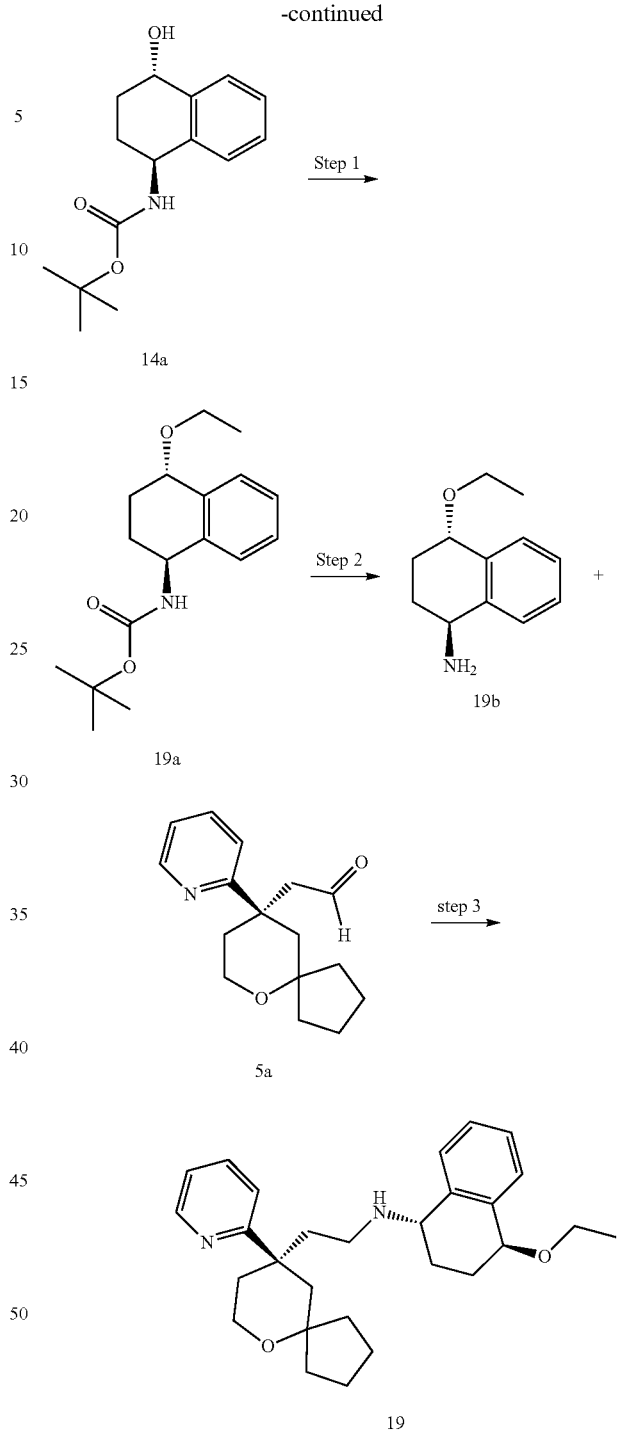

Step 1 tert-butyl ((1S,4S)-4-ethoxy-1,2,3,4-tetrahydronaphthalen-1-yl)carbamate 19a

The crude compound tert-butyl ((1S)-4-hydroxy-1,2,3,4-tetrahydronaphthalen-1-yl) carbamate 14a (850 mg, 3.23 mmol), silver oxide (76 mg, 0.33 mmol) and iodoethane (1.3 mL, 16.15 mmol) were dissolved in 30 mL of dichloromethane, and the mixture was stirred for 48 hours. The reaction solution was filtered, and the filtrate was concentrated under reduced pressure to obtain the crude compound 19a (800 mg) as a yellow oil, which was used directly in the next step without further purification.

MS m/z (ESI): 236.1 [M–55].

Step 2

(1S,4S)-4-ethoxy-1,2,3,4-tetrahydronaphthalen-1-amine 19b

The crude compound 19a (698 mg, 2.4 mmol) was dissolved in 4 mL of dichloromethane, then 8 mL of a solution of 4 M hydrogen chloride in 1,4-dioxane were added. After stirring for 2 hours, the reaction solution was concentrated under reduced pressure, triturated with ethyl acetate (30 mL) and filtered. The filter cake was dissolved in 20 mL of a mixture of dichoromethane and methanol (V:V=5:1). Saturated sodium bicarbonate solution was added to adjust the pH of the reaction solution to 7 to 8. The reaction solution was concentrated under reduced pressure, washed with a mixture of dichloromethane and methanol (V:V=5:1) (30 mL×2) and filtered. The filtrate was concentrated under reduced pressure to obtain the crude title compound 19b (310 mg) as a yellow liquid, which was used directly in next step without further purification.

MS m/z (ESI): 191.1 [M+1].

Step 3

(1S,4S)-4-ethoxy-N-(2-((R)-9-(pyridin-2-yl)-6-oxaspiro[4.5]decan-9-yl)ethyl)-1,2,3,4-tetrahydronaphthalen-1-amine 19

(R)-2-(9-(pyridin-2-yl)-6-oxaspiro[4.5]decan-9-yl)acetaldehyde 5a (500 mg, 1.85 mmol) and the crude compound 19b (310 mg, 1.85 mmol) were dissolved in 30 mL of dichloromethane, and the mixture was stirred for 40 minutes, then sodium triacetoxyborohydribe (980 mg, 4.63 mmol) was added. After stirring for 2 hours, the reaction solution was washed successively with saturated sodium bicarbonate solution (30 mL×3) and saturated sodium chloride solution (30 mL×3). The organic phase was dried over anhydrous sodium sulfate and filtered. The filtrate was concentrated under reduced pressure, and the resulting residue was purified by thin layer chromatography with elution system A to obtain the title compound 19 (280 mg, yield 35%) as a yellow viscous solid.

MS m/z (ESI): 435.3 [M+1]; and

¹H NMR (400 MHz, CDCl₃) δ 9.74 (d, 1H), 9.58 (d, 1H), 8.94 (d, 1H), 8.37 (d, 1H), 7.94 (d, 1H), 7.67 (d, 1H), 7.52 (d, 1H), 7.47 (t, 1H), 4.46-4.49 (m, 1H), 4.30-4.33 (m, 1H), 3.84-3.87 (m, 1H), 3.66-3.70 (m, 2H), 3.53-3.56 (m, 2H), 2.82-2.85 (d, 2H), 2.67 (s, 2H), 2.39-2.41 (m, 4H), 2.30-2.33 (m, 4H), 1.85 (s, 2H), 1.48-1.52 (m, 6H), 1.27 (m, 3H).

Example 20

(1S,4S)-4-(cyclopropylmethoxy)-N-(2-((R)-9-(pyridin-2-yl)-6-oxaspiro[4.5]decan-9-yl)ethyl)-1,2,3,4-tetrahydronaphthalen-1-amine

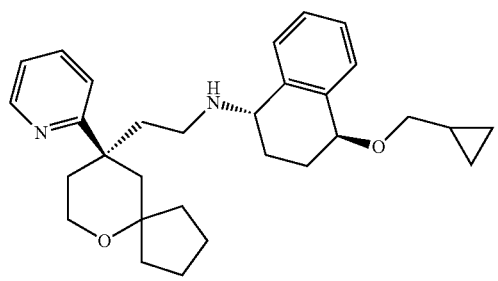

-continued

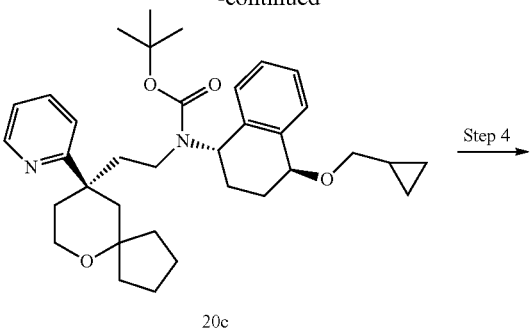

20c

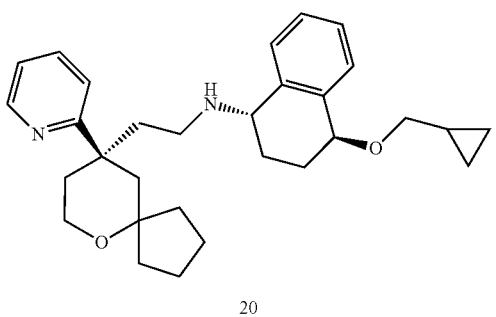

20

Step 1 tert-butyl ((S)-4-oxo-1,2,3,4-tetrahydronaphthalen-1-yl)(2-((R)-9-(pyridin-2-yl)-6-oxaspiro[4.5]decan-9-yl)ethyl)carbamate 20a Compound 11 (220 mg, 0.54 mmol), di-tert-butyl dicarbonate (173 mg, 0.82 mmol) and triethylamine (0.15 mL, 1.08 mmol) were dissolved in 20 mL of dichloromethane. After stirring for 12 hours, the reaction solution was concentrated under reduced pressure, and the resulting residue was purified by thin layer chromatography with elution system A to obtain the title compound 20a (100 mg, yield 37%) as a light yellow viscous solid.

MS m/z (ESI): 505.3 [M+1].

Step 2 tert-butyl ((1S,4S)-4-hydroxy-1,2,3,4-tetrahydronaphthalen-1-yl)(2-((R)-9-(pyridin-2-yl)-6-oxaspiro[4.5]decan-9-yl)ethyl)carbamate 20b Compound 20a (100 mg, 0.2 mmol) and 1M (R)-2-methyl-CBS-oxazaborolidine (0.04 mL, 0.4 mmol) were dissolved in 10 mL of toluene, the reaction was cooled to 0° C., then 2 M borane methylsulfide (0.02 mL, 0.4 mmol) was added. The reaction was warmed up to room temperature and stirred for 3 hours. The reaction was quenched by adding 10 mL of saturated sodium chloride solution and extracted with ethyl acetate (10 mL×3). The organic phases were combined, washed with saturated sodium chloride solution (10 mL×3), dried over anhydrous sodium sulfate and filtered. The filtrate was concentrated under reduced pressure, and the resulting residue was purified by thin layer chromatography with elution system A to obtain the title compound 20b (10 mg, yield 10%) as a white solid.

MS m/z (ESI): 507.3 [M+1].

Step 3 tert-butyl ((1S,4S)-4-(cyclopropylmethoxy)-1,2,3,4-tetrahydronaphthalen-1-yl)(2-((R)-9-(pyridin-2-yl)-6-oxaspiro[4.5]decan-9-yl)ethyl)carbamate 20c Compound 20b (10 mg, 0.02 mmol) was dissolved in 5 mL of N,N-dimethylformamide, then sodium hydride (2.2 mg, 0.06 mmol) was added. The mixture was stirred for 30 minutes, then cyclopropylmethyl bromide (6.7 mg, 0.05 mmol) was added. After stirring for 3 hours, the reaction was quenched by adding 20 mL of water and extracted with ethyl acetate (10 mL×3). The organic phases were combined, washed with saturated sodium chloride solution (10 mL×3), dried over anhydrous sodium sulfate and filtered. The filtrate was concentrated under reduced pressure to obtain the crude title compound 20c (5 mg) as a white solid, which was used directly in next step without further purification.

MS m/z (ESI): 561.0 [M+1].

Step 4

(1S,4S)-4-(cyclopropylmethoxy)-N-(2-((R)-9-(pyridin-2-yl)-6-oxaspiro[4.5]decan-9-yl)ethyl)-1,2,3,4-tetrahydronaphthalen-1-amine 20d The crude compound 20c (5 mg, 0.0089 mmol) was dissolved in 5 mL of dichloromethane, then 0.1 mL of a solution of 4 M hydrochloric acid in 1,4-dioxane was added. After stirring for 2 hours, the reaction solution was concentrated under reduced pressure, and the resulting residue was purified by thin layer chromatography with elution system A to obtain the title compound 20d (3 mg, yield 73.2%) as a white solid.

MS m/z (ESI): 461.3 [M+1]; and
$^1$H NMR (400 MHz, CD$_3$OD) δ 8.59 (d, 1H), 7.84-7.81 (m, 1H), 7.55 (d, 1H), 7.53 (d, 1H), 7.47-7.40 (m, 1H), 7.39-7.29 (m, 2H), 7.25 (d, 1H), 4.48-4.46 (m, 1H), 4.28-4.25 (m, 1H), 3.77-3.75 (m, 2H), 3.45-3.43 (m, 2H), 3.35-3.30 (m, 2H), 2.93-2.92 (m, 1H), 2.53-2.50 (m, 2H), 2.49-2.48 (m, 1H), 2.25-2.13 (m, 2H), 1.95-1.31 (m, 11H), 1.10-1.08 (m, 2H), 0.76-0.73 (m, 1H), 0.55-0.53 (m, 2H), 0.25-0.23 (m, 2H).

Example 21

(1S,4S)-4-(2-fluoroethoxy)-N-(2-((R)-9-(pyridin-2-yl)-6-oxaspiro[4.5]decan-9-yl)ethyl)-1,2,3,4-tetrahydronaphthalen-1-amine

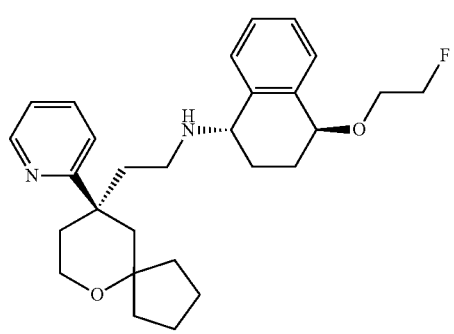

21

-continued

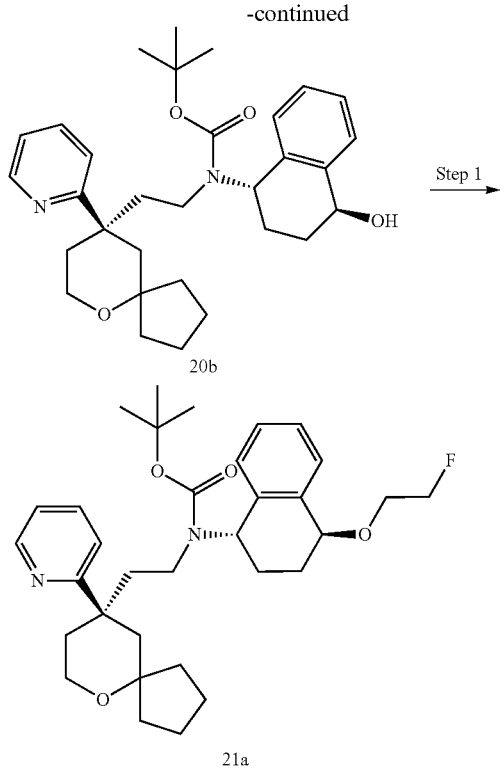

Step 1 tert-butyl ((1S,4S)-4-(2-fluoroethoxy)-1,2,3,4-tetra-hydronaphthalen-1-yl)(2-((R)-9-(pyridin-2-yl)-6-oxaspiro[4.5]decan-9-yl)ethyl)carbamate 21a Compound 20b (45 mg, 0.088 mmol) was dissolved in 5 mL of N,N-dimethylformamide, then sodium hydride (20 mg, 0.44 mmol) was added. The mixture was stirred for 20 minutes, then 1-bromo-2-fluoroethane (23 mg, 0.176 mmol) was added. After stirring for 16 hours, the reaction was quenched by adding 5 mL of water and extracted with ethyl acetate (10 mL×3). The organic phases were combined, washed with saturated sodium chloride solution (30 mL×3), dried over anhydrous sodium sulfate and filtered. The filtrate was concentrated under reduced pressure, and the resulting residue was purified by thin layer chromatography with elution system A to obtain the title compound 21a (30 mg, yield 61.1%) as a yellow oil.

MS m/z (ESI): 553.4 [M+1].

Step 2

(1S,4S)-4-(2-fluoroethoxy)-N-(2-((R)-9-(pyridin-2-yl)-6-oxaspiro[4.5]decan-9-yl)ethyl)-1,2,3,4-tetrahydronaphthalen-1-amine 21

Compound 21a (30 mg, 0.543 mmol) was dissolved in 10 mL of dichloromethane, then 0.3 mL of a solution of 4M hydrochloric acid in 1,4-dioxane was added. The mixture was stirred for 1 hour, then 10 mg of sodium carbonate was added. The reaction solution was concentrated under reduced pressure, and the resulting residue was purified by thin layer chromatography with elution system A to obtain the title compound 21 (10 mg, yield 40.7%) as a white viscous material.

MS m/z (ESI): 453.4 [M+1]; and $^1$H NMR (400 MHz, CDCl$_3$) δ 9.76 (d, 1H), 9.61 (d, 1H), 8.89 (d, 1H), 8.34 (d, 1H), 7.94 (d, 1H), 7.69 (d, 1H), 7.58 (d, 1H), 7.44 (t, 1H), 4.43-4.49 (m, 2H), 4.28-4.33 (m, 2H), 3.81-3.87 (m, 1H), 3.61-3.71 (m, 2H), 3.51-3.56 (m, 2H), 2.81-2.89 (d, 2H), 2.67 (s, 2H), 2.39-2.43 (m, 4H), 2.30-2.36 (m, 4H), 1.85 (s, 2H), 1.48-1.61 (m, 6H).

Examples 22, 23

(1S,4S)-4-(methoxymethyl)-N-(2-((R)-9-(pyridin-2-yl)-6-oxaspiro[4.5]decan-9-yl)ethyl)-1,2,3,4-tetrahydronaphthalen-1-amine 22

(1S,4R)-4-(methoxymethyl)-N-(2-((R)-9-(pyridin-2-yl)-6-oxaspiro[4.5]decan-9-yl)ethyl)-1,2,3,4-tetrahydronaphthalen-1-amine 23

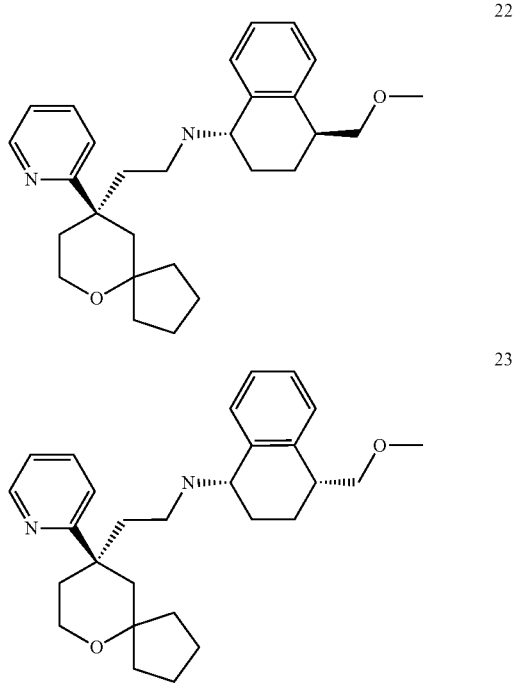

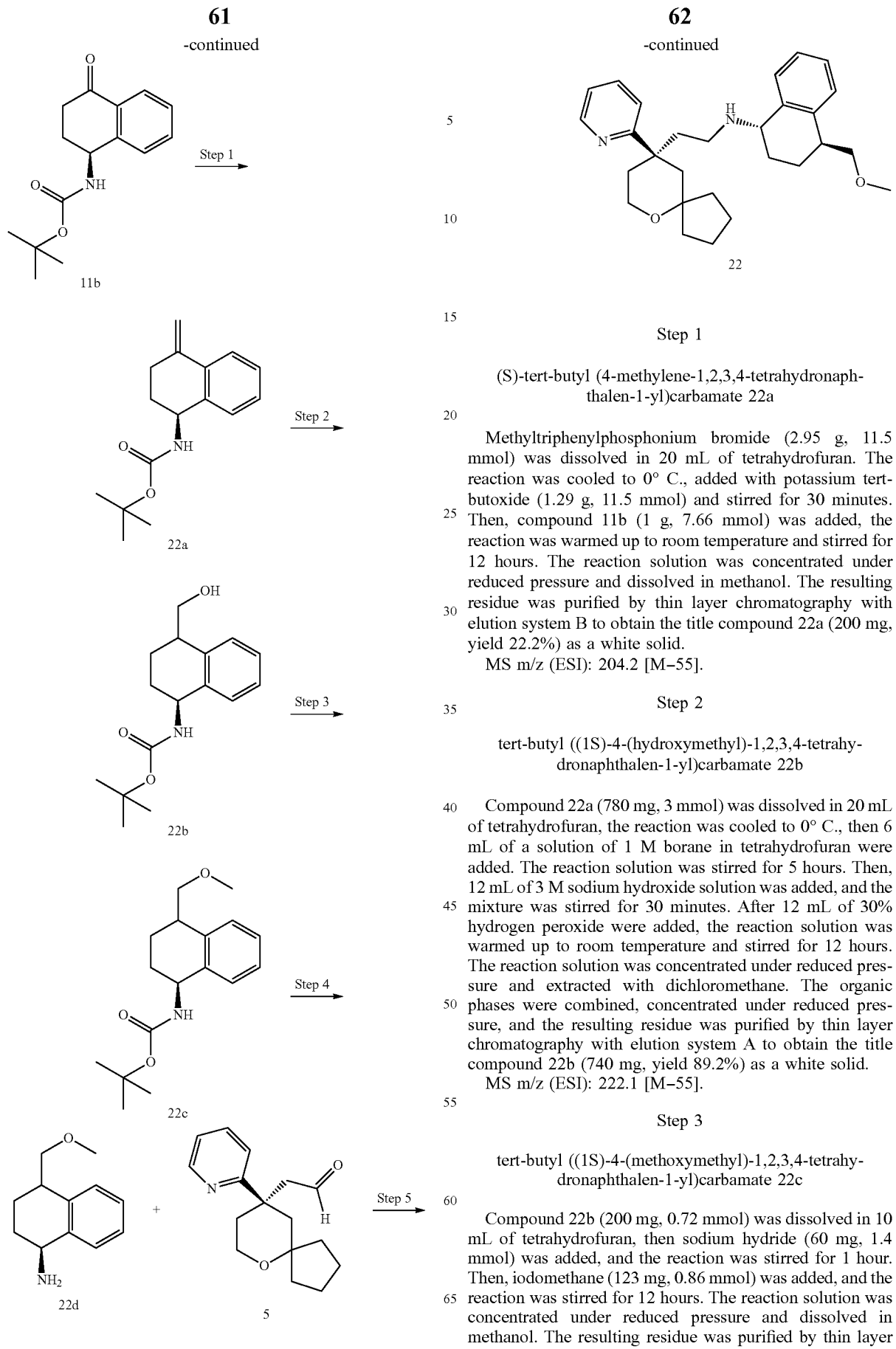

Step 1

(S)-tert-butyl (4-methylene-1,2,3,4-tetrahydronaphthalen-1-yl)carbamate 22a

Methyltriphenylphosphonium bromide (2.95 g, 11.5 mmol) was dissolved in 20 mL of tetrahydrofuran. The reaction was cooled to 0° C., added with potassium tert-butoxide (1.29 g, 11.5 mmol) and stirred for 30 minutes. Then, compound 11b (1 g, 7.66 mmol) was added, the reaction was warmed up to room temperature and stirred for 12 hours. The reaction solution was concentrated under reduced pressure and dissolved in methanol. The resulting residue was purified by thin layer chromatography with elution system B to obtain the title compound 22a (200 mg, yield 22.2%) as a white solid.

MS m/z (ESI): 204.2 [M−55].

Step 2 tert-butyl ((1S)-4-(hydroxymethyl)-1,2,3,4-tetrahydronaphthalen-1-yl)carbamate 22b Compound 22a (780 mg, 3 mmol) was dissolved in 20 mL of tetrahydrofuran, the reaction was cooled to 0° C., then 6 mL of a solution of 1 M borane in tetrahydrofuran were added. The reaction solution was stirred for 5 hours. Then, 12 mL of 3 M sodium hydroxide solution was added, and the mixture was stirred for 30 minutes. After 12 mL of 30% hydrogen peroxide were added, the reaction solution was warmed up to room temperature and stirred for 12 hours. The reaction solution was concentrated under reduced pressure and extracted with dichloromethane. The organic phases were combined, concentrated under reduced pressure, and the resulting residue was purified by thin layer chromatography with elution system A to obtain the title compound 22b (740 mg, yield 89.2%) as a white solid.

MS m/z (ESI): 222.1 [M−55].

Step 3 tert-butyl ((1S)-4-(methoxymethyl)-1,2,3,4-tetrahydronaphthalen-1-yl)carbamate 22c Compound 22b (200 mg, 0.72 mmol) was dissolved in 10 mL of tetrahydrofuran, then sodium hydride (60 mg, 1.4 mmol) was added, and the reaction was stirred for 1 hour. Then, iodomethane (123 mg, 0.86 mmol) was added, and the reaction was stirred for 12 hours. The reaction solution was concentrated under reduced pressure and dissolved in methanol. The resulting residue was purified by thin layer chromatography with elution system B to obtain the title compound 22c (20 mg, yield 9.5%) as a white solid.

MS m/z (ESI): 236.2 [M−55].

Step 4

(1S)-4-(methoxymethyl)-1,2,3,4-tetrahydronaphthalen-1-amine 22d

The crude compound 22c (20 mg, 0.07 mmol) was dissolved in 10 mL of dichloromethane, then 10 mL of a solution of 4M hydrochloric acid in 1,4-dioxane were added. After stirring for 2 hours, the reaction solution was concentrated under reduced pressure to obtain the crude title compound 22d (13 mg) as a yellow oil, which was directly used in next step without further purification.

MS m/z (ESI): 192.2 [M−55].

Step 5

(1S,4S)-4-(methoxymethyl)-N-(2-((R)-9-(pyridin-2-yl)-6-oxaspiro[4.5]decan-9-yl)ethyl)-1,2,3,4-tetrahydronaphthalen-1-amine 22

Compound 5a (30 mg, 0.116 mmol) and the crude compound 22d (22 mg, 0.116 mmol) were dissolved in 20 mL of a mixture of dichloromethane and methanol (V:V=1:1), then sodium cyanoborohydride (15 mg, 0.23 mmol) was added. After stirring for 12 hours, the reaction solution was concentrated under reduced pressure, and the resulting residue was purified by thin layer chromatography with elution system A to obtain the title compound 22 (10 mg, yield 20%) as a white solid and the title compound 23 (8 mg, yield 16%) as a white solid.

MS m/z (ESI): 435.3 [M+1]

Example 22

¹H NMR (400 MHz, CDCl₃) δ 8.26-8.25 (d, 1H), 7.76-7.72 (t, 1H), 7.42-7.40 (d, 1H), 7.34-7.29 (m, 3H), 7.29-7.27 (m, 1H), 7.18-7.16 (m, 1H), 4.16 (s, 1H), 3.75-3.70 (m, 2H), 3.47-3.45 (m, 2H), 3.41 (s, 3H), 3.35-3.33 (m, 1H), 3.18-3.17 (m, 1H), 2.80-2.70 (m, 1H), 2.4-2.33 (m, 1H), 2.28-1.95 (m, 7H), 1.81-1.62 (m, 5H), 1.59-1.51 (m, 1H), 1.46-1.20 (m, 4H), 1.22-1.1 (m, 1H).

Example 23

¹H NMR (400 MHz, CDCl₃) δ 8.47-8.46 (d, 1H), 7.72-7.68 (t, 1H), 7.39-7.37 (d, 1H), 7.37-7.33 (m, 1H), 7.24-7.21 (m, 1H), 7.15-7.05 (m, 2H), 6.93-6.91 (d, 1H), 3.94 (s, 1H), 3.68-3.60 (m, 2H), 3.59-3.57 (m, 2H), 3.22 (s, 3H), 3.22-3.19 (m, 1H), 2.71-2.70 (m, 1H), 2.34-2.30 (m, 5H), 2.28-2.25 (m, 1H), 1.84-1.81 (m, 1H), 1.81-1.71 (m, 5H), 1.69-1.51 (m, 2H), 1.45-1.4 (m, 2H), 1.32-1.26 (m, 2H), 1.23-1.15 (m, 1H), 1.1-0.95 (m, 1H).

Example 24

(S)—N-(2-((R)-9-(pyridin-2-yl)-6-oxaspiro[4.5]decan-9-yl)ethyl)-3',4'-dihydro-2'H-spiro[[1,3]dithiolane-2,1'-naphthalen]-4'-amine 24

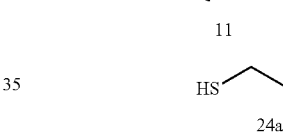

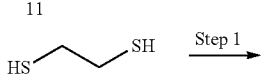

Compound 11 (35 mg, 0.0865 mmol), ethane-1,2-dithiol 24a (82 mg, 0.865 mmol) and pyridinium p-toluenesulfonate (240 mg, 0.952 mmol) were dissolved in 15 mL of toluene, and the reaction was warmed up to 110° C. and stirred for 12 hours. The reaction solution was concentrated under reduced pressure, and the resulting residue was purified by thin layer chromatography with elution system A to obtain the title compound 24 (40 mg, yield 96%) as a light yellow solid.

MS m/z (ESI): 481.2 [M+1]; and

¹H NMR (400 MHz, CD₃OD): δ 8.60 (d, 1H), 7.60 (t, 1H), 7.25-7.31 (m, 2H), 7.15-7.20 (m, 4H), 4.26-4.30 (m, 1H), 3.76 (d, 1H), 2.81-3.01 (m, 4H), 2.41-2.60 (m, 2H), 2.21-2.30 (m, 2H), 1.86-2.13 (m, 4H), 1.70-1.81 (m, 2H), 1.41-1.69 (m, 5H), 1.31-1.39 (m, 2H), 1.10-1.20 (m, 2H), 0.71-0.80 (m, 2H).

Example 25

(1S,4R)-4-ethoxy-N-(2-((R)-9-(pyridin-2-yl)-6-oxas-piro[4.5]decan-9-yl)ethyl)-1,2,3,4-tetrahydronaph-thalen-1-amine 25

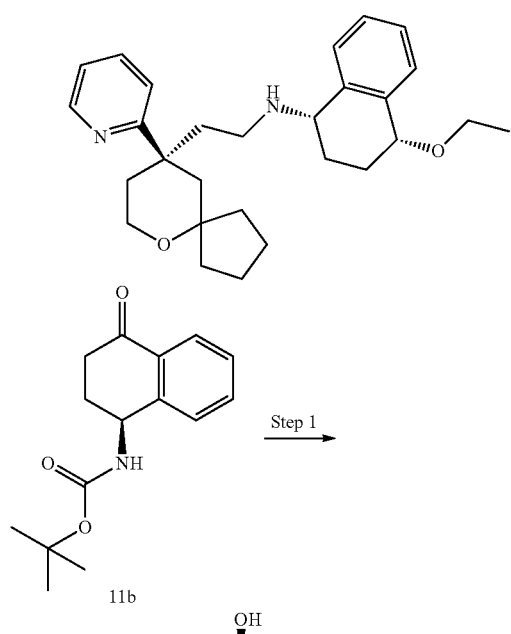

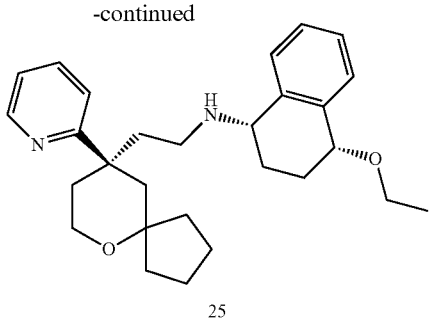

Step 1 tert-butyl ((1S,4R)-4-hydroxy-1,2,3,4-tetrahy-dronaphthalen-1-yl)carbamate 25a (S)-2-methyl-CBS-oxazaborolidine (221.8 mg, 0.8 mmol) was dissolved in 140 mL of tetrahydrofuran, then borane methylsulfide (2.4 ml, 48 mmol) was added under an argon atmosphere. The reaction was warmed up to 30° C., then 80 mL of a pre-prepared solution of 11b (10.5 g, 40 mmol) in tetrahydrofuran were added dropwise over 30 minutes. The reaction mixture was stirred for 1 hour at 30° C. Then, 100 mL of methanol was added at 15° C. and stirred for 1 hour to quench the reaction. The reaction solution was concentrated under reduced pressure. Then, 200 mL of ethyl acetate and 5 g of activated carbon were added. The mixture was stirred for 30 minutes under micro-boiling, and filtered. The filter cake was washed with ethyl acetate (100 mL×3). The filtrate was concentrated under reduced pressure to obtain the crude title compound 25a (10.5 g) as a colorless oil.

MS m/z (ESI): 264.4 [M+1].

Steps 2 to 4

(1S,4R)-4-ethoxy-N-(2-((R)-9-(pyridin-2-yl)-6-oxas-piro[4.5]decan-9-yl)ethyl)-1,2,3,4-tetrahydronaph-thalen-1-amine 25

In accordance with the synthetic route of Example 19, the starting material 14a was replaced with 25a. Accordingly, the title compound 25 (7 g) was prepared as a light red oil.

MS m/z (ESI): 435.5 [M+1]; and $^1$H NMR (400 MHz, DMSO-d6) δ 0.62 (dt, 1H), 0.92-1.03 (m, 1H), 1.12 (t, 3H), 1.34 (td, 2H), 1.41-1.69 (m, 9H), 1.79 (d, 1H), 1.82-1.92 (m, 2H), 2.02 (td, 1H), 2.26-2.38 (m, 2H), 2.43 (d, 1H), 3.37-3.48 (m, 2H), 3.52-3.66 (m, 3H), 4.25 (t, 1H), 7.11-7.16 (m, 2H), 7.16-7.20 (m, 1H), 7.21-7.28 (m, 2H), 7.45 (d, 1H), 7.71 (td, 1H), 8.52 (dd, 1H).

Example 26

(1S,4S)-4-(ethoxy-d$_5$)-N-(2-((R)-9-(pyridine-2-yl)-6-oxaspiro[4.5]dec-9-yl)ethyl)-1,2,3,4-tetrahydronaph-thalen-1-amine 26

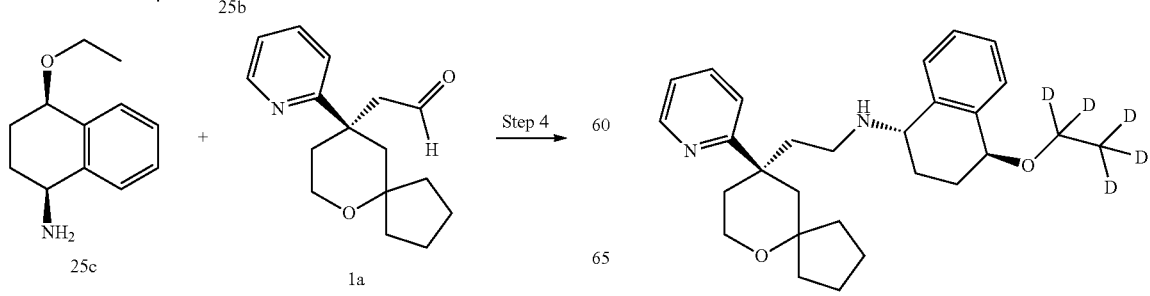

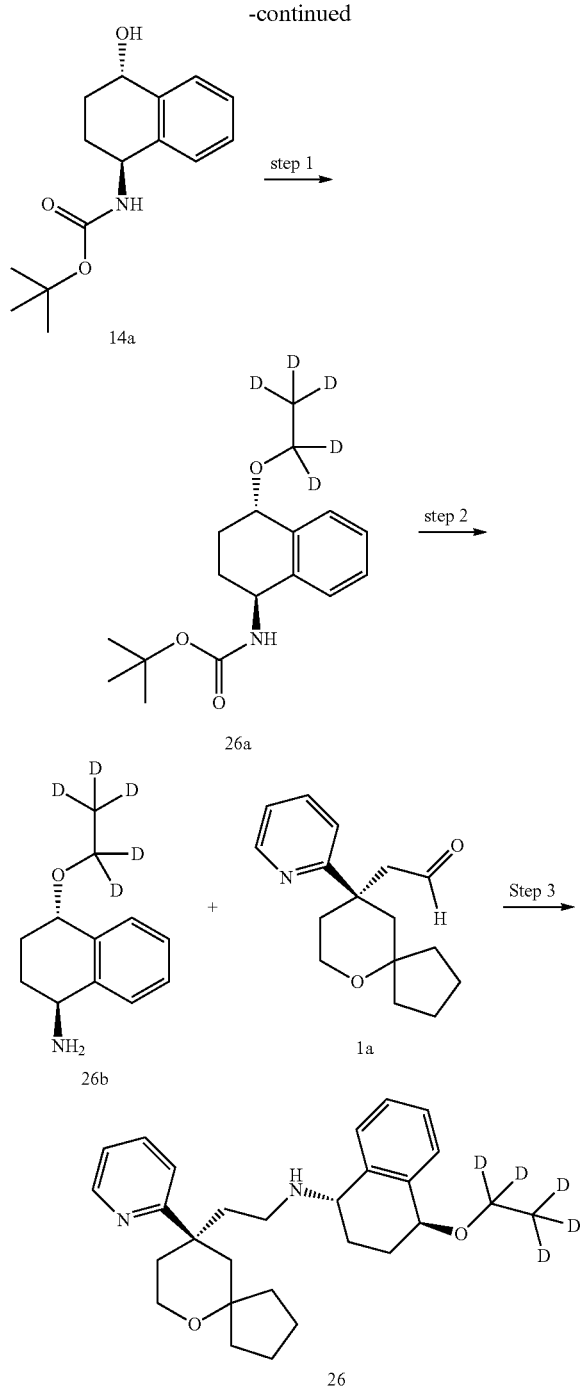

Step 1 tert-butyl ((1S,4S)-4-(ethoxy-d$_5$)-1,2,3,4-tetrahydronaphthalen-1-yl)carbamate 26a Compound 14a (3.3 g, 12.5 mmol) was dissolved in 50 mL of N,N-dimethylformamide, then activated molecular sieves were added. After the reaction solution was cooled to 0° C., sodium hydroxide (0.75 g, 18.75 mmol) was added under an argon atmosphere. The reaction was stirred for 0.5 hours at 0° C. Then, deuterated iodoethane-d$_5$ (0.8 mL, 10 mmol) was added, and the reaction was sealed for 16 hours at 0° C. After the reaction was completed, the reaction solution was poured into a mixture of 50 mL of water, 50 mL of n-hexane and 5 mL of ethyl acetate, stirred for 10 minutes and filtered. Insolubles were removed. The filtrate was separated into two phases, and the aqueous phase was extracted with a mixture of n-hexane and ethyl acetate (V:V=10:1) (33 mL×2). The organic phases were combined, washed with saturated sodium chloride solution (30 mL×2), dried over anhydrous sodium sulfate and filtrated. The filtrate was concentrated under reduced pressure, and the resulting residue was purified by a CombiFlash flash preparation instrument with elution system B to obtain the title compound 26a (1.89 g, yield 64%) as a white solid.

MS m/z (ESI): 241.4 [M–56+1].

Step 2

(1S,4S)-4-(ethoxy-d$_5$)-1,2,3,4-tetrahydronaphthalen-1-amine 26b

A solution of 4M hydrogen chloride in 1,4-dioxane (8 mL) was added to compound 26a (1.89 g, 6.38 mmol). The reaction solution was stirred for 1 hour and concentrated under reduced pressure. Then, 30 mL of ethyl acetate were added, and the mixture was concentrated under reduced pressure. Saturated sodium carbonate solution (1 mL) was added to the resulting residue, and the mixture was stirred for 5 minutes. Then, 30 mL of ethyl acetate, 2 g of sodium carbonate solid and 10 g of sodium sulfate were added, and the reaction solution was stirred for 30 minutes until the solution was no longer turbid. The mixture was filtered, and the filtrate was concentrated under reduced pressure to obtain the crude title compound 26b (1.21 g, a light brown liquid), which was used directly in the next step without further purification.

MS m/z (ESI): 197.4 [M+1].

Step 3

(1S,4S)-4-(ethoxy-d$_5$)-N-(2-((R)-9-(pyridine-2-yl)-6-oxaspiro[4.5]dec-9-yl)ethyl)-1,2,3,4-tetrahydronaphthalen-1-amine 26

Compound 1a (1.37 g, 5.31 mmol) and the crude compound 26b (1.21 g, 6.16 mmol) was dissolved in 50 mL of dichloroethane, a drop of acetic acid was added, and the reaction was stirred for 1 hour. Sodium triacetoxyborohydride (2.81 g, 13.27 mmol) was added, and the reaction was stirred for 16 hours. The reaction solution was added with 10 mL of saturated sodium carbonate solution and stirred for 5 minutes. Then, 10 mL of 15% sodium hydroxide solution, 30 mL of water, and 30 mL of dichloromethane were added successively, and the mixture was stirred for 5 minutes. Two phases were separated, and the aqueous phase was extracted with dichloromethane (50 mL×2). The organic phases were combined, dried over anhydrous sodium sulfate, and filtered. The filtrate was concentrated under reduced pressure, and the resulting residue was purified by silica gel column chromatography with elution system A to obtain the title compound 26 (1.7 g, yield 73%) as a light yellow liquid.

MS m/z (ESI): 440.5 [M+1]; and $^1$H NMR (400 MHz, CDCl$_3$) δ 0.70 (dt, 1H), 1.09-1.16 (m, 1H), 1.45-1.55 (m, 4H), 1.62-1.84 (m, 6H), 1.86-2.04 (m, 4H), 2.23 (td, 1H), 2.34 (dd, 1H), 2.44 (dd, 1H), 2.53 (td, 1H), 3.68 (br. s., 1H), 3.72-3.81 (m, 2H), 4.34 (t, 1H), 7.11 (ddd, 1H), 7.17 (t, 2H), 7.18-7.23 (m, 1H), 7.31 (t, 2H), 7.62 (td, 1H), 8.55 (dd, 1H).

Example 27

(S)-4-ethyl-N-(2-((R)-9-(pyridin-2-yl)-6-oxaspiro[4.5]decan-9-yl)ethyl)-1,2-dihydronaphthalen-1-amine 27

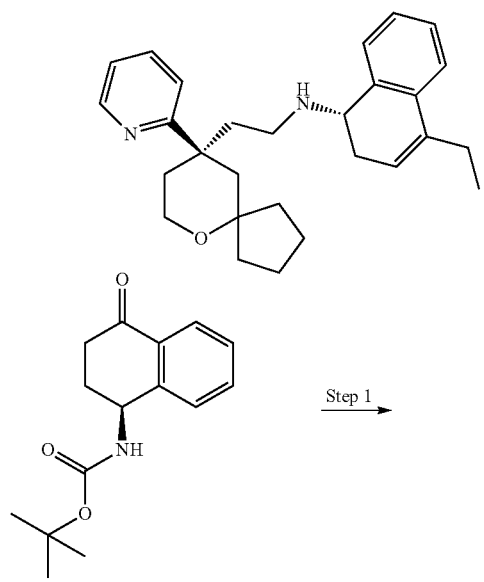

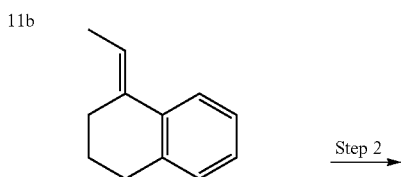

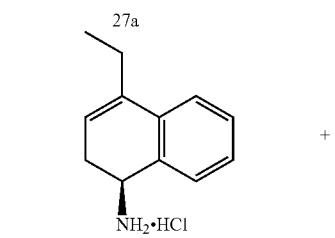

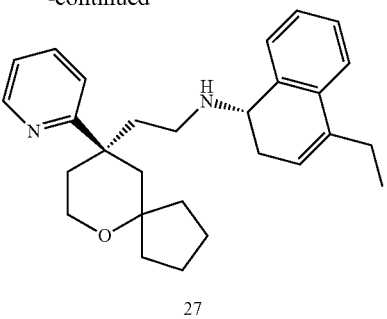

Step 1

(S,E)-tert-butyl (4-ethylidene-1,2,3,4-tetrahydronaphthalen-1-yl)carbamate 27a

Ethyltriphenylphosphonium bromide (2.1 g, 5.75 mmol) was dissolved in 20 mL of tetrahydrofuran. Potassium tert-butoxide (643 mg, 5.75 mmol) was added in an ice-water bath, and the reaction was stirred for 30 minutes in an ice-water bath. A pre-prepared solution of compound 11b (1 g, 3.83 mmol) in tetrahydrofuran was added dropwise, and the mixture was stirred for 16 hours at 25° C. The reaction solution was concentrated under reduced pressure, and the resulting residue was purified by thin layer chromatography with elution system B to obtain the title compound 27a (530 mg, yield 51%) as a light yellow oil.

Step 2

(S)-4-ethyl-1,2-dihydronaphthalen-1-amine hydrochloride 27b

Compound 27a (273 mg, 1 mmol) was dissolved in 5 mL of dichloromethane, then 2 mL of a solution of 4M hydrogen chloride in 1,4-dioxane was added. After stirring for 1 hour, the reaction solution was concentrated under reduced pressure to obtain the crude title compound 27b (173 mg) as a brown oil, which was used directly in the next step without further purification.

Step 3

(S)-4-ethyl-N-(2-((R)-9-(pyridin-2-yl)-6-oxaspiro[4.5]decan-9-yl)ethyl)-1,2-dihydronaphthalen-1-amine 27

Compound 1a (150 mg, 0.58 mmol) and the crude compound 27b (158 mg, 0.58 mmol) were dissolved in 30 mL of a mixture of dichloroethane and methanol (V:V=10:1), then sodium triacetoxyborohydride (369 mg, 1.74 mmol) was added. After stirring for 16 hours, the reaction solution was concentrated under reduced pressure, and the resulting residue was purified by thin layer chromatography with elution system A to obtain the title compound 27 (40 mg, yield 17%) as a light yellow solid.

MS m/z (ESI): 417.2 [M+1]; and $^1$H NMR (400 MHz, DMSO-$d_6$) δ 8.58 (d, 1H), 7.83-7.78 (m, 1H), 7.53-7.48 (m, 3H), 7.33-7.29 (m, 2H), 7.21 (d, 1H), 5.84 (t, 1H), 4.25 (t, 1H), 3.73-3.72 (m, 3H), 3.41-3.31 (m, 2H), 2.81-2.80 (m, 2H), 2.41-2.25 (m, 3H), 1.96-1.90 (m, 3H), 1.85-1.61 (m, 8H), 1.25 (t, 3H), 1.23-1.21 (m, 1H), 0.68-0.65 (m, 1H).

Example 28

(S)-4-methylene-N-(2-((R)-9-(pyridin-2-yl)-6-oxaspiro[4.5]decan-9-yl)ethyl)-1,2,3,4-tetrahydronaphthalen-1-amine 28

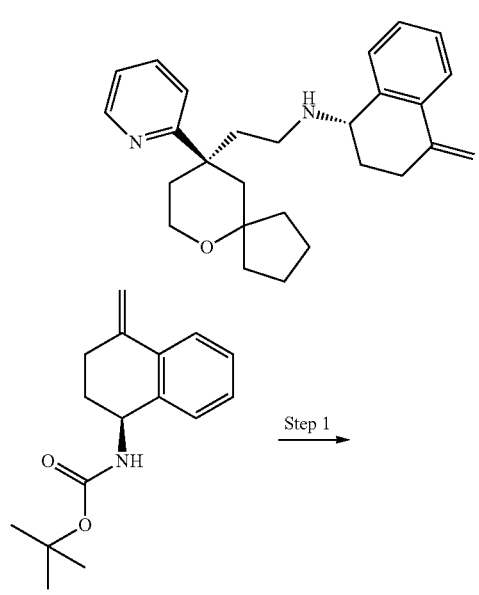

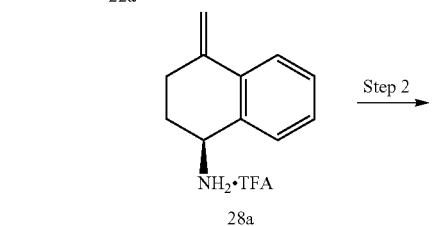

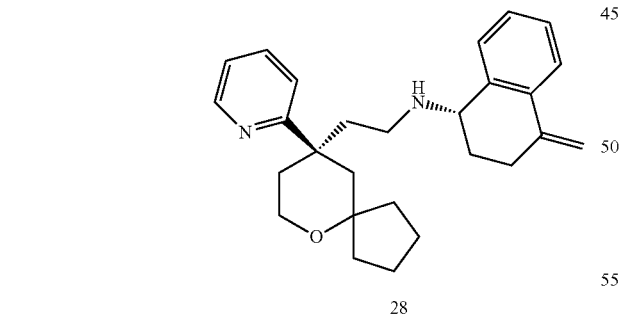

In accordance with the synthetic route of Example 17, the starting material 17a was replaced with compound 22a. Accordingly, the title compound 28 (20 mg) was prepared as a brown solid.

MS m/z (ESI): 403.5 [M+1]

$^1$H NMR (400 MHz, DMSO-d$_6$) δ 8.50 (d, 1H), 7.72 (t, 1H), 7.68-7.21 (m, 6H), 5.95 (d, 1H), 4.09 (d, 1H), 3.71-3.69 (m, 3H), 3.01-2.80 (m, 2H), 2.67-2.63 (m, 2H), 2.11 (d, 1H), 1.74-1.21 (m, 14H), 0.99-0.98 (m, 1H), 0.45-0.42 (m, 1H).

Example 29

2-(((1S,4S)-4-((2-((R)-9-(pyridin-2-yl)-6-oxaspiro[4.5]decan-9-yl)ethyl)amino)-1,2,3,4-tetrahydronaphthalen-1-yl)oxy)acetonitrile 29

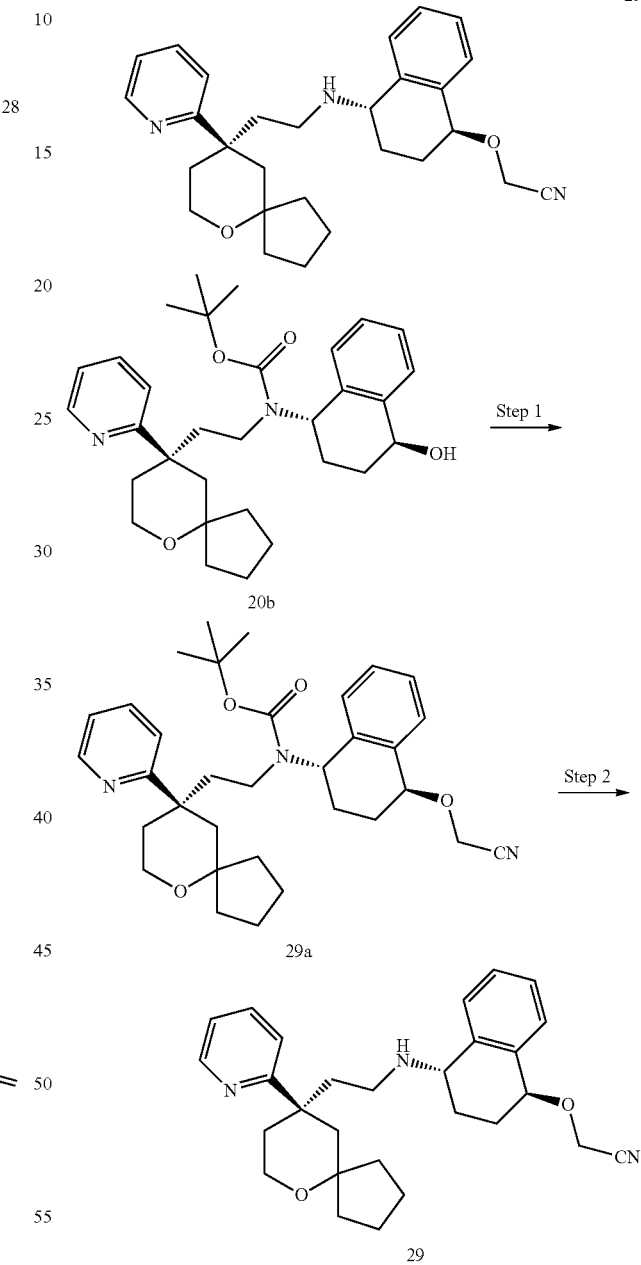

Step 1 tert-butyl ((1S,4S)-4-(cyanomethoxy)-1,2,3,4-tetrahydronaphthalen-1-yl)(2-((R)-9-(pyridin-2-yl)-6-oxaspiro[4.5]decan-9-yl)ethyl)carbamate 29a Compound 20b (40 mg, 0.08 mmol) was dissolved in 10 mL of tetrahydrofuran, then potassium tert-butoxide (45 mg, 0.4 mmol) and bromoacetonitrile (20 mg, 0.16 mmol) were added successively, and the reaction was stirred for 16 hours. Then, 20 mL of water and 20 mL of ethyl acetate were added and stirred. The mixture was left to stand and separate, and extracted with ethyl acetate (30 mL×2). The organic phases were combined and concentrated under reduced pressure to obtain the crude title compound 29a (50 mg) as an oil, which was used directly in the next step without further purification.

Step 2

2-(((1S,4S)-4-((2-((R)-9-(pyridin-2-yl)-6-oxaspiro[4.5]decan-9-yl)ethyl)amino)-1,2,3,4-tetrahydronaphthalen-1-yl)oxy)acetonitrile 29

The crude compound 29a (50 mg, 0.1 mmol) was dissolved in 10 mL of dichloromethane, then 0.1 mL of a solution of 4 M hydrogen chloride in dioxane was added. The reaction was stirred for 0.5 hour. Aqueous ammonia was added until the reaction solution was alkaline. The mixture was concentrated under reduced pressure, and the resulting residue was purified by thin layer chromatography with elution system A to obtain the title compound 29 (10 mg, yield 8%) as a white wax.

MS m/z (ESI): 446.3 [M+1]

$^1$H NMR (400 MHz, DMSO-$d_6$) δ 8.54 (d, 1H), 7.75-7.72 (m, 1H), 7.43 (d, 1H), 7.37-7.32 (m, 2H), 7.28-7.15 (m, 3H), 4.67 (d, 1H), 4.40 (d, 2H), 4.31 (d, 1H), 3.97 (d, 1H), 3.63-3.51 (m, 2H), 2.41-2.25 (m, 2H), 2.16-2.06 (m, 2H), 2.04-1.87 (m, 2H), 1.86-1.72 (m, 4H), 1.62-1.21 (m, 8H), 1.04-0.94 (m, 1H), 0.68-0.61 (m, 1H).

Example 30

(1S,4R)-4-methoxy-N-(2-((R)-9-(pyridin-2-yl)-6-oxaspiro[4.5]decan-9-yl)ethyl)-1,2,3,4-tetrahydronaphthalen-1-amine 30

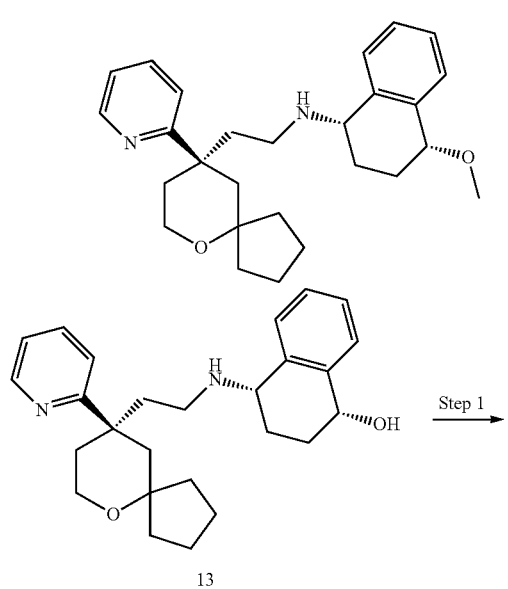

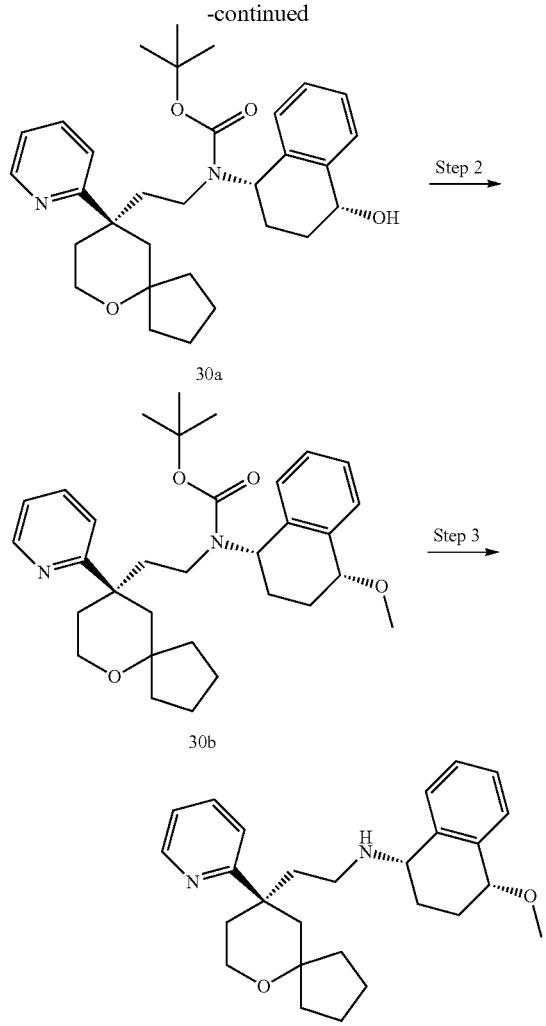

Step 1 tert-butyl ((1S,4R)-4-hydroxy-1,2,3,4-tetrahydronaphthalen-1-yl)(2-((R)-9-(pyridin-2-yl)-6-oxaspiro[4.5]decan-9-yl)ethyl)carbamate 30a Compound 13 (46 mg, 0.11 mmol), di-tert-butyl dicarbonate (27 mg, 0.121 mmol) and triethylamine (23 mg, 0.22 mmol) were dissolved in 15 mL of dichloromethane, and the reaction was stirred for 16 hours. The reaction solution was concentrated under reduced pressure, and the resulting residue was purified by thin layer chromatography with elution system A to obtain the title compound 30a (46 mg, yield 82%) as a white solid.

MS m/z (ESI): 507.3 [M+1].

Step 2 tert-butyl ((1S,4R)-4-methoxy-1,2,3,4-tetrahydronaphthalen-1-yl)(2-((R)-9-(pyridin-2-yl)-6-oxaspiro[4.5]decan-9-yl)ethyl)carbamate 30b Compound 30a (46 mg, 0.091 mmol) was dissolved in 10 mL of tetrahydrofuran, then sodium hydride (8 mg, 0.182 mmol) was added. The reaction was stirred for 30 minutes at room temperature. Iodomethane (16 mg, 0.11 mmol) was added, and the reaction was stirred for 16 hours at room temperature. Then, 50 mL of water and 50 mL of ethyl acetate were added, and two phases were separated. The organic phase was concentrated under reduced pressure to obtain the crude title compound 30b (47 mg) as a brown solid, which was used directly in the next step without further purification.

MS m/z (ESI): 521.3 [M+1].

Step 3

(1S,4R)-4-methoxy-N-(2-((R)-9-(pyridin-2-yl)-6-oxaspiro[4.5]decan-9-yl)ethyl)-1,2,3,4-tetrahydronaphthalen-1-amine 30

The crude compound 30b (47 mg, 0.091 mmol) was dissolved in 10 mL of dichloromethane, then 0.1 mL of a solution of 4 M hydrogen chloride in 1,4-dioxane was added, and the reaction was stirred for 1 hour. The reaction solution was concentrated under reduced pressure. Ethanol was added to the residue, and the pH was adjusted to 8 by aqueous ammonia. The mixture was concentrated under reduced pressure, and the resulting residue was purified by thin layer chromatography with elution system A to obtain the title compound 30 (36 mg, yield 95%) as a yellow viscous material.

MS m/z (ESI): 421.3 [M+1]; and
$^1$H NMR (400 MHz, DMSO-$d_6$) δ 8.55 (d, 1H), 7.75-7.72 (m, 1H), 7.46 (d, 1H), 7.37-7.32 (m, 2H), 7.28-7.15 (m, 3H), 4.67 (d, 1H), 4.30 (d, 1H), 3.97 (d, 1H), 3.64-3.50 (m, 2H), 3.35 (s, 3H), 2.41-2.26 (m, 2H), 2.16-2.06 (m, 2H), 2.04-1.87 (m, 2H), 1.86-1.72 (m, 4H), 1.62-1.21 (m, 8H), 1.04-0.94 (m, 1H), 0.68-0.61 (m, 1H).

Example 31

2-((S,E)-4-((2-((R)-9-(pyridin-2-yl)-6-oxaspiro[4.5]decan-9-yl)ethyl)amino)-3,4-dihydronaphthalen-1(2H)-ylidene)acetonitrile 31

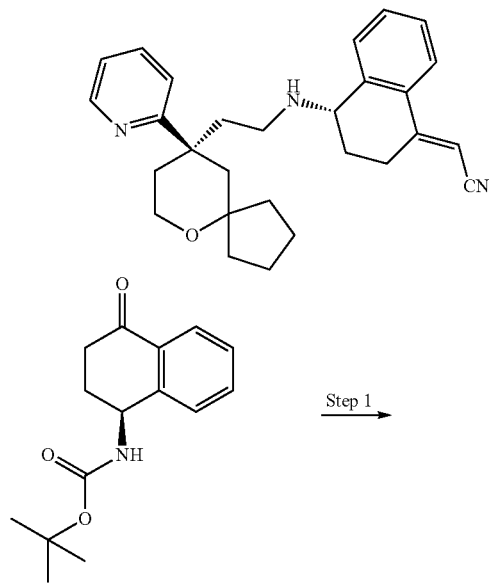

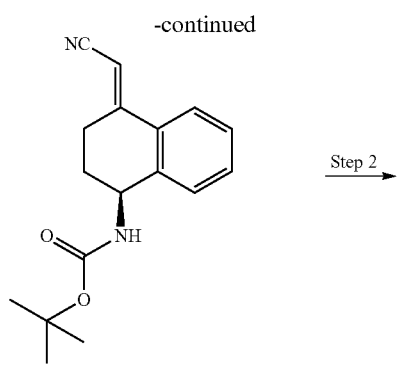

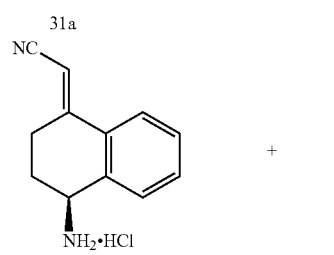

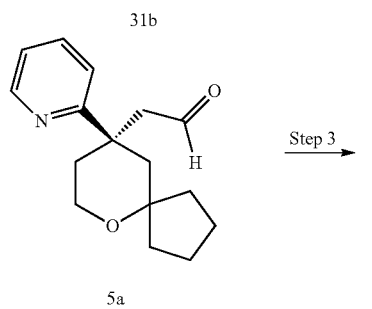

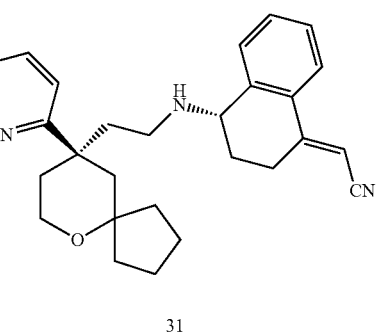

Step 1

(S,E)-tert-butyl (4-(cyanomethylene)-1,2,3,4-tetrahydronaphthalen-1-yl)carbamate 31a Diethyl cyanomethylphosphonate (200 mg, 0.76 mmol) was dissolved in 20 mL of tetrahydrofuran. Sodium hydride (61 mg, 1.52 mmol) was added in an ice-water bath, and the reaction was stirred for 30 minutes in an ice-water bath. A pre-prepared solution of compound 11b (200 mg, 0.76 mmol) in tetrahydrofuran was added dropwise, and the mixture was stirred for 16 hours at 25° C. The reaction solution was poured into ice-water and extracted with ethyl acetate three times. The organic phases were combined, dried over anhydrous sodium sulfate and filtered. The filtrate was concentrated under reduced pressure, and the resulting residue was purified by thin layer chromatography with elution system B to obtain the title compound 31a (150 mg, yield 69%) as a colorless viscous material.

MS m/z (ESI): 285.1 [M+1].

Step 2

(S,E)-2-(4-amino-3,4-dihydronaphthalen-1 (2H)-ylidene)acetonitrile hydrochloride 31b Compound 31a (150 mg, 0.52 mmol) was dissolved in 5 mL of dichloromethane, then 2 mL of a solution of 1M hydrochloric acid in 1,4-dioxane were added. The reaction was stirred for 3 hours. The reaction solution was concentrated under reduced pressure to obtain the crude title compound 31b (110 mg) as a white solid, which was used directly in the next step without further purification.

Step 3

2-((S,E)-4-((2-((R)-9-(pyridin-2-yl)-6-oxaspiro[4.5]decan-9-yl)ethyl)amino)-3,4-dihydronaphthalen-1 (2H)-ylidene)acetonitrile 31

Compound 5a (100 mg, 0.39 mmol) and the crude compound 31b (85 mg, 0.39 mmol) were dissolved in 10 mL of a mixture of dichloroethane and methanol (V:V=10:1), then sodium triacetoxyborohydride (165 mg, 0.78 mmol) was added, and the reaction was stirred for 16 hours. The reaction solution was concentrated under reduced pressure, and the resulting residue was purified by thin layer chromatography with elution system A to obtain the title compound 31 (30 mg, yield 18%) as a light yellow viscous material.

MS m/z (ESI): 428.0 [M+1]; and $^1$H NMR (400 MHz, DMSO-d$_6$) δ 8.57 (d, 1H), 7.86-7.78 (m, 1H), 7.76-7.74 (m, 1H), 7.39-7.22 (m, 3H), 7.26-7.23 (m, 2H), 6.36-6.35 (m, 1H), 3.65-3.54 (m, 3H), 2.90-2.60 (m, 2H), 2.42-2.37 (m, 3H), 2.03-1.90 (m, 4H), 1.82-1.78 (m, 2H), 1.51-1.24 (m, 10H).

Example 32

2-((4S)-4-((2-((R)-9-(pyridin-2-yl)-6-oxaspiro[4.5]decan-9-yl)ethyl)amino)-1,2,3,4-tetra hydronaphthalen-1-yl)acetonitrile 32

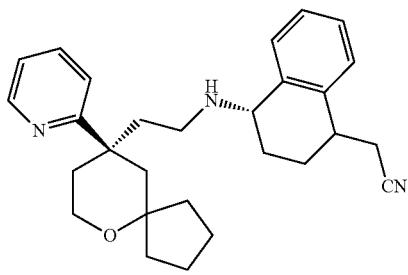

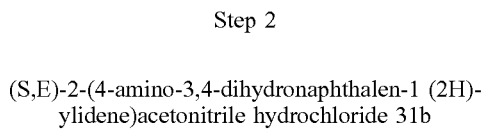

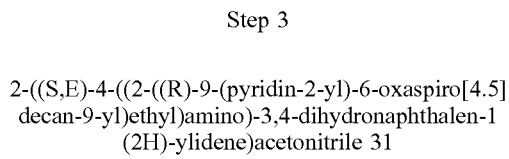

Step 1

2-((4S)-4-amino-1,2,3,4-tetrahydronaphthalen-1-yl)acetonitrile hydrochloride 32a Compound 31b (50 mg, 0.227 mmol) was dissolved in 5 mL of ethanol, then 5 mg of Pd/C was added, and the reaction system was purged with hydrogen three times. The reaction was stirred for 16 hours at room temperature under a hydrogen atmosphere. Insolubles were removed by filtration, and the filtrate was concentrated under reduced pressure to obtain the crude title compound 32a (45 mg) as a colorless viscous material, which was used directly in the next step without further purification.

Step 2

2-((4S)-4-((2-((R)-9-(pyridin-2-yl)-6-oxaspiro[4.5]decan-9-yl)ethyl)amino)-1,2,3,4-tetra hydronaphthalen-1-yl)acetonitrile 32

Compound 5a (53 mg, 0.2 mmol) and the crude compound 32b (25 mg, 0.2 mmol) were dissolved in 10 mL of a mixture of dichloroethane and methanol (V:V=10:1). Then, sodium triacetoxyborohydride (80 mg, 0.4 mmol) was added, and the reaction was stirred for 16 hours. The reaction solution was concentrated under reduced pressure, and the resulting residue was purified by thin layer chromatography with elution system A to obtain the title compound 32 (5 mg, yield 5.8%) as a light yellow viscous material.

MS m/z (ESI): 430.3 [M+1]; and $^1$H NMR (400 MHz, DMSO-d$_6$) δ 8.55 (d, 1H), 7.85-7.78 (m, 1H), 7.75-7.72 (m, 1H), 7.35-7.20 (m, 3H), 7.25-7.21

(m, 2H), 3.75-3.60 (m, 3H), 2.95-2.80 (m, 2H), 2.70-2.65 (m, 4H), 2.41-2.30 (m, 4H), 1.95-1.89 (m, 4H), 1.85-1.60 (m, 4H), 1.55-1.21 (m, 6H).

Example 33

(S)—N-(2-((R)-9-(pyridin-2-yl)-6-oxaspiro[4.5]decan-9-yl)ethyl)-3,4-dihydro-2H-spiro[[1,3]dioxolane-2,1'-naphthalen]-4'-amine 33

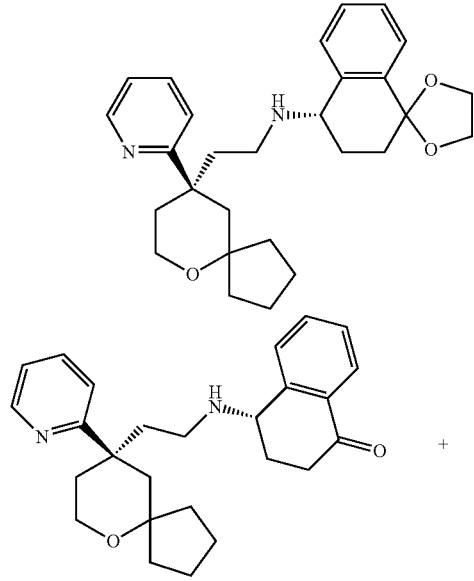

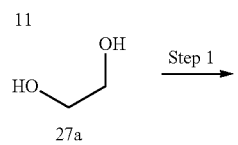

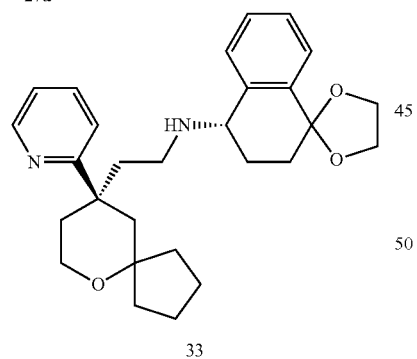

In accordance with the synthetic route of Example 27, the starting material 2 was replaced with compound 11. Accordingly, the title compound 33 (5 mg) was prepared as a yellow oil.

MS m/z (ESI): 449.0[M+1]; and $^1$H NMR (400 MHz, DMSO-d$_6$): δ 8.58 (d, 1H), 7.81 (s, 1H), 7.77-7.70 (m, 1H), 7.51 (d, 1H), 7.27-7.11 (m, 4H), 3.85 (s, 1H), 3.66-3.50 (m, 5H), 3.51-3.42 (m, 1H), 3.42-3.33 (m, 1H), 2.48-2.35 (m, 2H), 2.38-2.32 (m, 1H), 2.20-2.08 (m, 2H), 2.01-1.88 (m, 2H), 1.85-1.75 (m, 3H), 1.71-1.31 (m, 8H), 1.00-0.96 (m, 1H), 0.70-0.62 (m, 1H).

Example 34

(1S,4S)-4-propoxy-N-(2-((R)-9-(pyridin-2-yl)-6-oxaspiro[4.5]decan-9-yl)ethyl)-1,2,3,4-tetrahydronaphthalen-1-amine 34

In accordance with the synthetic route of Example 21, the starting material 1-bromo-2-fluoroethane was replaced with iodopropane. Accordingly, the title compound 34 (8 mg) was prepared as a yellow solid.

MS m/z (ESI): 449.3 [M+1]; and $^1$H NMR (400 MHz, DMSO-d$_6$) δ 8.53 (d, 1H), 7.75-7.70 (m, 1H), 7.45 (d, 1H), 7.37-7.33 (m, 2H), 7.28-7.17 (m, 3H), 4.65 (d, 1H), 4.32 (d, 1H), 3.98 (d, 1H), 3.64-3.52 (m, 3H), 3.49-3.40 (m, 1H), 2.62-2.52 (m, 1H), 2.41-2.27 (m, 2H), 2.16-2.06 (m, 1H), 2.04-1.87 (m, 2H), 1.86-1.71 (m, 5H), 1.67 (d, 1H), 1.60-1.20 (m, 8H), 1.13 (t, 3H), 1.03-0.95 (m, 1H), 0.68-0.60 (m, 1H).

BIOLOGICAL ASSAY

The present invention is further described with reference to the following test examples, but the examples should not be considered as limiting the scope of the invention.

Test Example 1

1. Experimental Objective

The objective of this experiment is to determine the agonistic effect of the compounds of the present invention on MOR, KOR, DOR, and to evaluate the in vitro activity of the compounds according to the values of $EC_{50}$ and Emax.

2. MOR Activity Test 2.1 Experimental Objective

The compounds of the present invention can activate μ-opioid receptors (MOR). Activated MOR can regulate intracellular cAMP levels, and cAMP enters the nucleus and binds to the CRE region of the reporter gene luciferase, thereby initiating the expression of the reporter gene. Luciferase can react with its substrate to emit fluorescence, and the measured fluorescence signals reflect the agonistic activity of the compounds.

2.2 Experimental Method

The activity of the test example compounds on agonizing MOR and affecting downstream cAMP levels was tested by the following method.

2.1.1 Experimental Materials

| Reagent name | Supply company | Item number |
|---|---|---|
| HEK293 cell line | Cell bank of the typical culture preservation Committee of Chinese Academy of Sciences | GNHu43 |
| DMSO | Shanghai Titanchem | G75927B |
| DMEM high glucose medium | Thermo HyCLone | SH30243018 |
| Fetal bovine serum (FBS) | Gibco | 10099-141 |
| CRE/pGL4.29 | Promega | E8471 |
| MOR-1/pcDNA3.1(+) | GENEWIZ Biological Technology Co., Ltd | Synthesis |
| ONE-Glo Luciferase Assay System | Promega | E6110 |

2.2.2 Experimental Procedure

1) Obtaining HEK293/MOR/CRE monoclonal cell lines MOR/pcDNA3.1 (+) and CRE/pGL4.29 were transferred into HEK293 cells. G418 and hygromycin were added into the culture medium, and HEK293/MOR/CRE monoclonal cell lines were screened in a 96-well cell culture plate.

2) Agonistic effect of example compounds on MOR HEK293/MOR/CRE monoclonal cells were cultured in a DMEM/high glucose medium (10% FBS, 1 mg/ml G418, 200 μg/ml hygromycin, mixed uniformly), and passaged every 3 days. On the day of the experiment, a cell suspension was prepared with a fresh cell medium, added to a 96 well plate (BD, #356692) with 20,000 cells/well, and incubated in 5% $CO_2$ at 37° C. On the second day, the compound was dissolved in pure DMSO at a concentration of 20 mM, then formulated with DMSO to a first concentration of 4 mM and diluted in 10 fold concentration gradient to 6 concentrations. Then, 90 μl of DMSO was added to blank and control wells. Then, formulated compound was prepared by adding 2.5 μl of the compound solutions formulated in DMSO at a gradient concentration to 97.5 μl of a fresh cell culture medium containing 5 μM foscolin. Then, 10 μl of the formulated compound was added to the cell culture plate to make the final concentration of the compound 10000, 1000, 100, 10, 1, 0.1, or 0.01 nM, and the plate was incubated at 37° C., in 5% $CO_2$ for 5 hours. In a 96-well cell culture plate, 100 μl of luciferase assay solution (Promega, # E6110) was added to each well. The plate was placed in the dark at room temperature for 10-15 minutes, blowed and aspirated 10 times, and 100 μl were pipetted to a 96 well white plate. The chemiluminescence signal values were read in a microplate reader (PE, Victor3), and the read data was processed using software.

2.3 Test Results

The activity of the compounds of the present invention on agonizing MOR and affecting downstream cAMP levels was determined by the above test, and the $EC_{50}$ values are shown in Table 1.1. Emax is the maximum effect of the example compound on activating MOR and affecting the cAMP signaling pathway (the maximum effect of TRV-130 is 100%).

3. KOR and DOR Activity Test 3.1 Experimental Objective

The experiment objective is to determine the activity of the compounds of the present invention on agonizing KOR receptor and DOR receptor, and affecting downstream cAMP levels.

3.2 Experimental Procedure

90 μl of HEK293/KOR/CRE or HEK293/DOR/CRE (CRE cDNA purchased from Promega, product number E8471, KOR cDNA and DOR cDNA were constructed by our company) cells were inoculated in a 96-well plate with a density of $1\times10^4$ cells/well. Then, the cells were incubated overnight at 37° C., in 5% $CO_2$. The drug was prepared as a 20 mM stock solution that was later diluted with 100% DMSO to a 200×concentration gradient, and then diluted with a 20-fold DMEM/high glucose (SH30243.01B, Hyclone) medium. The cell culture plate inoculated on the first day was taken out, and 10 l of the diluted drug or control (0.5% DMSO) was added to each well. The plate was gently shaken and placed in a incubator at 37° C., 5% $CO_2$ for 4 hours. Finally, 100 μl of a detection reagent ONE-Glo (E6120, Promega) was added to each well, and the plate was placed at room temperature for 5 minutes. The absorbance value was measured by the cold light model of a microplate reader (PE, Victor3). The $EC_{50}$ value of the compound was calculated by Graphpad Prism software according to each concentration of the compound and the corresponding signal value. Emax is the maximum effect of the compound on cAMP level changes.

3.3 Test Results

The activity of the compounds of the present invention on agonizing KOR receptor or DOR receptor and affecting downstream cAMP levels was determined by the above test, and the $EC_{50}$ values are shown in Table 1.2. Emax is the maximum effect of the example compound on affecting cAMP levels (The maximum effect of morphine is 100%).

TABLE 1.1

$EC_{50}$ and Emax values of the compounds of the present invention on agonizing MOR receptor and affecting cAMP levels

| | MOR | |
|---|---|---|
| Example No. | $EC_{50}$(nM) | Emax |
| 1 | 10 | 102% |
| 2 | >10000 | 0 |
| 3 | 2 | 124% |
| 4 | 1 | 129% |
| 5 | 5 | 122% |
| 6 | 1 | 115% |
| 7 | >10000 | 0 |
| 8 | 3 | 114% |
| 9 | >10000 | 48% |
| 10 | 4 | 113% |
| 11 | 17 | 112% |
| 12 | 2 | 125% |
| 13 | 8 | 130% |
| 14 | 3 | 109% |
| 15 | >10000 | 0 |
| 16 | 9 | 122% |
| 17 | >10000 | 0 |
| 18 | >10000 | 4% |
| 19 | 2 | 98% |
| 21 | 5 | 110% |
| 22 | 4 | 103% |
| 23 | 5 | 120% |
| 24 | 0.8 | 102% |
| 29 | 7 | 112% |
| 30 | 2 | 126% |
| 32 | 0.8 | 133% |

TABLE 1.2

$EC_{50}$ and Emax values of the compounds of the present invention on agonizing KOR receptor and DOR receptor and affecting downstream cAMP levels

| | KOR | | DOR | |
|---|---|---|---|---|
| Example No. | $EC_{50}$(nM) | Emax | $EC_{50}$(nM) | Emax |
| 11 | 277 | 98% | 1916 | 80% |
| 14 | 1469 | 74% | 1507 | 91% |
| 19 | 862 | 96% | 552 | 108% |
| 20 | 710 | 103% | 1525 | 118% |
| 21 | 1184 | 100% | 1487 | 107% |
| 22 | 3091 | 97% | 2404 | 102% |

Conclusion

The agonist activity of the compounds of the present invention on KOR receptor or DOR receptor is obviously weak, and the compounds of the present invention have high selectivity for MOR receptor.

Test Example 2

1. Experimental Objective

The experiment objective is to determine the activity of the compounds of the present invention on activating the β-arrestin signaling pathway of MOR receptor.

2. Experimental Method 2.1 Experiment Procedure

90 μl of CHO-K1 OPRM1 β-Arrestin (93-0213C2, DiscoveRX) cells were inoculated in a 96-well plate with a density of 1×10⁴ cells/well, then the cells were incubated overnight at 37° C., in 5% $CO_2$. The drug was prepared as a 20 mM stock solution that was later diluted with 100% DMSO to a 200×concentration gradient, and then diluted with a 20-fold AssayComplete™ Cell Plating 2 Reagent (93-0563R2B, DiscoveRX) medium. The cell culture plate inoculated on the first day was taken out, and 10 μl of the diluted drug or control (0.5% DMSO) was added to each well. The plate was gently shaken and placed in an incubator at 37° C., 5% $CO_2$ for 90 minutes. Finally, 50 μL of a detection reagent (93-0001, DiscoveRX) were added to each well, and the plate was placed at room temperature for 60 minutes. The absorbance values were measured by the cold light model of a microplate reader (PE, Victor3). The $EC_{50}$ values of the compounds were calculated by Graphpad Prism software according to each concentration of the compound and the corresponding signal value.

2.2 Test Results

The activity of the compounds of the present invention on activating the β-arrestin signaling pathway was determined by the above assay, and the $EC_{50}$ values are shown in Table 2. Emax is the maximum effect of the compound on affecting the β-arrestin signaling pathway (The maximum effect of morphine is 100%).

TABLE 2

$EC_{50}$ values of the compounds of the present invention on the β-arrestin signaling pathway

| Example No. | $EC_{50}$(nM) | Emax |
|---|---|---|
| 1 | 4 | 12% |
| 2 | >10000 | 4% |
| 11 | 305 | 37% |
| 14 | 26 | 24% |
| 16 | 94 | 9% |
| 19 | 24 | 13% |
| 20 | 4 | 9% |
| 22 | 41 | 18% |
| 24 | 6 | 30% |
| 28 | 15 | 22% |
| 29 | 33 | 32% |
| 33 | 73 | 27% |
| 34 | 16 | 10% |

Conclusion

The compounds of the present invention have little activation effect on the β-arrestin signaling pathway Test Example 3

1. Experimental Objective

The blocking effect of the compounds of the present invention and the positive compound TRV-130 (*Journal of Pharmacology and Experimental Therapeutics*, Volume 344, Issue 3, Pages 708-717, 2013) on hERG potassium current was tested on a stable cell line transfected with hERG potassium channel using an automatic patch clamp.

2. Experimental Method 2.1 Experimental Materials and Instruments 2.1.1 Experimental Materials:

| Reagent name | Supply company | Item number |
|---|---|---|
| FBS | GIBCO | 10099 |
| Sodium pyruvate solution | Sigma | S8636-100ML |
| MEM Non-essential amino acid solution (100×) | Sigma | M7145-100ML |
| G418 sulfate | Enzo | ALX-380-013-G005 |
| MEM | Hyclone | SH30024.01B |
| hERG cDNA | Origene | — |

2.1.2 Instruments

| Instrument name | Supply company | Model |
|---|---|---|
| Patchliner 4 channel | Nanion | 2-03-03100-002 |
| Patchliner cleaning station | Nanion | 2-02-03201-005 |
| Patchliner cell bank | Nanion | 2-02-03105-000 |
| Elektrodenchloridierer Patchliner | Nanion | 3-02-03533-000 |
| HEAR EPC10 Patch clamp amplifier | Nanion | 1-01-10012-000 |
| Osmotic pressure molar concentration analyzer | Gonoter | Gonoter 030 |
| pH meter | Mettler Toledo | FE20 |

2.2 Experimental Procedure of Automatic Patch Clamp

HEK293-hERG stabilized cells were subcultured at a density of 1:4 in a MEM/EBSS medium (10% FBS, 400 μg/ml G418, 1% MEM nonessential amino acid solution (100×), 1% sodium pyruvate solution) for 48-72 hours, then the automatic patch clamp experiment was performed. The cells were digested with 0.25% trypsin on the day of the experiment, then the cells were collected by centrifugation and resuspended with extracellular fluid (140 mM NaCl, 4 mM KCl, 1 mM $MgCl_2$, 2 mM $CaCl_2$, 5 mM D-glucose monohydrate, 10 mM Hepes, pH 7.4, 298 mOsmol) into a cell suspension. The cell suspension was placed on the cell bank of the Patchliner instrument, and the cells were added to the chip (NPC-16) by the negative pressure controller of the Patchliner instrument, with negative pressure attracting individual cells to the small hole of the chip. After the whole cell model was formed, the instrument generated the hERG current according to the preset hERG current and voltage program, and then the instrument perfused the compound from low concentration to high concentration automatically. HEAK Patchmaster, HEAK EPC10 patch clamp amplifier (Nanion), Pathliner software, and a data analysis software provided by Pathcontrol HTsoftware were used to analyze the current of the compounds at different concentrations and the current of the blank control.

2.3 Test Results

The blocking effect of the compounds of the present invention on hERG potassium current was determined by the above test, and the $IC_{50}$ values are shown in Table 3.

TABLE 3

$IC_{50}$ of the compounds of the present invention on blocking hERG potassium current

| Example No. | $IC_{50}(\mu M)$ |
|---|---|
| TRV-130 | 1.6 |
| 1 | 13 |
| 3 | >30 |
| 5 | 6.2 |
| 6 | 3.8 |
| 11 | 4.1 |
| 12 | 10.2 |
| 13 | 13.5 |
| 14 | 8.6 |
| 16 | 10 |
| 19 | 5.9 |
| 21 | 4.2 |
| 22 | 3.8 |
| 24 | 2.5 |

CONCLUSION

The compounds of the present invention have a weaker inhibitory effect on hERG than the positive control, and there is a significant difference.

What is claimed is:

1. A compound of formula (I):

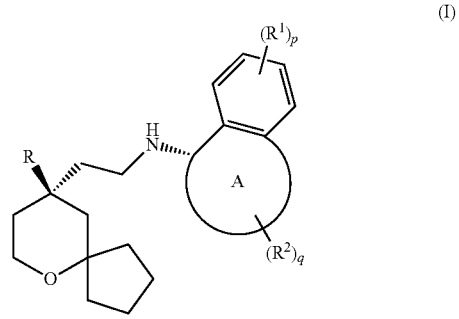

or a tautomer, mesomer, racemate, enantiomer, diastereomer thereof, or mixture thereof, or a pharmaceutically acceptable salt thereof, wherein:

ring A is selected from the group consisting of cycloalkyl and heterocyclyl;

R is selected from the group consisting of aryl and heteroaryl, wherein the aryl and heteroaryl are each optionally substituted by one or more groups selected from the group consisting of alkyl, haloalkyl, halogen, amino, nitro, cyano, alkoxy, haloalkoxy, hydroxyalkyl, cycloalkyl, heterocyclyl, aryl, heteroaryl, —$OR^3$, —$C(O)R^3$, —$C(O)OR^3$, —$S(O)_mR^3$ and —$NR^4R^5$;

each $R^1$ is identical or different and each is independently selected from the group consisting of hydrogen, alkyl, alkoxy, haloalkyl, halogen, amino, nitro, hydroxy, cyano, cycloalkyl, heterocyclyl, aryl, heteroaryl, —$OR^3$, —$C(O)R^3$, —$C(O)OR^3$, —$S(O)_mR^3$ and —$NR^4R^5$, wherein the alkyl, haloalkyl, cycloalkyl, heterocyclyl, aryl and heteroaryl are each optionally substituted by one or more groups selected from the group consisting of alkyl, haloalkyl, halogen, amino, nitro, cyano, hydroxy, alkoxy, haloalkoxy, hydroxyalkyl, cycloalkyl, heterocyclyl, aryl and heteroaryl;

each $R^2$ is identical or different and each is independently selected from the group consisting of hydrogen, alkyl, alkoxy, haloalkyl, halogen, amino, nitro, hydroxy, cyano, oxo, alkenyl, cycloalkyl, heterocyclyl, aryl, heteroaryl, —$OR^3$, —$C(O)R^3$, —$C(O)OR^3$, —$S(O)_mR^3$ and —$NR^4R^5$, wherein the alkyl, alkoxy, alkenyl, haloalkyl, cycloalkyl, heterocyclyl, aryl and heteroaryl are each optionally substituted by one or more groups selected from the group consisting of deuterium, alkyl, haloalkyl, halogen, amino, nitro, cyano, hydroxy, alkoxy, haloalkoxy, hydroxyalkyl, cycloalkyl, heterocyclyl, aryl and heteroaryl;

or two $R^2$ are taken together to form a cycloalkyl or heterocyclyl, wherein the cycloalkyl or heterocyclyl is each optionally substituted by one or more groups selected from the group consisting of alkyl, haloalkyl, halogen, amino, nitro, cyano, hydroxy, alkoxy, haloalkoxy, hydroxyalkyl, cycloalkyl, heterocyclyl, aryl and heteroaryl;

$R^3$ is selected from the group consisting of hydrogen, alkyl, deuterated alkyl, amino, alkoxy, hydroxyalkyl, cycloalkyl, heterocyclyl, aryl and heteroaryl, wherein the alkyl, cycloalkyl, heterocyclyl, aryl and heteroaryl are each optionally substituted by one or more groups selected from the group consisting of alkyl, halogen, hydroxy, amino, nitro, cyano, alkoxy, hydroxyalkyl, cycloalkyl, heterocyclyl, aryl and heteroaryl;

$R^4$ and $R^5$ are each independently selected from the group consisting of hydrogen, alkyl, alkoxy, hydroxyalkyl, hydroxy, amino, alkoxycarbonyl, cycloalkyl, heterocyclyl, aryl and heteroaryl, wherein the alkyl, cycloalkyl, heterocyclyl, aryl and heteroaryl are each optionally substituted by one or more groups selected from the group consisting of alkyl, halogen, hydroxy, amino, alkoxycarbonyl, nitro, cyano, alkoxy, hydroxyalkyl, cycloalkyl, heterocyclyl, aryl and heteroaryl;

p and q are each independently 0, 1, 2, 3 or 4; and m is 0, 1 or 2.

2. The compound according to claim 1, wherein ring A is selected from the group consisting of 5 to 6 membered heterocyclyl and 5 to 6 membered cycloalkyl.

3. The compound according to claim 1, wherein R is pyridyl.

4. The compound according to claim 1, being a compound of formula (II):

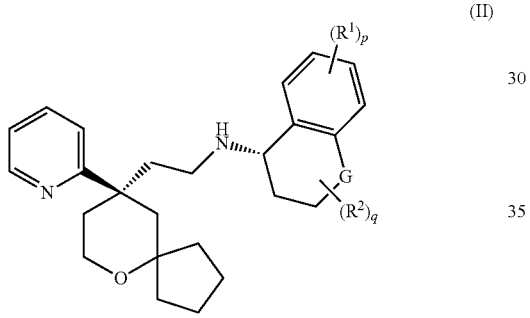

or a tautomer, mesomer, racemate, enantiomer, diastereomer thereof, or mixture thereof, or a pharmaceutically acceptable salt thereof,
wherein:
G is selected from the group consisting of a bond, $CR^aR^b$, C=O, $NR^4$ and oxygen;

$R^a$ and $R^b$ are each independently selected from the group consisting of hydrogen, alkyl, alkoxy, haloalkyl, halogen, amino, nitro, hydroxy, cyano, cycloalkyl, heterocyclyl, aryl, heteroaryl, $-OR^3$, $-C(O)R^3$, $-C(O)OR^3$, $-S(O)_mR^3$ and $-NR^4R^5$, wherein the alkyl, haloalkyl, cycloalkyl, heterocyclyl, aryl and heteroaryl are each optionally substituted by one or more groups selected from the group consisting of alkyl, haloalkyl, halogen, amino, nitro, cyano, hydroxy, alkoxy, haloalkoxy, hydroxyalkyl, cycloalkyl, heterocyclyl, aryl and heteroaryl;

or $R^a$ and $R^b$ are taken together to form a cycloalkyl or heterocyclyl, wherein the cycloalkyl or heterocyclyl is each optionally substituted by one or more groups selected from the group consisting of alkyl, haloalkyl, halogen, amino, nitro, cyano, hydroxy, alkoxy, haloalkoxy, hydroxyalkyl, cycloalkyl, heterocyclyl, aryl and heteroaryl; and $R^1$ to $R^5$, p, m and q are as defined in claim 1.

5. The compound according to claim 1, wherein $R^1$ is hydrogen or halogen.

6. The compound according to claim 1, wherein $R^2$ is selected from the group consisting of hydrogen, alkyl, oxo, alkoxy, hydroxy, halogen and $-OR^3$, wherein the alkyl and alkoxy are each optionally substituted by one or more groups selected from the group consisting of deuterium, alkyl, halogen, hydroxy, amino, alkoxycarbonyl, nitro, cyano, alkoxy, hydroxyalkyl, cycloalkyl, heterocyclyl, aryl and heteroaryl; and $R^3$ is selected from the group consisting of hydrogen, alkyl and cycloalkyl, wherein the alkyl is optionally substituted by halogen or cycloalkyl.

7. The compound according to claim 4, being a compound of formula (IV):

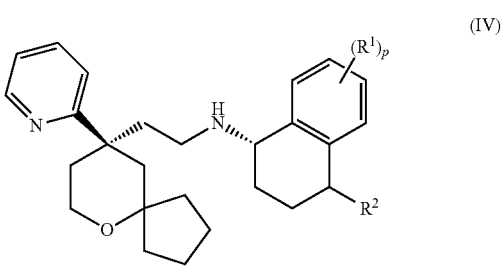

or a tautomer, mesomer, racemate, enantiomer, diastereomer thereof, or mixture thereof, or a pharmaceutically acceptable salt thereof, wherein $R^1$, $R^2$ and p are as defined in claim 4.

8. A compound selected from the group consisting of:

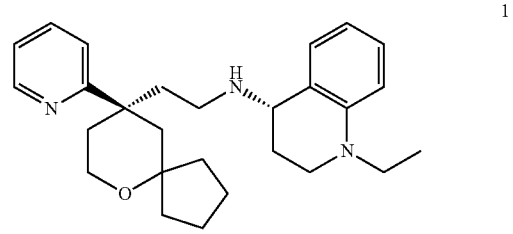

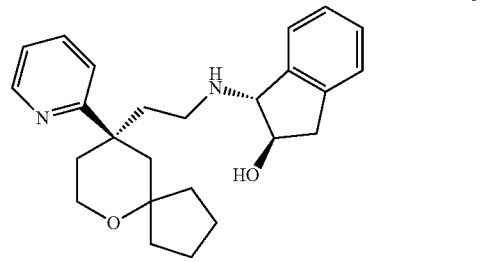

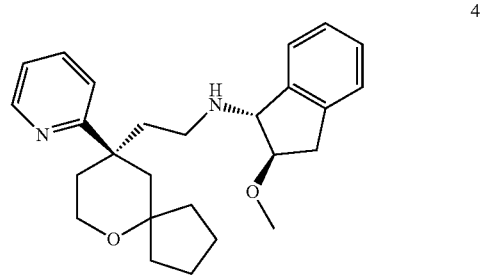

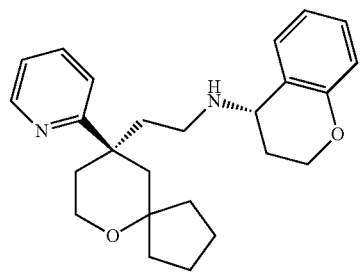
6
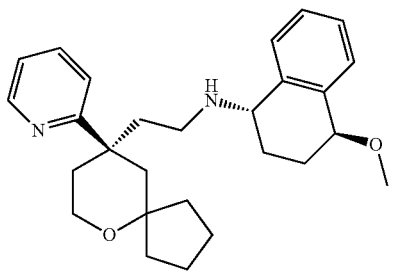
14
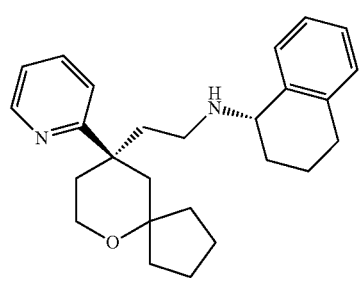
10
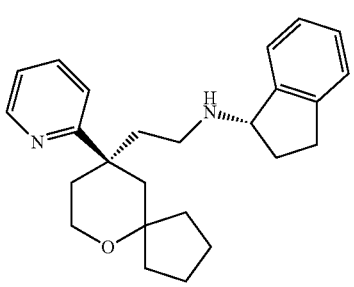
16
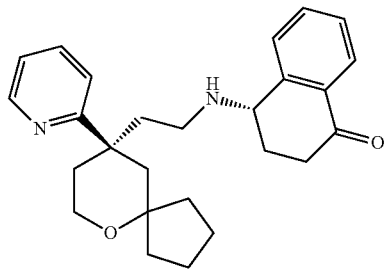
11
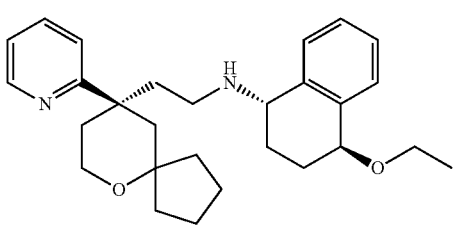
19
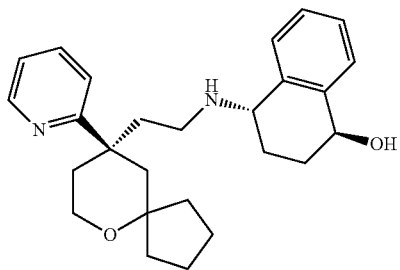
12
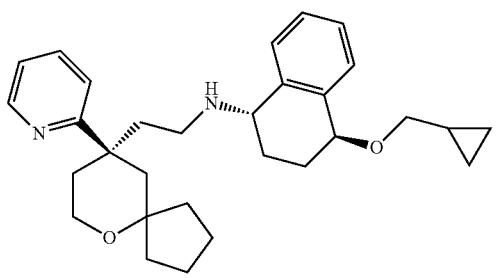
20
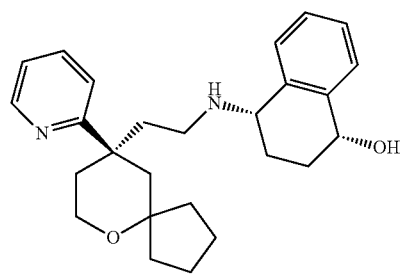
13
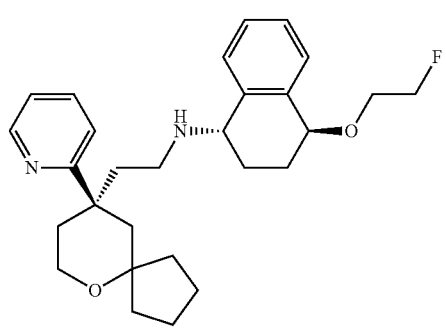
21

32

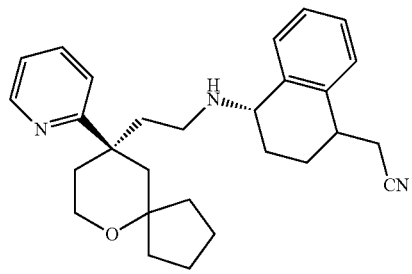

33

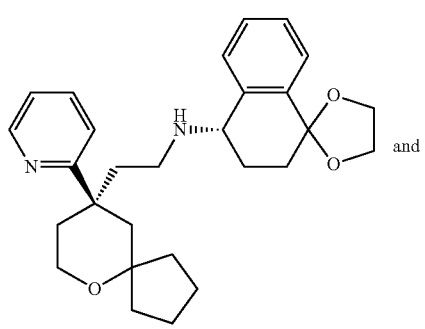 and

34

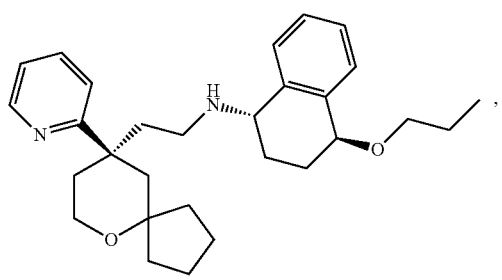, or a tautomer, mesomer, racemate, enantiomer, diastereomer thereof, or mixture thereof, or a pharmaceutically acceptable salt thereof.

9. A process for preparing the compound of formula (I) according to claim 1, comprising:

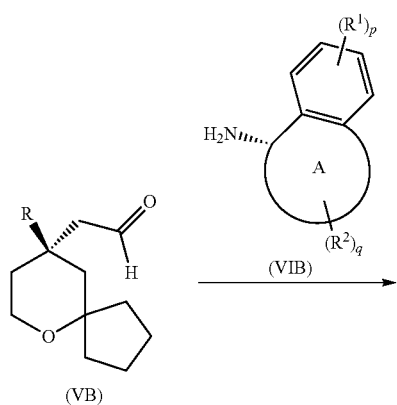

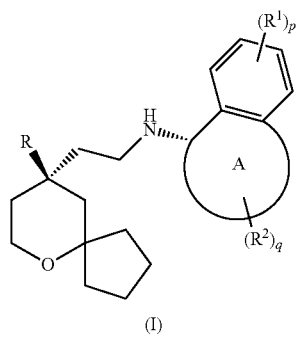

reacting a compound of formula (VB) with a compound of formula (VIB) or a hydrochloride thereof via a reductive amination to obtain the compound of formula (I);

wherein:

ring A, R, $R^1$, $R^2$, p and q are as defined in claim 1.

10. A pharmaceutical composition comprising a therapeutically effective amount of the compound according to claim 1, and one or more pharmaceutically acceptable carriers, diluents or excipients.

11. The compound according to claim 6, wherein $R^2$ is alkyl, wherein the alkyl is optionally substituted by alkoxy, cycloalkyl or haloalkyl; and $R^3$ is hydrogen, alkyl, haloalkyl or cycloalkyl.

12. A method of treating pain in a subject, the method comprising administering to the subject the pharmaceutical composition of claim 10.

13. The method according to claim 12, wherein the pain is selected from the group consisting of postoperative pain, pain induced by a cancer, neuropathic pain, traumatic pain and inflammatory pain.

14. The method according to claim 13, wherein the cancer is selected from the group consisting of breast cancer, endometrial cancer, cervical cancer, skin cancer, prostate cancer, ovarian cancer, fallopian tube tumor, ovarian tumor, hemophilia and leukemia.

15. A method of agonizing a MOR receptor in a subject, the method comprising administering to the subject the pharmaceutical composition of claim 10.

16. A pharmaceutical composition comprising a therapeutically effective amount of the compound according to claim 8, and one or more pharmaceutically acceptable carriers, diluents or excipients.

17. A method of treating pain in a subject, the method comprising administering to the subject the pharmaceutical composition of claim 16.

18. The compound according to claim 8, wherein the compound is

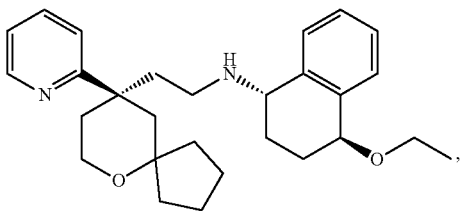

or a pharmaceutically acceptable salt thereof.

19. The compound according to claim 8, wherein the compound is selected from the group consisting of:

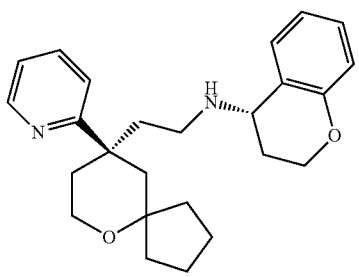

and

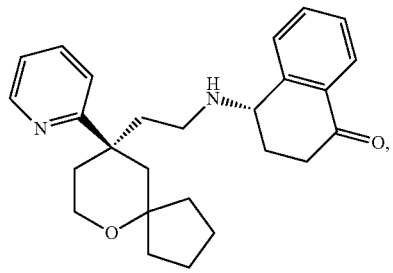

or a pharmaceutically acceptable salt thereof.

20. The compound according to claim 8, wherein the compound is selected from the group consisting of:

[Structures 19, 21, 22 shown]

or a pharmaceutically acceptable salt thereof.

21. A pharmaceutical composition comprising a therapeutically effective amount of the compound according to claim 18, and one or more pharmaceutically acceptable carriers, diluents or excipients.

22. A method of treating pain in a subject, the method comprising administering to the subject the pharmaceutical composition of claim 21.

23. The method according to claim 22, wherein the pain is selected from the group consisting of postoperative pain, pain induced by a cancer, neuropathic pain, traumatic pain and inflammatory pain.

24. The method according to claim 23, wherein the cancer is selected from the group consisting of breast cancer, endometrial cancer, cervical cancer, skin cancer, prostate cancer, ovarian cancer, fallopian tube tumor, ovarian tumor, hemophilia and leukemia.

* * * * *